US012679903B2

(12) United States Patent
Kim et al.

(10) Patent No.: US 12,679,903 B2
(45) Date of Patent: Jul. 14, 2026

(54) ANTIBODY FOR SPECIFICALLY BINDING TO LYSYL-TRNA SYNTHETASE N-TERMINAL DOMAIN EXPOSED TO EXTRACELLULAR MEMBRANE

(71) Applicant: Zymedi Co., Ltd., Incheon (KR)

(72) Inventors: Sunghoon Kim, Gyeonggi-Do (KR); Nam Hoon Kwon, Gyeonggi-do (KR)

(73) Assignee: Zymedi Co., Ltd., Incheon (KR)

( * ) Notice: Subject to any disclaimer, the term of this patent is extended or adjusted under 35 U.S.C. 154(b) by 456 days.

(21) Appl. No.: 17/276,570

(22) PCT Filed: Sep. 17, 2019

(86) PCT No.: PCT/KR2019/011998
§ 371 (c)(1),
(2) Date: Mar. 16, 2021

(87) PCT Pub. No.: WO2020/060156
PCT Pub. Date: Mar. 26, 2020

(65) Prior Publication Data
US 2022/0049016 A1 Feb. 17, 2022

(30) Foreign Application Priority Data

Sep. 17, 2018 (KR) ........................ 10-2018-0111046

(51) Int. Cl.
C07K 16/40 (2006.01)
A61K 39/00 (2006.01)
G01N 33/575 (2026.01)

(52) U.S. Cl.
CPC ......... *C07K 16/40* (2013.01); *G01N 33/5759* (2026.01); *A61K 2039/505* (2013.01); *C07K 2317/92* (2013.01); *G01N 2333/9015* (2013.01)

(58) Field of Classification Search
CPC ................ C07K 16/40; C07K 2317/56; C07K 2317/565; G01N 33/57492; A61K 2039/505
See application file for complete search history.

(56) References Cited

U.S. PATENT DOCUMENTS 5,595,756 A * 1/1997 Bally ................... A61K 9/1272
264/4.1

FOREIGN PATENT DOCUMENTS

| CN | 103118694 A | 5/2013 |
|---|---|---|
| CN | 111629752 A | 9/2020 |
| KR | 10-2010-0040583 A | 4/2010 |
| KR | 10-1546652 B1 | 8/2015 |
| KR | 101658625 B1 | 9/2016 |
| KR | 10-2017-0100206 A | 9/2017 |
| KR | 10-2019-0031189 A | 3/2019 |

| WO | 0140302 A2 | 6/2001 |
|---|---|---|
| WO | 2011153277 A2 | 12/2011 |
| WO | 2018182284 A1 | 10/2018 |
| WO | 2019054819 A1 | 3/2019 |

OTHER PUBLICATIONS

Sela-Culang et al., The structural basis of antibody-antigen recognition, 2013, Frontiers in Immunology, vol. 4, Article 302, pp. 1-13 (Year: 2013).*
Kussie et al., A Single Engineered Amino Acid Substitution Changes Antibody Fine Specificity, 1994, Journal of Immunology, pp. 146-152 (Year: 1994).*
Auerbach et al., Angiogenesis assays: Problems and pitfalls, 2000, Cancer and Metastasis Reviews, vol. 19, pp. 167-172 (Year: 2000).*
Hogenesch et al., Challenges in pre-clinical testing of anti-cancer drugs in cell culture and in animal models, 2012, Journal of Control Release, vol. 164, Issue 2, pp. 183-186 (Year: 2012).*
Christiansen et al., Biological impediments to monoclonal antibody-based cancer immunotherapy, 2004, Molecular Cancer Therapeutics, vol. 4, Issue 3, pp. 1493-1501 (Year: 2004).*
Shirani et al., Therapeutic Advances and Future Prospects in Progressive Forms of Multiple Sclerosis, 2016, Neurotherapeutics, vol. 13, pp. 58-69 (Year: 2016).*
Rosenblum et al., Treating Human Autoimmunity: Current Practice and Future Prospects, 2012, Science Translational Medicine, vol. 4, Issue 125, pp. 1-20 (Year: 2012).*
Mackay et al., Autoimmune Diseases, 2001, The New England Journal of Medicine, vol. 345, No. 5, pp. 340-350 (Year: 2001).*
Bozza et al. Macrophage Migration Inhibitory Factor Levels Correlate With Fatal Outcome in Sepsis.Shock, vol. 22, No. 4, pp. 309-313, 2004.
Gregory et al. Macrophage Migration Inhibitory Factor Induces Macrophage Recruitment via CC Chemokine Ligand 2. The Journal of Immunology, 2006, 177: 8072-8079.
Grieb et al. Macrophage migration inhibitory factor (MIF): a promising biomarker. Drug News Perspect. May 2010 ; 23 (4): 257-264. doi:10.1358/dnp.2010.23.4.1453629.

(Continued)

*Primary Examiner* — Jeffrey Stucker
*Assistant Examiner* — Brittney E Donoghue
(74) *Attorney, Agent, or Firm* — Banner & Witcoff, Ltd.

(57) ABSTRACT

The present invention relates to an antibody that specifically binds to the lysyl-tRNA synthase N-terminal domain exposed to the extracellular membrane, more specifically, it specifically binds to the lysyl-tRNA synthetase (KRS, Lysyl-tRNA synthetase)N-terminal domain exposed to the extracellular membrane having a specific CDR (complementarity determining region) sequence described herein, and relates to the use for the prevention, treatment or diagnosis of cancer, cancer metastasis, or diseases related to immune cell migration of a composition comprising an antibody or fragment thereof having high affinity and stability or the antibody and fragment thereof as an active ingredient. The method of the present invention can be usefully used to prepare an antibody having a higher affinity for the KRS N-terminus than a conventional antibody.

15 Claims, 20 Drawing Sheets
(15 of 20 Drawing Sheet(s) Filed in Color)

Specification includes a Sequence Listing.

(56) References Cited

OTHER PUBLICATIONS

Stifano et al. Macrophage Involvement in Systemic Sclerosis: Do We Need More Evidence? Curr Rheumatol Rep (2016) 18: 2. DOI 10.1007/s11926-015-0554-8.

Chen et al. Enhancement of CCL2 expression and monocyte migration by CCN1 in osteoblasts through inhibiting miR-518a-5p: implication of rheumatoid arthritis therapy. Scientific Reports | 7: 421 | DOI:10.1038/s41598-017-00513-0.

Jones et al. Dynamics of Colon Monocyte and Macrophage Activation During Colitis. Front. Immunol. 9:2764. doi: 10.3389/fimmu.2018.02764.

Kiekens et al. Heterogeneity within tissue-specific macrophage and dendritic cell populations during cutaneous inflammation in atopic dermatitis. British Journal of Dermatology 2001; 145: 957-965.

Rangasamy et al. Chemokine Mediated Monocyte Trafficking into the Retina: Role of Inflammation in Alteration of the Blood- Retinal Barrier in Diabetic Retinopathy. PLOS ONE, Oct. 2014, vol. 9 , Issue 10, e108508.

Saradna et al. Macrophage Polarization and Allergic Asthma. Transl Res. Jan. 2018 ; 191: 1-14. doi: 10.1016/j.trsl.2017.09.002 .

Kang et al. Cytology of Nasal Secretions in Rhinitis and Sinusitis. Korean J Otolaryngol 1998;41(5):586-589.

Gracia et al. Rapid recruitment of CD141 monocytes in experimentally induced allergic rhinitis in human subjects. J Allergy Clin Immunol 2016;137:1872-81.).

Yokoyama, et al. IL-2-Anti-IL-2 Monoclonal Antibody Immune Complexes Inhibit Collagen-Induced Arthritis by Augmenting Regulatory T Cell Functions. 01502 Aug. 2018; J Immunol 2018; 201:1899-1906; Prepublished online Aug. 24, 2018; doi: 10.4049/jimmunol.1701502.

Dalbeth et al. Cellular Characterization of the Gouty Tophus. Arthritis & Rheumatism vol. 62, No. 5, May 2010, pp. 1549-1556 DOI 10.1002/art.27356.

Guerne et al. Inflammatory Microcrystals Stimulate Interleukin-6 Production and Secretion by Human Monocytes and Synoviocytes. Arthritis and Rheumatism, vol. 32, No. 11 (Nov. 1989).

Dantas et al. Macrophage-mediated psoriasis can be suppressed by regulatory T lymphocytes. Journal of Pathology J Pathol 2016; 240: 366-377.DOI: 10.1002/path.4786.

Ma et al. The Role of Monocytes and Macrophages in Autoimmune Diseases: A Comprehensive Review. Front. Immunol. 10:1140. doi: 10.3389/fimmu.2019.01140. Review published: May 24, 2019.

Russell et al. Release and Activity of Matrix Metalloproteinase-9 and Tissue Inhibitor of Metalloproteinase-1 by Alveolar Macrophages from Patients with Chronic Obstructive Pulmonary Disease. Am. J. Respir. Cell Mol. Biol. vol. 26, pp. 602-609, 2002.

Hirose et al. Monocyte subsets involved in the development of systemic lupus erythematosus and rheumatoid arthritis. International Immunology, vol. 31, No. 11, pp. 687-696 doi: 10.1093/intimm/dxz036. Advance Access publication Apr. 11, 2019.

Iqbal et al. Updated Treatment for Calcium Pyrophosphate Deposition Disease: An Insight. Cureus 11(1): e3840. DOI 10.7759/cureus.3840. Published Jan. 7, 2019.

Strawn et al. Novel mechanisms linking angiotensin II and early atherogenesis. JRAAS 2000; 1:11-17.

Brempelis et al. Infiltrating monocytes in liver injury and repair. Clinical & Translational Immunology (2016) 5, e113; doi:10.1038/cti.2016.62.

Calle et al. Macrophage Phenotype and Fibrosis in Diabetic Nephropathy. Int. J. Mol. Sci. 2020, 21, 2806; doi: 10.3390/ijms21082806.

Alvarado-Vázquez et al. Cytokine production capabilities of human primary monocyte-derived macrophages from patients with diabetes mellitus type 2 with and without diabetic peripheral neuropathy. Journal of Pain Research 2019:12 69-81.

Conti et al. Macrophage infiltration and death in the nerve during the early phases of experimental diabetic neuropathy: a process concomitant with endoneurial induction of IL-1b and p75NTR. Journal of the Neurological Sciences 195 (2002) 35-40.

Wick et al. The immunology of fibrosis: innate and adaptive responses. Trends Immunol. Mar. 2010 ; 31(3): 110-119. doi:10.1016/j.it.2009.12.001.

* cited by examiner

Mock 100 nM          N3 10 nM          N3-1 10 nM

| | ka (1/Ms) | kd (1/s) | KD (nM) |
|---|---|---|---|
| N3 | 709507.7 | 0.063682 | 90 |
| N3-1 | 664189.6 | 0.020574 | 31 |

| Peptide | Ab | Ka (1/Ms) | Kd (1/s) | KD (nM) |
|---------|------|-----------|-----------|---------|
| | N3-6 | 34790 | 0.0001431 | 4.114 |
| | N3-7 | 31190 | 0.0005855 | 18.77 |
| F4 | N3-8 | 460800 | 0.0003969 | 0.8613 |
| | N3-9 | 396500 | 0.001127 | 2.842 |

CD68: Monocytes/macropahge marker

Total cells

Neutrophils

Acute lung injury model

Red: keratin and muscle fibers,
blue or green: collagen (fibrosis) and bone
light red or pink: cytoplasm
dark brown to black: cell nuclei C: Control
LN: LN421 only
1: LN421+N3-8
2: LN421+N3-8-1
3: LN421+N3-8-1 mutant LALA
4: LN421+N3-8-1 mutant LALATA
5: LN421+N3-8-1 mutant LALAPG
6: LN421+N3-8-1 mutant LALAPGTA C: Control
LN: Laminin only
1: LN+N3-8
2: LN+N3-8-1
3: LN+N3-8-1 mutant LALA
4: LN+N3-8-1 mutant LALATA
5: LN+N3-8-1 mutant LALAPG
6: LN+N3-8-1 mutant LALAPGTA

SEQUENCE LISTING

```
<160> NUMBER OF SEQ ID NOS: 255

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H1 amino acid

<400> SEQUENCE: 1

Ser Tyr Asp Met Ser
1               5

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H1 DNA

<400> SEQUENCE: 2
agttatgata tgagc                                                       15
```

-continued

```
<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 amino acid

<400> SEQUENCE: 3

Ala Ile Ser Tyr Asp Asn Gly Asn Thr Tyr Tyr Ala Asp Ser Val Lys
1               5                   10                  15

Gly

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 DNA

<400> SEQUENCE: 4
gcgatctctt atgataatgg taatacatat tacgctgatt ctgtaaaagg t          51

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H3 amino acid

<400> SEQUENCE: 5

Met Ala Leu Asp Phe Asp Tyr
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H3 DNA

<400> SEQUENCE: 6
atggcgcttg atttcgacta c                                           21

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L1 amino acid

<400> SEQUENCE: 7

Thr Gly Ser Ser Ser Asn Ile Gly Ser Asn Tyr Val Thr
```

-continued

```
1               5                   10
```

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L1 DNA

<400> SEQUENCE: 8
actggctctt catctaatat tggcagtaat tatgtcacc                           39

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L2 amino acid

<400> SEQUENCE: 9

Asp Asn Ser Asn Arg Pro Ser
1               5

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L2 DNA

<400> SEQUENCE: 10
gataatagta atcggccaag c                                              21

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L3 amino acid

<400> SEQUENCE: 11

Ala Ser Trp Asp Asp Ser Leu Ser Ala Tyr Val
1               5                   10

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L3 DNA

<400> SEQUENCE: 12
gcttcttggg atgatagcct gagtgcttat gtc                                 33
```

-continued

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L3 mutant 1 amino acid

<400> SEQUENCE: 13

Ala Ser Phe Ser Asp Glu Leu Gly Ala Tyr Val
1               5                   10

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L3 mutant 1 DNA

<400> SEQUENCE: 14 gcttcttttta gtgatgagtt gggggcttat gtc                                    33

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L3 mutant 2 amino acid

<400> SEQUENCE: 15

Ser Ser Phe Ser Asp Glu Leu Gly Ala Tyr Val
1               5                   10

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L3 mutant 2 DNA

<400> SEQUENCE: 16 tcttcttttta gtgatgagtt gggggcttat gtc                                    33

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 1 amino acid

<400> SEQUENCE: 17

Ala Ile Ser Pro Gln Met Gly Arg Val Tyr Tyr Ala Asp Ser Val Lys
1               5                   10                  15

Gly

```
<210> SEQ ID NO 18
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 1 DNA

<400> SEQUENCE: 18
gcgatctcgc cgcagatggg tcgggtgtat tacgctgatt ctgtaaaagg t             51

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 2 amino acid

<400> SEQUENCE: 19

Ala Ile Asp Pro Leu Gly Gly Asn Ile Tyr Tyr Ala Asp Ser Val Lys
1               5                   10                  15

Gly

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 2 DNA

<400> SEQUENCE: 20
gcgatcgatc cgttgggggg taatatttat tacgctgatt ctgtaaaagg t             51

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 3 amino acid

<400> SEQUENCE: 21

Ala Ile Ser Pro Tyr Ser Gly Arg Ile Tyr Tyr Ala Asp Ser Val Lys
1               5                   10                  15

Gly

<210> SEQ ID NO 22
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 3 DNA

<400> SEQUENCE: 22
```
gcgatctctc cgtattcggg taggatttat tacgctgatt ctgtaaaagg t            51

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 4 amino acid

<400> SEQUENCE: 23

Ala Ile Gly Ala Asp Gly Gly Pro Ser Tyr Tyr Ala Asp Ser Val Lys
1               5                   10                  15

Gly

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H2 mutant 4 DNA

<400> SEQUENCE: 24
gcgatcgggg ctgatggggg tccgtcttat tacgctgatt ctgtaaaagg t            51

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H3 mutant 1 amino acid

<400> SEQUENCE: 25

Leu Ala Leu Asp Phe Asp Tyr
1               5

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR H3 mutant 1 DNA

<400> SEQUENCE: 26
ctggcgcttg atttcgacta c                                            21

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L2 mutant 1 amino acid

<400> SEQUENCE: 27

Ser Asn Asn Gln Arg Pro Ser
1               5

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L2 mutant 1 DNA

<400> SEQUENCE: 28
agtaataatc agcggccaag c                                              21

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR L2 mutant 2 amino acid

<400> SEQUENCE: 29

Arg Asn Asn Gln Arg Pro Ser
1               5

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: CDR L2 mutant 2 DNA

<400> SEQUENCE: 30
cggaataatc agcggccaag c                                              21

<210> SEQ ID NO 31
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser

```
                    85              90              95
Ala Arg Met Ala Leu Asp Phe Asp Tyr Trp Gly Gln Gly Thr Leu Val
            100             105             110

Thr Val Ser Ser
        115
```

<210> SEQ ID NO 32
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH

<400> SEQUENCE: 32

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctca                  348
```

<210> SEQ ID NO 33
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL

<400> SEQUENCE: 33

```
Gln Ser Val Leu Thr Gln Pro Pro Ser Ala Ser Gly Thr Pro Gly Gln
1               5                  10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu
            100             105             110
```

<210> SEQ ID NO 34
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL

<400> SEQUENCE: 34

```
cagtctgtgc tgactcagcc accctcagcg tctgggaccc ccgggcagag ggtcaccatc        60
tcttgtactg gctcttcatc taatattggc agtaattatg tcacctggta ccagcagctc       120
ccaggaacgg cccccaaact cctcatctat gataatagta atcggccaag cggggtccct       180
gaccgattct ctggctccaa gtctggcacc tcagcctccc tggccatcag tgggctccgg       240
tccgaggatg aggctgatta ttactgtgct tcttgggatg atagcctgag tgcttatgtc       300
ttcggcggag gcaccaagct gacggtccta                                        330
```

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 1

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115
```

<210> SEQ ID NO 36
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 1

<400> SEQUENCE: 36

```
gaggtgcagc tgttggagtc tggggaggc ttggtacagc ctgggggtc cctgagactc        60 tcctgtgcag cctctggatt caccttagc agttatgata tgagctgggt ccgccaggct       120
ccagggaagg ggctggagtg ggtctcagtg atctcttctg atggtggtaa tacatattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctca                    348
```

<210> SEQ ID NO 37
<211> LENGTH: 116
<212> TYPE: PRT

-continued

---

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 2

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 38
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 2

<400> SEQUENCE: 38
gaggtgcagc tgttggagtc tgggggaggc ttggtacagc ctggggggtc cctgagactc     60
tcctgtgcag cctctggatt cacctttagc agttatgata tgagctgggt ccgccaggct    120
ccagggaagg ggctggagtg ggtctcagcg atctcgccgc agatgggtcg ggtgtattac    180
gctgattctg taaaaggtcg gttcaccatc tccagagaca attccaagaa cacgctgtat    240
ctgcaaatga acagcctgag agccgaggac acggccgtgt attactgtgc gagaatggcg    300
cttgatttcg actactgggg ccagggtaca ctggtcaccg tgagctca                 348

<210> SEQ ID NO 39
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 3

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45
```

```
Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser
        115
```

```
<210> SEQ ID NO 40
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 3

<400> SEQUENCE: 40
gaggtgcagc tgttggagtc tgggggaggc ttggtacagc ctggggggtc cctgagactc        60
tcctgtgcag cctctggatt cacctttagc agttatgata tgagctgggt ccgccaggct       120
ccagggaagg ggctggagtg ggtctcagcg atcgatccgt tggggggtaa tatttattac       180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctca                    348
```

```
<210> SEQ ID NO 41
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 4

<400> SEQUENCE: 41

Glu Val Gln Leu Leu Glu Ser Gly Gly Gly Leu Val Gln Pro Gly Gly
1                   5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser
        115
```

```
<210> SEQ ID NO 42
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 4

<400> SEQUENCE: 42
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctca                   348

<210> SEQ ID NO 43
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 5

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser
        115

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 5

<400> SEQUENCE: 44
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atcggggctg atggggggtcc gtcttattac     180
```

```
gctgattctg taaaaggtcg gttcaccatc tccagagaca attccaagaa cacgctgtat      240
ctgcaaatga acagcctgag agccgaggac acggccgtgt attactgtgc gagaatggcg      300
cttgatttcg actactgggg ccagggtaca ctggtcaccg tgagctca                  348
```

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 6

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser
        115
```

<210> SEQ ID NO 46
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 6

<400> SEQUENCE: 46

```
gaggtgcagc tgttggagtc tggggggaggc ttggtacagc ctggggggtc cctgagactc       60
tcctgtgcag cctctggatt cacctttagc agttatgata tgagctgggt ccgccaggct      120
ccagggaagg ggctggagtg ggtctcagcg atctctccgt attcgggtag gatttattac      180
gctgattctg taaaaggtcg gttcaccatc tccagagaca attccaagaa cacgctgtat      240
ctgcaaatga acagcctgag agccgaggac acggccgtgt attactgtgc gagaatggcg      300
cttgatttcg actactgggg ccagggtaca ctggtcaccg tgagctca                  348
```

<210> SEQ ID NO 47
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VH mutant 7

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser
        115

<210> SEQ ID NO 48
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VH mutant 7

<400> SEQUENCE: 48
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctca                  348

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 1

<400> SEQUENCE: 49

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

-continued

```
Ser Glu Asp Glu Ala Asp Tyr Tyr Cys Ala Ser Phe Ser Asp Glu Leu
                85                  90                  95

Gly Ala Tyr Val Phe Gly Gly Gly Thr Lys Leu Thr Val Leu
            100                 105                 110

<210> SEQ ID NO 50
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 1

<400> SEQUENCE: 50
cagtctgtgc tgactcagcc accctcagcg tctgggaccc ccgggcagag ggtcaccatc        60
tcttgtactg gctcttcatc taatattggc agtaattatg tcacctggta ccagcagctc       120
ccaggaacgg cccccaaact cctcatctat gataatagta tcggccaag cggggtccct        180 gaccgattct ctggctccaa gtctggcacc tcagcctccc tggccatcag tgggctccag       240
tccgaggatg aggctgatta ttactgtgct tcttttagtg atgagttggg ggcttatgtc       300
ttcggcggag gcaccaagct gacggtccta                                        330

<210> SEQ ID NO 51
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 2

<400> SEQUENCE: 51

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
            100                 105                 110

<210> SEQ ID NO 52
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 2

<400> SEQUENCE: 52
```

```
cagtctgtgc tgactcagcc accctcagcg tctgggaccc ccgggcagag ggtcaccatc        60
tcttgtactg gctcttcatc taatattggc agtaattatg tcacctggta ccagcagctc       120
ccaggaacgg cccccaaact cctcatctat gataatagta atcggccaag cggggtccct       180
gaccgattct ctggctccaa gtctggcacc tcagcctccc tggccatcag tgggctccag       240
tccgaggatg aggctgatta ttactgttct tcttttagtg atgagttggg ggcttatgtc       300
ttcggcggag gcaccaagct gacggtccta                                        330
```

```
<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 VL mutant 3

<400> SEQUENCE: 53

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
            100                 105                 110
```

```
<210> SEQ ID NO 54
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 3

<400> SEQUENCE: 54
cagtctgtgc tgactcagcc accctcagcg tctgggaccc ccgggcagag ggtcaccatc        60
tcttgtactg gctcttcatc taatattggc agtaattatg tcacctggta ccagcagctc       120
ccaggaacgg cccccaaact cctcatctat agtaataatc agcggccaag cggggtccct       180
gaccgattct ctggctccaa gtctggcacc tcagcctccc tggccatcag tgggctccag       240
tccgaggatg aggctgatta ttactgttct tcttttagtg atgagttggg ggcttatgtc       300
ttcggcggag gcaccaagct gacggtccta                                        330
```

```
<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: N3 VL mutant 4

<400> SEQUENCE: 55

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
                20                  25                  30

Tyr Val Thr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu
                100                 105                 110

<210> SEQ ID NO 56
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 VL mutant 4

<400> SEQUENCE: 56
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat cggaataatc agcggccaag cggggtccct     180
gaccgattct ctggctccaa gtctggcacc tcagcctccc tggccatcag tgggctccag     240
tccgaggatg aggctgatta ttactgttct cttttagtg atgagttggg ggcttatgtc      300
ttcggcggag gcaccaagct gacggtccta                                      330

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker for scFv

<400> SEQUENCE: 57

Gly Gly Gly Gly Ser Gly Gly Gly Gly Ser Gly Gly Gly Gly Ser
1               5                   10                  15

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Linker for scFv

<400> SEQUENCE: 58
```

-continued ggtggaggcg gttcaggcgg aggtggatcc ggcggtggcg gatcg                    45

<210> SEQ ID NO 59
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 scFv (VH+linker+VL)

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
            195                 200                 205

Gly Leu Arg Ser Glu Asp Glu Ala Asp Tyr Tyr Cys Ala Ser Trp Asp
        210                 215                 220

Asp Ser Leu Ser Ala Tyr Val Phe Gly Gly Gly Thr Lys Leu Thr Val
225                 230                 235                 240

Leu

<210> SEQ ID NO 60
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 scFv (VH+linker+VL)

<400> SEQUENCE: 60
gaggtgcagc tgttggagtc tgggggaggc ttggtacagc ctggggggtc cctgagactc    60
tcctgtgcag cctctggatt caccttttagc agttatgata tgagctgggt ccgccaggct   120

-continued

```
ccagggaagg ggctggagtg ggtctcagcg atctcttatg ataatggtaa tacatattac      180
gctgattctg taaaaggtcg gttcaccatc tccagagaca attccaagaa cacgctgtat      240
ctgcaaatga acagcctgag agccgaggac acggccgtgt attactctgc gagaatggcg      300
cttgatttcg actactgggg ccagggtaca ctggtcaccg tgagctcagg tggaggcggt      360
tcaggcggag gtggatccgg cggtggcgga tcgcagtctg tgctgactca gccaccctca      420
gcgtctggga cccccgggca gagggtcacc atctcttgta ctggctcttc atctaatatt      480
ggcagtaatt atgtcacctg gtaccagcag ctcccaggaa cggcccccaa actcctcatc      540
tatgataata gtaatcggcc aagcggggtc cctgaccgat tctctggctc caagtctggc      600
acctcagcct ccctggccat cagtgggctc cggtccgagg atgaggctga ttattactgt      660
gcttcttggg atgatagcct gagtgcttat gtcttcggcg aggcaccaa gctgacggtc       720 cta                                                                   723
```

<210> SEQ ID NO 61
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-1 scFv (VH+linker+VL)

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Tyr Asp Asn Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
                180                 185                 190

Arg Phe Ser Gly Ser Lys Ser Gly Thr Ser Ala Ser Leu Ala Ile Ser
            195                 200                 205

Gly Leu Gln Ser Glu Asp Glu Ala Asp Tyr Tyr Cys Ala Ser Phe Ser
        210                 215                 220

Asp Glu Leu Gly Ala Tyr Val Phe Gly Gly Gly Thr Lys Leu Thr Val
```

-continued

```
          225              230              235              240

Leu

<210> SEQ ID NO 62
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-1 scFv (VH+linker+VL)

<400> SEQUENCE: 62
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcgggggtc cctgaccgat tctctggctc caagtctggc     600
acctcagcct ccctggccat cagtgggctc cagtccgagg atgaggctga ttattactgt     660
gcttctttta gtgatgagtt gggggcttat gtcttcggcg gaggcaccaa gctgacggtc     720
cta                                                                    723

<210> SEQ ID NO 63
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-3 scFv (VH+linker+VL)

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125
```

-continued

```
Gly Gly Ser Gln Ser Val Leu Thr Gln Pro Pro Ser Ala Ser Gly Thr
    130                 135                 140
```

```
Pro Gly Gln Arg Val Thr Ile Ser Cys Thr Gly Ser Ser Ser Asn Ile
145                 150                 155                 160
```

```
Gly Ser Asn Tyr Val Thr Trp Tyr Gln Gln Leu Pro Gly Thr Ala Pro
                165                 170                 175
```

```
Lys Leu Leu Ile Tyr Asp Asn Ser Asn Arg Pro Ser Gly Val Pro Asp
            180                 185                 190
```

```
Arg Phe Ser Gly Ser Lys Ser Gly Thr Ser Ala Ser Leu Ala Ile Ser
        195                 200                 205
```

```
Gly Leu Gln Ser Glu Asp Glu Ala Asp Tyr Tyr Cys Ser Ser Phe Ser
    210                 215                 220
```

```
Asp Glu Leu Gly Ala Tyr Val Phe Gly Gly Gly Thr Lys Leu Thr Val
225                 230                 235                 240
```

```
Leu
```

<210> SEQ ID NO 64
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-3 scFv (VH+linker+VL)

<400> SEQUENCE: 64

```
gaggtgcagc tgttggagtc tggggggaggc ttggtacagc ctggggggtc cctgagactc        60
tcctgtgcag cctctggatt caccttttagc agttatgata tgagctgggt ccgccaggct       120
ccagggaagg ggctggagtg ggtctcagcg atctcttatg ataatggtaa tacatattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctcagg tggaggcggt       360
tcaggcggag gtggatccgg cggtggcgga tcgcagtctg tgctgactca gccaccctca       420
gcgtctggga cccccgggca gagggtcacc atctcttgta ctggctcttc atctaatatt       480
ggcagtaatt atgtcacctg gtaccagcag ctcccaggaa cggccccca actcctcatc       540 tatgataata gtaatcggcc aagcggggtc cctgaccgat tctctggctc caagtctggc       600
acctcagcct ccctggccat cagtgggctc cagtccgagg atgaggctga ttattactgt       660
tcttctttta gtgatgagtt gggggcttat gtcttcggcg gaggcaccaa gctgacggtc       720
cta                                                                      723
```

<210> SEQ ID NO 65
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-4 scFv (VH+linker+VL)

<400> SEQUENCE: 65

```
Glu Val Gln Leu Leu Glu Ser Gly Gly Gly Leu Val Gln Pro Gly Gly
1               5                   10                  15
```

-continued

```
Ser Leu Arg Leu Ser Cys Ala Ala Ser Gly Phe Thr Phe Ser Ser Tyr
         20                  25                  30

Asp Met Ser Trp Val Arg Gln Ala Pro Gly Lys Gly Leu Glu Trp Val
         35                  40                  45

Ser Val Ile Ser Ser Asp Gly Gly Asn Thr Tyr Tyr Ala Asp Ser Val
         50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                 85                  90                  95

Ala Arg Met Ala Leu Asp Phe Asp Tyr Trp Gly Gln Gly Thr Leu Val
             100                 105                 110

Thr Val Ser Ser Gly Gly Gly Gly Ser Gly Gly Gly Gly Ser Gly Gly
         115                 120                 125

Gly Gly Ser Gln Ser Val Leu Thr Gln Pro Pro Ser Ala Ser Gly Thr
         130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                 165                 170                 175

Lys Leu Leu Ile Tyr Asp Asn Ser Asn Arg Pro Ser Gly Val Pro Asp
             180                 185                 190

Arg Phe Ser Gly Ser Lys Ser Gly Thr Ser Ala Ser Leu Ala Ile Ser
         195                 200                 205

Gly Leu Gln Ser Glu Asp Glu Ala Asp Tyr Tyr Cys Ala Ser Phe Ser
         210                 215                 220

Asp Glu Leu Gly Ala Tyr Val Phe Gly Gly Gly Thr Lys Leu Thr Val
225                 230                 235                 240

Leu
```

```
<210> SEQ ID NO 66
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-4 scFv (VH+linker+VL)

<400> SEQUENCE: 66
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcgggggtc cctgaccgat tctctggctc caagtctggc     600
acctcagcct ccctggccat cagtgggctc cagtccgagg atgaggctga ttattactgt     660
``` gcttcttta gtgatgagtt gggggcttat gtcttcggcg gaggcaccaa gctgacggtc     720
cta                                                                          723

<210> SEQ ID NO 67
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-5 scFv (VH+linker+VL)

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
            195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 68
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-5 scFv (VH+linker+VL)

<400> SEQUENCE: 68
gaggtgcagc tgttggagtc tggggggaggc ttggtacagc ctggggggtc cctgagactc     60

```
tcctgtgcag cctctggatt cacctttagc agttatgata tgagctgggt ccgccaggct       120
ccagggaagg ggctggagtg ggtctcagtg atctcttctg atggtggtaa tacatattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctcagg tggaggcggt       360
tcaggcggag gtggatccgg cggtggcgga tcgcagtctg tgctgactca gccaccctca       420
gcgtctggga cccccgggca gagggtcacc atctcttgta ctggctcttc atctaatatt       480
ggcagtaatt atgtcacctg gtaccagcag ctcccaggaa cggcccccaa actcctcatc       540
tatgataata gtaatcggcc aagcggggtc cctgaccgat tctctggctc caagtctggc       600
acctcagcct ccctggccat cagtgggctc cagtccgagg atgaggctga ttattactgt       660
tcttctttta gtgatgagtt ggggggcttat gtcttcggcg gaggcaccaa gctgacggtc       720
cta                                                                    723
```

```
<210> SEQ ID NO 69
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-6 scFv (VH+linker+VL)

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220
```

-continued

```
Asp Glu Leu Gly Ala Tyr Val Phe Gly Gly Gly Thr Lys Leu Thr Val
225                 230                 235                 240

Leu
```

<210> SEQ ID NO 70
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-6 scFv (VH+linker+VL)

<400> SEQUENCE: 70

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg aggcaccaa gctgacggtc      720 cta                                                                    723
```

<210> SEQ ID NO 71
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-7 scFv (VH+linker+VL)

<400> SEQUENCE: 71

```
Glu Val Gln Leu Leu Glu Ser Gly Gly Gly Leu Val Gln Pro Gly Gly
1                 5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
```

-continued

```
              115               120               125

Gly Gly Ser Gln Ser Val Leu Thr Gln Pro Pro Ser Ala Ser Gly Thr
    130               135               140

Pro Gly Gln Arg Val Thr Ile Ser Cys Thr Gly Ser Ser Ser Asn Ile
145               150               155               160

Gly Ser Asn Tyr Val Thr Trp Tyr Gln Gln Leu Pro Gly Thr Ala Pro
                165               170               175

Lys Leu Leu Ile Tyr Asp Asn Ser Asn Arg Pro Ser Gly Val Pro Asp
            180               185               190

Arg Phe Ser Gly Ser Lys Ser Gly Thr Ser Ala Ser Leu Ala Ile Ser
        195               200               205

Gly Leu Gln Ser Glu Asp Glu Ala Asp Tyr Tyr Cys Ser Ser Phe Ser
    210               215               220

Asp Glu Leu Gly Ala Tyr Val Phe Gly Gly Gly Thr Lys Leu Thr Val
225               230               235               240

Leu
```

```
<210> SEQ ID NO 72
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-7 scFv (VH+linker+VL)

<400> SEQUENCE: 72
gaggtgcagc tgttggagtc tggggggaggc ttggtacagc ctggggggtc cctgagactc        60
tcctgtgcag cctctggatt caccttttagc agttatgata tgagctgggt ccgccaggct       120
ccagggaagg ggctggagtg ggtctcagcg atcgatccgt tggggggtaa tatttattac       180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctcagg tggaggcggt       360
tcaggcggag gtggatccgg cggtggcgga tcgcagtctg tgctgactca gccaccctca       420
gcgtctggga cccccgggca gagggtcacc atctcttgta ctggctcttc atctaatatt       480
ggcagtaatt atgtcacctg gtaccagcag ctcccaggaa cggcccccaa actcctcatc       540
tatgataata gtaatcggcc aagcgggggtc cctgaccgat tctctggctc caagtctggc       600
acctcagcct ccctggccat cagtgggctc cagtccgagg atgaggctga ttattactgt       660
tcttctttta gtgatgagtt gggggcttat gtcttcggcg gaggcaccaa gctgacggtc       720
cta                                                                     723
```

```
<210> SEQ ID NO 73
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-7 scFv (VH+linker+VL)

<400> SEQUENCE: 73

Glu Val Gln Leu Leu Glu Ser Gly Gly Gly Leu Val Gln Pro Gly Gly
1               5               10               15
```

```
Ser Leu Arg Leu Ser Cys Ala Ala Ser Gly Phe Thr Phe Ser Ser Tyr
        20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

```
<210> SEQ ID NO 74
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-7 scFv (VH+linker+VL)

<400> SEQUENCE: 74
```

```
gaggtgcagc tgttggagtc tggggggaggc ttggtacagc ctggggggtc cctgagactc       60
tcctgtgcag cctctggatt caccttttagc agttatgata tgagctgggt ccgccaggct      120
ccagggaagg ggctggagtg ggtctcagcg atctctccgt attcgggtag gatttattac      180
gctgattctg taaaaggtcg gttcaccatc tccagagaca attccaagaa cacgctgtat      240
ctgcaaatga acagcctgag agccgaggac acggccgtgt attactctgc gagaatggcg      300
cttgatttcg actactgggg ccagggtaca ctggtcaccg tgagctcagg tggaggcggt      360
tcaggcggag gtggatccgg cggtggcgga tcgcagtctg tgctgactca gccaccctca      420
gcgtctggga cccccgggca gagggtcacc atctcttgta ctggctcttc atctaatatt      480
ggcagtaatt atgtcacctg gtaccagcag ctcccaggaa cggcccccaa actcctcatc      540
tatgataata gtaatcggcc aagcgggggtc cctgaccgat tctctggctc caagtctggc      600
acctcagcct ccctggccat cagtgggctc cagtccgagg atgaggctga ttattactgt      660
```

-continued

```
tcttcttta gtgatgagtt gggggcttat gtcttcggcg gaggcaccaa gctgacggtc      720
cta                                                                  723
```

<210> SEQ ID NO 75
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-9 scFv (VH+linker+VL)

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 76
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-9 scFv (VH+linker+VL)

<400> SEQUENCE: 76
gaggtgcagc tgttggagtc tgggggaggc ttggtacagc ctggggggtc cctgagactc      60

-continued

```
tcctgtgcag cctctggatt cacctttagc agttatgata tgagctgggt ccgccaggct        120
ccagggaagg ggctggagtg ggtctcagcg atcggggctg atggggggtcc gtcttattac       180 gctgattctg taaaaggtcg gttcaccatc tccagagaca attccaagaa cacgctgtat        240
ctgcaaatga acagcctgag agccgaggac acggccgtgt attactgtgc gagaatggcg        300
cttgatttcg actactgggg ccagggtaca ctggtcaccg tgagctcagg tggaggcggt        360
tcaggcggag gtggatccgg cggtggcgga tcgcagtctg tgctgactca gccaccctca        420
gcgtctggga cccccgggca gagggtcacc atctcttgta ctggctcttc atctaatatt       480
ggcagtaatt atgtcacctg gtaccagcag ctcccaggaa cggcccccaa actcctcatc        540
tatgataata gtaatcggcc aagcggggtc cctgaccgat tctctggctc caagtctggc        600
acctcagcct ccctggccat cagtgggctc cagtccgagg atgaggctga ttattactgt        660
tcttctttta gtgatgagtt ggggggctta t gtcttcggcg aggcaccaa gctgacggtc       720 cta                                                                       723
```

<210> SEQ ID NO 77
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8 scFv, N3-8-1 scFv (VH+linker+VL)

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220
```

```
Asp Glu Leu Gly Ala Tyr Val Phe Gly Gly Gly Thr Lys Leu Thr Val
225                 230                 235                 240

Leu

<210> SEQ ID NO 78
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8 scFv, N3-8-1 scFv (VH+linker+VL)

<400> SEQUENCE: 78
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatgataata gtaatcggcc aagcggggtc cctgaccgat tctctggctc caagtctggc     600
acctcagcct ccctggccat cagtgggctc cagtccgagg atgaggctga ttattactgt     660
tcttctttta gtgatgagtt ggggggcttat gtcttcggcg aggcaccaa gctgacggtc     720 cta                                                                   723

<210> SEQ ID NO 79
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-2 scFv (VH+linker+VL)

<400> SEQUENCE: 79

Glu Val Gln Leu Leu Glu Ser Gly Gly Gly Leu Val Gln Pro Gly Gly
1                 5                  10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110
```

-continued

```
Thr Val Ser Ser Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Ser Asn Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu
```

```
<210> SEQ ID NO 80
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-2 scFv (VH+linker+VL)

<400> SEQUENCE: 80
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatagtaata atcagcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg gaggcaccaa gctgacggtc     720
cta                                                                   723
```

```
<210> SEQ ID NO 81
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-3 scFv (VH+linker+VL)

<400> SEQUENCE: 81

Glu Val Gln Leu Leu Glu Ser Gly Gly Gly Leu Val Gln Pro Gly Gly
```

-continued

```
1               5               10              15

Ser Leu Arg Leu Ser Cys Ala Ala Ser Gly Phe Thr Phe Ser Ser Tyr
            20              25              30

Asp Met Ser Trp Val Arg Gln Ala Pro Gly Lys Gly Leu Glu Trp Val
            35              40              45

Ser Ala Ile Ser Pro Tyr Ser Gly Arg Ile Tyr Tyr Ala Asp Ser Val
            50              55              60

Lys Gly Arg Phe Thr Ile Ser Arg Asp Asn Ser Lys Asn Thr Leu Tyr
65                  70              75              80

Leu Gln Met Asn Ser Leu Arg Ala Glu Asp Thr Ala Val Tyr Tyr Cys
                85              90              95

Ala Arg Met Ala Leu Asp Phe Asp Tyr Trp Gly Gln Gly Thr Leu Val
            100             105             110

Thr Val Ser Ser Gly Gly Gly Gly Ser Gly Gly Gly Ser Gly Gly
            115             120             125

Gly Gly Ser Gln Ser Val Leu Thr Gln Pro Pro Ser Ala Ser Gly Thr
        130             135             140

Pro Gly Gln Arg Val Thr Ile Ser Cys Thr Gly Ser Ser Ser Asn Ile
145             150             155             160

Gly Ser Asn Tyr Val Thr Trp Tyr Gln Gln Leu Pro Gly Thr Ala Pro
                165             170             175

Lys Leu Leu Ile Tyr Arg Asn Asn Gln Arg Pro Ser Gly Val Pro Asp
            180             185             190

Arg Phe Ser Gly Ser Lys Ser Gly Thr Ser Ala Ser Leu Ala Ile Ser
            195             200             205

Gly Leu Gln Ser Glu Asp Glu Ala Asp Tyr Tyr Cys Ser Ser Phe Ser
        210             215             220

Asp Glu Leu Gly Ala Tyr Val Phe Gly Gly Gly Thr Lys Leu Thr Val
225             230             235             240

Leu
```

```
<210> SEQ ID NO 82
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-3 scFv (VH+linker+VL)

<400> SEQUENCE: 82
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatcggaata atcagcggcc aagcggggtc cctgaccgat tctctggctc caagtctggc     600
```
acctcagcct ccctggccat cagtgggctc cagtccgagg atgaggctga ttattactgt     660
tcttctttta gtgatgagtt gggggcttat gtcttcggcg gaggcaccaa gctgacggtc     720
cta                                                                    723

<210> SEQ ID NO 83
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-4 scFv (VH+linker+VL)

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Asp Asn Ser Asn Arg Pro Ser Gly Val Pro Asp
            180                 185                 190

Arg Phe Ser Gly Ser Lys Ser Gly Thr Ser Ala Ser Leu Ala Ile Ser
            195                 200                 205

Gly Leu Gln Ser Glu Asp Glu Ala Asp Tyr Tyr Cys Ser Ser Phe Ser
    210                 215                 220

Asp Glu Leu Gly Ala Tyr Val Phe Gly Gly Gly Thr Lys Leu Thr Val
225                 230                 235                 240

Leu

<210> SEQ ID NO 84
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-4 scFv (VH+linker+VL)

<400> SEQUENCE: 84

-continued

```
gaggtgcagc tgttggagtc tggggggaggc ttggtacagc ctgggggggtc cctgagactc     60 tcctgtgcag cctctggatt caccttagc agttatgata tgagctgggt ccgccaggct    120
ccagggaagg ggctggagtg ggtctcagcg atctctccgt attcgggtag gatttattac    180
gctgattctg taaaaggtcg gttcaccatc tccagagaca attccaagaa cacgctgtat    240
ctgcaaatga acagcctgag agccgaggac acggccgtgt attactgtgc gagactggcg    300
cttgatttcg actactgggg ccagggtaca ctggtcaccg tgagctcagg tggaggcggt    360
tcaggcggag gtggatccgg cggtggcgga tcgcagtctg tgctgactca gccaccctca    420
gcgtctggga cccccgggca gagggtcacc atctcttgta ctggctcttc atctaatatt    480
ggcagtaatt atgtcacctg gtaccagcag ctcccaggaa cggcccccaa actcctcatc    540
tatgataata gtaatcggcc aagcggggtc cctgaccgat tctctggctc caagtctggc    600
acctcagcct ccctggccat cagtgggctc cagtccgagg atgaggctga ttattactgt    660 tcttcttta gtgatgagtt gggggcttat gtcttcggcg aggcaccaa gctgacggtc    720 cta                                                                  723
```

<210> SEQ ID NO 85
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-5 scFv (VH+linker+VL)

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Tyr Val Thr Trp Tyr Gln Gln Leu Pro Gly Thr Ala Pro
                165                 170                 175

Lys Leu Leu Ile Tyr Ser Asn Asn Gln Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Ser Ser Phe Ser
```

-continued

```
        210              215              220

Asp Glu Leu Gly Ala Tyr Val Phe Gly Gly Gly Thr Lys Leu Thr Val
225                 230              235              240

Leu

<210> SEQ ID NO 86
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-5 scFv (VH+linker+VL)

<400> SEQUENCE: 86
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggcccccaa actcctcatc     540
tatagtaata tcagcggcc aagcggggtc cctgaccgat tctctggctc caagtctggc     600
acctcagcct ccctggccat cagtgggctc cagtccgagg atgaggctga ttattactgt     660
tcttctttta gtgatgagtt gggggcttat gtcttcggcg gaggcaccaa gctgacggtc     720
cta                                                                    723

<210> SEQ ID NO 87
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3-8-6 scFv (VH+linker+VL)

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110
```

```
Thr Val Ser Ser Gly Gly Gly Ser Gly Gly Gly Gly Ser Gly Gly
        115             120             125

Gly Gly Ser Gln Ser Val Leu Thr Gln Pro Pro Ser Ala Ser Gly Thr
    130             135             140

Pro Gly Gln Arg Val Thr Ile Ser Cys Thr Gly Ser Ser Ser Asn Ile
145             150             155             160

Gly Ser Asn Tyr Val Thr Trp Tyr Gln Gln Leu Pro Gly Thr Ala Pro
            165             170             175

Lys Leu Leu Ile Tyr Arg Asn Asn Gln Arg Pro Ser Gly Val Pro Asp
        180             185             190

Arg Phe Ser Gly Ser Lys Ser Gly Thr Ser Ala Ser Leu Ala Ile Ser
        195             200             205

Gly Leu Gln Ser Glu Asp Glu Ala Asp Tyr Tyr Cys Ser Ser Phe Ser
    210             215             220

Asp Glu Leu Gly Ala Tyr Val Phe Gly Gly Gly Thr Lys Leu Thr Val
225             230             235             240

Leu
```

```
<210> SEQ ID NO 88
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3-8-6 scFv (VH+linker+VL)

<400> SEQUENCE: 88
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagg tggaggcggt     360
tcaggcggag gtggatccgg cggtggcgga tcgcagtctg tgctgactca gccaccctca     420
gcgtctggga cccccgggca gagggtcacc atctcttgta ctggctcttc atctaatatt     480
ggcagtaatt atgtcacctg gtaccagcag ctcccaggaa cggccccaa actcctcatc      540 tatcggaata atcagcggcc aagcggggtc cctgaccgat tctctggctc caagtctggc     600
acctcagcct ccctggccat cagtgggctc cagtccgagg atgaggctga ttattactgt     660
tcttctttta gtgatgagtt ggggggcttat gtcttcggcg gaggcaccaa gctgacggtc     720
cta                                                                   723
```

```
<210> SEQ ID NO 89
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 IgG heavy chain

<400> SEQUENCE: 89
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Tyr Asp Asn Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
```

-continued

```
                      420             425             430
Asn His Tyr Thr Gln Lys Ser Leu Ser Leu Ser Pro Gly Lys
        435             440             445

<210> SEQ ID NO 90
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 IgG heavy chain

<400> SEQUENCE: 90
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338

<210> SEQ ID NO 91
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N3 IgG light chain

<400> SEQUENCE: 91

Gln Ser Val Leu Thr Gln Pro Pro Ser Ala Ser Gly Thr Pro Gly Gln
1               5                   10                  15
```

```
Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
            35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ser Trp Asp Asp Ser Leu
                85                  90                  95

Ser Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

```
<210> SEQ ID NO 92
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: N3 IgG light chain

<400> SEQUENCE: 92
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta tcggccaag cggggtccct      180 gaccgattct ctggctccaa gtctggcacc tcagcctccc tggccatcag tgggctccgg     240
tccgaggatg aggctgatta ttactgtgct tcttgggatg atagcctgag tgcttatgtc     300
ttcggcggag gcaccaagct gacggtccta cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t               651
```

```
<210> SEQ ID NO 93
<211> LENGTH: 446
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly

```
            370                 375                 380
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

<210> SEQ ID NO 94
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1

<400> SEQUENCE: 94

```
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720 ctcttcccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

<210> SEQ ID NO 95
<211> LENGTH: 446
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<223> OTHER INFORMATION: IgG heavy chain 2

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

-continued

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 96
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2

<400> SEQUENCE: 96
gaggtgcagc tgttggagtc tgggggaggc ttggtacagc ctggggggtc cctgagactc        60
tcctgtgcag cctctggatt cacctttagc agttatgata tgagctgggt ccgccaggct       120
ccagggaagg ggctggagtg ggtctcagcg atctcgccgc agatgggtcg ggtgtattac       180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctcagc ctccaccaag       360
ggcccatcgg tcttcccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaactcc tggggggacc gtcagtcttc       720 ctcttcccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cacgtaccgt       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtaccctg ccccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                   1338

<210> SEQ ID NO 97
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<220> FEATURE:
<223> OTHER INFORMATION: IgG heavy chain 3

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Asp Pro Leu Gly Gly Asn Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400
```

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 98
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 3

<400> SEQUENCE: 98
gaggtgcagc tgttggagtc tgggggaggc ttggtacagc ctgggggtc cctgagactc        60 tcctgtgcag cctctggatt caccttttagc agttatgata tgagctgggt ccgccaggct      120
ccagggaagg ggctggagtg ggtctcagcg atcgatccgt tggggggtaa tatttattac      180
gctgattctg taaaaggtcg gttcaccatc tccagagaca attccaagaa cacgctgtat      240
ctgcaaatga acagcctgag agccgaggac acggccgtgt attactgtgc gagaatggcg      300
cttgatttcg actactgggg ccagggtaca ctggtcaccg tgagctcagc ctccaccaag      360
ggcccatcgg tcttcccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaactcc tggggggacc gtcagtcttc      720 ctcttcccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtacaccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                    1338

<210> SEQ ID NO 99
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4

-continued

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
            85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp

-continued

```
                 405              410              415
Gln Gln Gly Asn Val Phe Ser Cys Ser Val Met His Glu Ala Leu His
            420              425              430

Asn His Tyr Thr Gln Lys Ser Leu Ser Leu Ser Pro Gly Lys
        435              440              445

<210> SEQ ID NO 100
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4

<400> SEQUENCE: 100
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338

<210> SEQ ID NO 101
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5

<400> SEQUENCE: 101
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

```
Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 102
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5

<400> SEQUENCE: 102
gaggtgcagc tgttggagtc tggggggggc ttggtacagc ctggggggtc cctgagactc      60
tcctgtgcag cctctggatt caccttagc agttatgata tgagctgggt ccgccaggct      120
ccagggaagg ggctggagtg ggtctcagcg atcgggggctg atgggggtcc gtcttattac      180
gctgattctg taaaaggtcg gttcaccatc tccagagaca attccaagaa cacgctgtat      240
ctgcaaatga acagcctgag agccgaggac acggccgtgt attactgtgc gagaatggcg      300
cttgatttcg actactgggg ccagggtaca ctggtcaccg tgagctcagc ctccaccaag      360
ggcccatcgg tcttcccc ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaactcc tggggggacc gtcagtcttc      720 ctcttcccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg      1020
cagccccgag aaccacaggt gtacaccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                  1338

<210> SEQ ID NO 103
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6

<400> SEQUENCE: 103

Glu Val Gln Leu Leu Glu Ser Gly Gly Gly Leu Val Gln Pro Gly Gly
```

-continued

```
1                5                    10                    15

Ser Leu Arg Leu Ser Cys Ala Ala Ser Gly Phe Thr Phe Ser Ser Tyr
             20               25               30

Asp Met Ser Trp Val Arg Gln Ala Pro Gly Lys Gly Leu Glu Trp Val
             35               40               45

Ser Ala Ile Ser Pro Tyr Ser Gly Arg Ile Tyr Tyr Ala Asp Ser Val
         50                   55               60

Lys Gly Arg Phe Thr Ile Ser Arg Asp Asn Ser Lys Asn Thr Leu Tyr
65                   70               75                   80

Leu Gln Met Asn Ser Leu Arg Ala Glu Asp Thr Ala Val Tyr Tyr Cys
             85               90               95

Ala Arg Met Ala Leu Asp Phe Asp Tyr Trp Gly Gln Gly Thr Leu Val
             100              105              110

Thr Val Ser Ser Ala Ser Thr Lys Gly Pro Ser Val Phe Pro Leu Ala
             115              120              125

Pro Ser Ser Lys Ser Thr Ser Gly Gly Thr Ala Ala Leu Gly Cys Leu
             130              135              140

Val Lys Asp Tyr Phe Pro Glu Pro Val Thr Val Ser Trp Asn Ser Gly
145              150              155              160

Ala Leu Thr Ser Gly Val His Thr Phe Pro Ala Val Leu Gln Ser Ser
             165              170              175

Gly Leu Tyr Ser Leu Ser Ser Val Val Thr Val Pro Ser Ser Ser Leu
             180              185              190

Gly Thr Gln Thr Tyr Ile Cys Asn Val Asn His Lys Pro Ser Asn Thr
             195              200              205

Lys Val Asp Lys Lys Val Glu Pro Lys Ser Cys Asp Lys Thr His Thr
             210              215              220

Cys Pro Pro Cys Pro Ala Pro Glu Leu Leu Gly Gly Pro Ser Val Phe
225              230              235              240

Leu Phe Pro Pro Lys Pro Lys Asp Thr Leu Met Ile Ser Arg Thr Pro
             245              250              255

Glu Val Thr Cys Val Val Val Asp Val Ser His Glu Asp Pro Glu Val
             260              265              270

Lys Phe Asn Trp Tyr Val Asp Gly Val Glu Val His Asn Ala Lys Thr
             275              280              285

Lys Pro Arg Glu Glu Gln Tyr Asn Ser Thr Tyr Arg Val Val Ser Val
             290              295              300

Leu Thr Val Leu His Gln Asp Trp Leu Asn Gly Lys Glu Tyr Lys Cys
305              310              315              320

Lys Val Ser Asn Lys Ala Leu Pro Ala Pro Ile Glu Lys Thr Ile Ser
             325              330              335

Lys Ala Lys Gly Gln Pro Arg Glu Pro Gln Val Tyr Thr Leu Pro Pro
             340              345              350

Ser Arg Asp Glu Leu Thr Lys Asn Gln Val Ser Leu Thr Cys Leu Val
             355              360              365

Lys Gly Phe Tyr Pro Ser Asp Ile Ala Val Glu Trp Glu Ser Asn Gly
             370              375              380

Gln Pro Glu Asn Asn Tyr Lys Thr Thr Pro Pro Val Leu Asp Ser Asp
385              390              395              400

Gly Ser Phe Phe Leu Tyr Ser Lys Leu Thr Val Asp Lys Ser Arg Trp
             405              410              415

Gln Gln Gly Asn Val Phe Ser Cys Ser Val Met His Glu Ala Leu His
             420              425              430
```

Asn His Tyr Thr Gln Lys Ser Leu Ser Leu Ser Pro Gly Lys
        435                 440                 445

<210> SEQ ID NO 104
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6

<400> SEQUENCE: 104
gaggtgcagc tgttggagtc tggggggaggc ttggtacagc ctgggggtc cctgagactc      60 tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc tccaccaag     360 ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720 ctcttcccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                 1338

<210> SEQ ID NO 105
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7

<400> SEQUENCE: 105

Glu Val Gln Leu Leu Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Ser Tyr
          20                  25                  30

Asp Met Ser Trp Val Arg Gln Ala Pro Gly Lys Gly Leu Glu Trp Val
          35                  40                  45

Ser Ala Ile Ser Pro Tyr Ser Gly Arg Ile Tyr Tyr Ala Asp Ser Val
          50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                  85                  90                  95

Ala Arg Leu Ala Leu Asp Phe Asp Tyr Trp Gly Gln Gly Thr Leu Val
              100                 105                 110

Thr Val Ser Ser Ala Ser Thr Lys Gly Pro Ser Val Phe Pro Leu Ala
              115                 120                 125

Pro Ser Ser Lys Ser Thr Ser Gly Gly Thr Ala Ala Leu Gly Cys Leu
          130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                  165                 170                 175

Gly Leu Tyr Ser Leu Ser Ser Val Val Thr Val Pro Ser Ser Ser Leu
                  180                 185                 190

Gly Thr Gln Thr Tyr Ile Cys Asn Val Asn His Lys Pro Ser Asn Thr
              195                 200                 205

Lys Val Asp Lys Lys Val Glu Pro Lys Ser Cys Asp Lys Thr His Thr
          210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                  245                 250                 255

Glu Val Thr Cys Val Val Val Asp Val Ser His Glu Asp Pro Glu Val
              260                 265                 270

Lys Phe Asn Trp Tyr Val Asp Gly Val Glu Val His Asn Ala Lys Thr
              275                 280                 285

Lys Pro Arg Glu Glu Gln Tyr Asn Ser Thr Tyr Arg Val Val Ser Val
          290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                  325                 330                 335

Lys Ala Lys Gly Gln Pro Arg Glu Pro Gln Val Tyr Thr Leu Pro Pro
              340                 345                 350

Ser Arg Asp Glu Leu Thr Lys Asn Gln Val Ser Leu Thr Cys Leu Val
              355                 360                 365

Lys Gly Phe Tyr Pro Ser Asp Ile Ala Val Glu Trp Glu Ser Asn Gly
          370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                  405                 410                 415

Gln Gln Gly Asn Val Phe Ser Cys Ser Val Met His Glu Ala Leu His
              420                 425                 430

Asn His Tyr Thr Gln Lys Ser Leu Ser Leu Ser Pro Gly Lys
```

-continued 435                    440                    445

<210> SEQ ID NO 106
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7

<400> SEQUENCE: 106
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagcccccc atcgagaaaa ccatctccaa agccaaaggg    1020
cagccccgag aaccacaggt gtatacctg ccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcagggaac    1260 gtcttctcat gctccgtgat gcatgaggct ctgcacaacc actacacgca gaagagcctc    1320
tccctgtccc cgggtaaa                                                  1338

<210> SEQ ID NO 107
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 1

<400> SEQUENCE: 107

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

```
Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Phe Ser Asp Glu Leu
                85                  90                  95

Gly Ala Tyr Val Phe Gly Gly Gly Thr Lys Leu Thr Val Leu Arg Thr
                100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 108
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 1

<400> SEQUENCE: 108
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat gataatagta atcggccaag cggggtccct     180
gaccgattct ctggctccaa gtctggcacc tcagcctccc tggccatcag tgggctccag     240
tccgaggatg aggctgatta ttactgtgct tcttttagtg atgagttggg ggcttatgtc     300
ttcggcggag gcaccaagct gacggtccta cgtacggtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg t             651
```

```
<210> SEQ ID NO 109
<211> LENGTH: 217
<212> TYPE: PRT
<213> ORGANISM: Artificial Sequence
<220> FEATURE:
<223> OTHER INFORMATION: Description of Artificial Sequence: Synthetic
```

```
         polypeptide
<220> FEATURE:
<223> OTHER INFORMATION: IgG light chain 2

<400> SEQUENCE: 109

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215

<210> SEQ ID NO 110
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 2

<400> SEQUENCE: 110
cagtctgtgc tgactcagcc accctcagcg tctgggaccc ccgggcagag ggtcaccatc     60
tcttgtactg gctcttcatc taatattggc agtaattatg tcacctggta ccagcagctc    120
ccaggaacgg cccccaaact cctcatctat gataatagta tcggccaag cggggtccct     180 gaccgattct ctggctccaa gtctggcacc tcagcctccc tggccatcag tgggctccag    240
tccgaggatg aggctgatta ttactgttct ctttttagtg atgagttggg ggcttatgtc    300
ttcggcggag gcaccaagct gacggtccta cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
```
accctgacgc tgagcaaagc agactacgag aaacacaaag tctacgcctg cgaagtcacc        600
catcagggcc tgagctcgcc cgtcacaaag agcttcaaca gggggagagtg t               651

<210> SEQ ID NO 111
<211> LENGTH: 216
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: IgG light chain 3

<400> SEQUENCE: 111

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Asp Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 112
<211> LENGTH: 648
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: IgG light chain 3

<400> SEQUENCE: 112
cagtctgtgc tgactcagcc accctcagcg tctgggaccc ccgggcagag ggtcaccatc        60
tcttgtactg gctcttcatc taatattggc agtaattatg tcacctggta ccagcagctc        120
ccaggaacgg cccccaaact cctcatctat gataatagta atcggccaag cggggtccct        180
gaccgattct ctggctccaa gtctggcacc tcagcctccc tggccatcag tgggctccag        240

```
tccgaggatg aggctgatta ttactgttct tcttttagtg atgagttggg ggcttatgtc        300
ttcggcggag gcaccaagct gacggtccta ggtcagccca aggctgcccc ctcggtcacg        360
ctcttcccac cctcctctga ggagcttcaa gccaacaagg ccacactggt gtgtctcata        420
agtgacttct acccgggagc cgtgacagtg gcctggaagg cagatagcag ccccgtcaag        480
gcgggagtgg agaccaccac accctccaaa caaagcaaca acaagtacgc ggccagcagc        540
tacctgagcc tgacgcctga gcagtggaag tcccacagaa gctacagctg ccaggtcacg        600
catgaaggga gcaccgtgga gaagacagtg gcccctacag aatgctct                     648
```

<210> SEQ ID NO 113
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 4

<400> SEQUENCE: 113

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 114
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: IgG light chain 4

<400> SEQUENCE: 114

```
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat agtaataatc agcggccaag cggggtccct     180
gaccgattct ctggctccaa gtctggcacc tcagcctccc tggccatcag tgggctccag     240
tccgaggatg aggctgatta ttactgttct tcttttagtg atgagttggg ggcttatgtc     300
ttcggcggag gcaccaagct gacggtccta agtcagccca aggctgcccc ctcggtcacg     360
ctcttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac acctccaaa caaagcaaca acaagtacgc ggccagcagc     540
tacctgagcc tgacgcctga gcagtggaag tcccacagaa gctacagctg ccaggtcacg     600
catgaaggga gcaccgtgga gaagacagtg gcccctacag aatgctct                 648
```

```
<210> SEQ ID NO 115
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG light chain 5
```

<400> SEQUENCE: 115

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Tyr Val Thr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ser Phe Ser Asp Glu Leu
                85                  90                  95

Gly Ala Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
```

-continued

```
        210             215
```

```
<210> SEQ ID NO 116
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG light chain 5

<400> SEQUENCE: 116
cagtctgtgc tgactcagcc accctcagcg tctgggaccc ccgggcagag ggtcaccatc      60
tcttgtactg gctcttcatc taatattggc agtaattatg tcacctggta ccagcagctc     120
ccaggaacgg cccccaaact cctcatctat cggaataatc agcggccaag cggggtccct     180
gaccgattct ctggctccaa gtctggcacc tcagcctccc tggccatcag tgggctccag     240
tccgaggatg aggctgatta ttactgttct tcttttagtg atgagttggg ggcttatgtc     300
ttcggcggag gcaccaagct gacggtccta ggtcagccca aggctgcccc ctcggtcacg     360
ctcttcccac cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac acctccaaaa caaagcaaca caagtacgc ggccagcagc     540 tacctgagcc tgacgcctga gcagtggaag tcccacagaa gctacagctg ccaggtcacg     600
catgaaggga gcaccgtgga agacagtg gcccctacag aatgctct                   648

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: KRS epitope F4

<400> SEQUENCE: 117

Glu Pro Lys Leu Ser Lys Asn Glu Leu Lys Arg Arg Leu Lys Ala Glu
1               5                   10                  15

Lys Lys Val Ala Glu Lys Glu Ala Lys Gln Lys Glu
            20                  25

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR H2 mutant 5 amino acid

<400> SEQUENCE: 118

Val Ile Ser Ser Asp Gly Gly Asn Thr Tyr Tyr Ala Asp Ser Val Lys
1               5                   10                  15

Gly

<210> SEQ ID NO 119
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: CDR H2 mutant 5 DNA

<400> SEQUENCE: 119
gtgatctctt ctgatggtgg taatacatat tacgctgatt ctgtaaaagg t              51

<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain constant region ver.1_amino acid

<400> SEQUENCE: 120

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 121
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: light chain constant region ver.1_DNA

<400> SEQUENCE: 121
cgtacggtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg t                                                 321

<210> SEQ ID NO 122
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain constant region ver.2_amino acid
```

<400> SEQUENCE: 122

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
        50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 123
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: light chain constant region ver.2_DNA

<400> SEQUENCE: 123
ggtcagccca aggctgcccc ctcggtcacg ctcttccac cctcctctga ggagcttcaa        60
gccaacaagg ccacactggt gtgtctcata agtgacttct acccgggagc cgtgacagtg       120
gcctggaagg cagatagcag ccccgtcaag gcgggagtgg agaccaccac accctccaaa       180
caaagcaaca acaagtacgc ggccagcagc tacctgagcc tgacgcctga gcagtggaag       240
tcccacagaa gctacagctg ccaggtcacg catgaaggga gcaccgtgga agacagtg        300 gccctacag aatgctct                                                    318

<210> SEQ ID NO 124
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      wild type amino acid

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
              85              90              95
Lys Val Glu Pro Lys Ser Cys Asp Lys Thr His Thr Cys Pro Pro Cys
             100             105             110

Pro Ala Pro Glu Leu Leu Gly Gly Pro Ser Val Phe Leu Phe Pro Pro
             115             120             125

Lys Pro Lys Asp Thr Leu Met Ile Ser Arg Thr Pro Glu Val Thr Cys
             130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
             165             170             175

Glu Gln Tyr Asn Ser Thr Tyr Arg Val Val Ser Val Leu Thr Val Leu
             180             185             190

His Gln Asp Trp Leu Asn Gly Lys Glu Tyr Lys Cys Lys Val Ser Asn
             195             200             205

Lys Ala Leu Pro Ala Pro Ile Glu Lys Thr Ile Ser Lys Ala Lys Gly
             210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
             245             250             255

Pro Ser Asp Ile Ala Val Glu Trp Glu Ser Asn Gly Gln Pro Glu Asn
             260             265             270

Asn Tyr Lys Thr Thr Pro Pro Val Leu Asp Ser Asp Gly Ser Phe Phe
             275             280             285

Leu Tyr Ser Lys Leu Thr Val Asp Lys Ser Arg Trp Gln Gln Gly Asn
             290             295             300

Val Phe Ser Cys Ser Val Met His Glu Ala Leu His Asn His Tyr Thr
305             310             315             320

Gln Lys Ser Leu Ser Leu Ser Pro Gly Lys
             325             330
```

<210> SEQ ID NO 125
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      wild type_DNA

<400> SEQUENCE: 125

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
```

```
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtataccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                       990
```

<210> SEQ ID NO 126
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      mutant TA amino acid

<400> SEQUENCE: 126

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Ala Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

-continued

```
                    260             265             270
Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330
```

```
<210> SEQ ID NO 127
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      mutant TA_DNA

<400> SEQUENCE: 127
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga     360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcgcctacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtataccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc ccggggtaaa                                      990
```

```
<210> SEQ ID NO 128
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      mutant LALA_amino acid

<400> SEQUENCE: 128

Ala Ser Thr Lys Gly Pro Ser Val Phe Pro Leu Ala Pro Ser Ser Lys
1               5               10              15
```

-continued

```
Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 129
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      mutant LALA_DNA

<400> SEQUENCE: 129
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
```

-continued

```
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaagc cgccgggggga     360 ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtataccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                       990
```

<210> SEQ ID NO 130
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      mutant LALATA_amino acid

<400> SEQUENCE: 130

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Ala Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 131
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      mutant LALATA_DNA

<400> SEQUENCE: 131

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc cgccggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcgcctacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag gcagccccg agaaccacag gtgtataccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                       990
```

<210> SEQ ID NO 132
<211> LENGTH: 330
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      mutant LALAPG_amino acid

<400> SEQUENCE: 132

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 133
<211> LENGTH: 990
<212> TYPE: DNA
<213> ORGANISM: Artificial Sequence
<220> FEATURE:

-continued

<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      mutant LALAPG_DNA

<400> SEQUENCE: 133

```
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagaa agttgagccc       300
aaatcttgtg acaaaactca cacatgccca ccgtgcccag cacctgaagc cgccggggga       360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacaac       540
agcacgtacc gtgtggtcag cgtcctcacc gtcctgcacc aggactggct gaatggcaag       600
gagtacaagt gcaaggtctc caacaaagcc ctcggcgccc catcgagaa aaccatctcc       660 aaagccaaag gcagccccg agaaccacag gtgtataccc tgcccccatc ccgggatgag       720
ctgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900
cagcagggga acgtcttctc atgctccgtg atgcatgagg ctctgcacaa ccactacacg       960
cagaagagcc tctccctgtc cccgggtaaa                                        990
```

<210> SEQ ID NO 134
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG1
      mutant LALAPGTA_amino acid

<400> SEQUENCE: 134

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Ala Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 135
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG1
      mutant LALAPGTA_DNA

<400> SEQUENCE: 135
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaagc cgccggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcgcctacc gtgtggtcag cgtcctcacc gtcctgcacc aggactggct gaatggcaag     600
gagtacaagt gcaaggtctc caacaaagcc ctcggcgccc ccatcgagaa aaccatctcc     660
aaagccaaag gcagccccg agaaccacag gtgtataccc tgcccccatc ccgggatgag     720
ctgaccaaga accaggtcag cctgacctgc ctggtcaaag gcttctatcc cagcgacatc     780
```

```
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc cccgggtaaa                                       990
```

```
<210> SEQ ID NO 136
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG4
      wild type amino acid

<400> SEQUENCE: 136

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
    290                 295                 300
```

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 137
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG4
      wild type_DNA

<400> SEQUENCE: 137
gccagcacca agggcccttc cgtgtttccc ctggcccctt gctcccggtc cacatctgag      60
agcaccgccg ccctgggctg tctggtgaag gactacttcc cagagcccgt gaccgtgagc     120
tggaacagcg gcgccctgac aagcggcgtg cacacatttc cgccgtgct gcagagctcc      180 ggcctgtact ccctgtctag cgtggtgaca gtgccttcct ctagcctggg caccaagaca     240
tatacctgta acgtggacca caagcccagc aataccaagg tggataagcg ggtggagtct     300
aagtacggcc ctccttgccc tagctgtcct gctccagagt ttctgggcgg cccttccgtg     360
ttcctgtttc cacccaaacc aaaggacaca ctgatgatct ctagaacacc agaggtgacc     420
tgcgtggtgg tggacgtgag ccaggaggat cccgaggtgc agttcaactg gtacgtggat     480
ggcgtggagg tgcacaatgc caagaccaag ccaagagagg agcagtttaa ctctacatac     540
agggtggtga gcgtgctgac cgtgctgcac caggattggc tcaacggcaa ggagtataag     600
tgcaaggtgt ccaataaggg cctgccctcc tctatcgaga agacaatctc taaggctaag     660
ggccagccaa gagagcctca ggtgtacacc ctgcctccaa gccaggagga gatgacaaag     720
aaccaggtgt ccctgacatg tctggtgaag ggcttctatc cctccgacat cgccgtggag     780
tgggagtcta atggccagcc tgagaacaat tacaagacca cacccctgt gctggactct      840 gatggcagct ctttctgta ttccaggctg accgtggata agtctcggtg gcaggagggc      900
aacgtgttca gctgctctgt gatgcacgaa gccctgcata tcactatac tcagaaaagt      960 ctgtcactgt cactgggaaa g                                              981

<210> SEQ ID NO 138
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: heavy chain constant region(CH1, CH2, CH3)_IgG4
      mutant TA_amino acid

<400> SEQUENCE: 138

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser

```
              50                    55                    60

Leu Ser Ser Val Val Thr Val Pro Ser Ser Leu Gly Thr Lys Thr
65                  70                    75                    80

Tyr Thr Cys Asn Val Asp His Lys Pro Ser Asn Thr Lys Val Asp Lys
                85                    90                    95

Arg Val Glu Ser Lys Tyr Gly Pro Pro Cys Pro Ser Cys Pro Ala Pro
                100                   105                   110

Glu Phe Leu Gly Gly Pro Ser Val Phe Leu Phe Pro Pro Lys Pro Lys
            115                   120                   125

Asp Thr Leu Met Ile Ser Arg Thr Pro Glu Val Thr Cys Val Val Val
            130                   135                   140

Asp Val Ser Gln Glu Asp Pro Glu Val Gln Phe Asn Trp Tyr Val Asp
145                 150                   155                   160

Gly Val Glu Val His Asn Ala Lys Thr Lys Pro Arg Glu Glu Gln Phe
                165                   170                   175

Asn Ser Ala Tyr Arg Val Val Ser Val Leu Thr Val Leu His Gln Asp
                180                   185                   190

Trp Leu Asn Gly Lys Glu Tyr Lys Cys Lys Val Ser Asn Lys Gly Leu
                195                   200                   205

Pro Ser Ser Ile Glu Lys Thr Ile Ser Lys Ala Lys Gly Gln Pro Arg
        210                   215                   220

Glu Pro Gln Val Tyr Thr Leu Pro Pro Ser Gln Glu Glu Met Thr Lys
225                 230                   235                   240

Asn Gln Val Ser Leu Thr Cys Leu Val Lys Gly Phe Tyr Pro Ser Asp
                245                   250                   255

Ile Ala Val Glu Trp Glu Ser Asn Gly Gln Pro Glu Asn Asn Tyr Lys
                260                   265                   270

Thr Thr Pro Pro Val Leu Asp Ser Asp Gly Ser Phe Phe Leu Tyr Ser
                275                   280                   285

Arg Leu Thr Val Asp Lys Ser Arg Trp Gln Glu Gly Asn Val Phe Ser
        290                   295                   300

Cys Ser Val Met His Glu Ala Leu His Asn His Tyr Thr Gln Lys Ser
305                 310                   315                   320

Leu Ser Leu Ser Leu Gly Lys
                325
```

```
<210> SEQ ID NO 139
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: heavy chain constant region(CH1, CH2, CH3)_IgG4
      mutant TA_DNA

<400> SEQUENCE: 139
gccagcacca agggcccttc cgtgtttccc ctggcccctt gctcccggtc cacatctgag      60
agcaccgccg ccctgggctg tctggtgaag gactacttcc cagagcccgt gaccgtgagc     120
tggaacagcg gcgccctgac aagcggcgtg cacacatttc cgccgtgct gcagagctcc     180 ggcctgtact ccctgtctag cgtggtgaca gtgccttcct ctagcctggg caccaagaca     240
tatacctgta acgtggacca caagccaagc aataccaagg tggataagcg ggtggagtct     300
aagtacggcc ctccttgccc tagctgtcct gctccagagt ttctgggcgg cccttccgtg     360
```

-continued

```
ttcctgtttc cacccaaacc aaaggacaca ctgatgatct ctagaacacc agaggtgacc   420
tgcgtggtgg tggacgtgag ccaggaggat cccgaggtgc agttcaactg gtacgtggat   480
ggcgtggagg tgcacaatgc caagaccaag ccaagagagg agcagtttaa ctctgcctac   540
agggtggtga gcgtgctgac cgtgctgcac caggattggc tcaacggcaa ggagtataag   600
tgcaaggtgt ccaataaggg cctgccctcc tctatcgaga agacaatctc taaggctaag   660
ggccagccaa gagagcctca ggtgtacacc ctgcctccaa gccaggagga gatgacaaag   720
aaccaggtgt ccctgacatg tctggtgaag ggcttctatc cctccgacat cgccgtggag   780
tgggagtcta atggccagcc tgagaacaat tacaagacca cacccctgt gctggactct   840 gatggcagct ctttctgta ttccaggctg accgtggata agtctcggtg gcaggagggc   900
aacgtgttca gctgctctgt gatgcacgaa gccctgcata tcactatac tcagaaaagt   960 ctgtcactgt cactgggaaa g                                             981
```

<210> SEQ ID NO 140
<211> LENGTH: 446
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: IgG heavy chain_IgG1 mutant TA_amino acid

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Tyr Asp Asn Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 141
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG1 mutant TA_DNA

<400> SEQUENCE: 141
gaggtgcagc tgttggagtc tgggggaggc ttggtacagc ctgggggggtc cctgagactc      60 tcctgtgcag cctctggatt cacctttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
```

```
gtggtggtgg acgtgagcca cgaagaccct gaggtcaagt tcaactggta cgtggacggc        840
gtggaggtgc ataatgccaa gacaaagccg cgggaggagc agtacaacag cgcctaccgt        900
gtggtcagcg tcctcaccgt cctgcaccag gactggctga atggcaagga gtacaagtgc        960
aaggtctcca acaaagccct cccagccccc atcgagaaaa ccatctccaa agccaaaggg       1020
cagccccgag aaccacaggt gtataccctg cccccatccc gggatgagct gaccaagaac       1080
caggtcagcc tgacctgcct ggtcaaaggc ttctatccca gcgacatcgc cgtggagtgg       1140
gagagcaatg ggcagccgga gaacaactac aagaccacgc ctcccgtgct ggactccgac       1200
ggctccttct tcctctacag caagctcacc gtggacaaga gcaggtggca gcaggggaac       1260
gtcttctcat gctccgtgat gcatgaggct ctgcacaacc actacacgca gaagagcctc       1320
tccctgtccc cgggtaaa                                                      1338
```

```
<210> SEQ ID NO 142
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG1 mutant LALA_amino acid

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
            85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
```

-continued

```
               245              250              255
Glu Val Thr Cys Val Val Val Asp Val Ser His Glu Asp Pro Glu Val
            260              265              270
Lys Phe Asn Trp Tyr Val Asp Gly Val Glu Val His Asn Ala Lys Thr
            275              280              285
Lys Pro Arg Glu Glu Gln Tyr Asn Ser Thr Tyr Arg Val Val Ser Val
        290              295              300
Leu Thr Val Leu His Gln Asp Trp Leu Asn Gly Lys Glu Tyr Lys Cys
305              310              315              320
Lys Val Ser Asn Lys Ala Leu Pro Ala Pro Ile Glu Lys Thr Ile Ser
            325              330              335
Lys Ala Lys Gly Gln Pro Arg Glu Pro Gln Val Tyr Thr Leu Pro Pro
            340              345              350
Ser Arg Asp Glu Leu Thr Lys Asn Gln Val Ser Leu Thr Cys Leu Val
        355              360              365
Lys Gly Phe Tyr Pro Ser Asp Ile Ala Val Glu Trp Glu Ser Asn Gly
    370              375              380
Gln Pro Glu Asn Asn Tyr Lys Thr Thr Pro Pro Val Leu Asp Ser Asp
385              390              395              400
Gly Ser Phe Phe Leu Tyr Ser Lys Leu Thr Val Asp Lys Ser Arg Trp
            405              410              415
Gln Gln Gly Asn Val Phe Ser Cys Ser Val Met His Glu Ala Leu His
        420              425              430
Asn His Tyr Thr Gln Lys Ser Leu Ser Leu Ser Pro Gly Lys
        435              440              445
```

```
<210> SEQ ID NO 143
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG1 mutant LALA_DNA

<400> SEQUENCE: 143
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
```

-continued

```
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtatacctg ccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                1338
```

```
<210> SEQ ID NO 144
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG1 mutant LALATA_amino acid

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
        260             265             270
```

```
Lys Phe Asn Trp Tyr Val Asp Gly Val Glu Val His Asn Ala Lys Thr
        275             280             285
```

```
Lys Pro Arg Glu Glu Gln Tyr Asn Ser Ala Tyr Arg Val Val Ser Val
        290             295             300
```

```
Leu Thr Val Leu His Gln Asp Trp Leu Asn Gly Lys Glu Tyr Lys Cys
305             310             315             320
```

```
Lys Val Ser Asn Lys Ala Leu Pro Ala Pro Ile Glu Lys Thr Ile Ser
            325             330             335
```

```
Lys Ala Lys Gly Gln Pro Arg Glu Pro Gln Val Tyr Thr Leu Pro Pro
            340             345             350
```

```
Ser Arg Asp Glu Leu Thr Lys Asn Gln Val Ser Leu Thr Cys Leu Val
            355             360             365
```

```
Lys Gly Phe Tyr Pro Ser Asp Ile Ala Val Glu Trp Glu Ser Asn Gly
    370             375             380
```

```
Gln Pro Glu Asn Asn Tyr Lys Thr Thr Pro Pro Val Leu Asp Ser Asp
385             390             395             400
```

```
Gly Ser Phe Phe Leu Tyr Ser Lys Leu Thr Val Asp Lys Ser Arg Trp
            405             410             415
```

```
Gln Gln Gly Asn Val Phe Ser Cys Ser Val Met His Glu Ala Leu His
            420             425             430
```

```
Asn His Tyr Thr Gln Lys Ser Leu Ser Leu Ser Pro Gly Lys
            435             440             445
```

```
<210> SEQ ID NO 145
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG1 mutant LALATA_DNA

<400> SEQUENCE: 145
gaggtgcagc tgttggagtc tggggggaggc ttggtacagc ctgggggggtc cctgagactc        60 tcctgtgcag cctctggatt caccttttagc agttatgata tgagctgggt ccgccaggct       120
ccagggaagg ggctggagtg ggtctcagcg atctcttatg ataatggtaa tacatattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctcagc ctccaccaag       360
ggcccatcgg tcttcccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaagccg ccgggggacc gtcagtcttc       720 ctcttcccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cgcctaccgt       900
```

-continued

```
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtataccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338
```

```
<210> SEQ ID NO 146
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG1 mutant LALAPG_amino acid

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 147
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG1 mutant LALAPG_DNA

<400> SEQUENCE: 147
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960

```
aaggtctcca acaaagccct cggcgccccc atcgagaaaa ccatctccaa agccaaaggg      1020
cagccccgag aaccacaggt gtataccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338

<210> SEQ ID NO 148
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG1 mutant LALAPGTA_amino acid

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
```

```
              275                 280                 285
Lys Pro Arg Glu Glu Gln Tyr Asn Ser Ala Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Gly Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445
```

<210> SEQ ID NO 149
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG1 mutant LALAPGTA_DNA

<400> SEQUENCE: 149

```
gaggtgcagc tgttggagtc tgggggaggc ttggtacagc ctggggggtc cctgagactc        60
tcctgtgcag cctctggatt cacctttagc agttatgata tgagctgggt ccgccaggct       120
ccagggaagg ggctggagtg ggtctcagcg atctcttatg ataatggtaa tacatattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctcagc ctccaccaag       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaagccg cggggggacc gtcagtcttc       720
ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cgcctaccgt       900
gtggtcagcg tcctcaccgt cctgcaccag gactggctga atggcaagga gtacaagtgc       960
aaggtctcca acaaagccct cggcgccccc atcgagaaaa ccatctccaa agccaaaggg      1020
```

```
cagcccccgag aaccacaggt gtatacccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

<210> SEQ ID NO 150
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG4 wild type_amino acid

<400> SEQUENCE: 150

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285
```

-continued

```
Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
        435                 440
```

```
<210> SEQ ID NO 151
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG4 wild type_DNA

<400> SEQUENCE: 151
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg aacagcggc     480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctacatacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
```

-continued

```
ctgacatgtc tggtgaaggg cttctatccc tccgacatcg ccgtggagtg ggagtctaat      1140
ggccagcctg agaacaatta caagaccaca ccccctgtgc tggactctga tggcagcttc      1200
tttctgtatt ccaggctgac cgtggataag tctcggtggc aggagggcaa cgtgttcagc      1260
tgctctgtga tgcacgaagc cctgcataat cactatactc agaaaagtct gtcactgtca      1320
ctgggaaag                                                               1329
```

<210> SEQ ID NO 152
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain_IgG4 mutant TA_amino acid

<400> SEQUENCE: 152

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Ala Tyr Arg Val Val Ser Val Leu Thr Val
    290                 295                 300
```

```
Leu His Gln Asp Trp Leu Asn Gly Lys Glu Tyr Lys Cys Lys Val Ser
305             310             315             320

Asn Lys Gly Leu Pro Ser Ser Ile Glu Lys Thr Ile Ser Lys Ala Lys
            325             330             335

Gly Gln Pro Arg Glu Pro Gln Val Tyr Thr Leu Pro Pro Ser Gln Glu
            340             345             350

Glu Met Thr Lys Asn Gln Val Ser Leu Thr Cys Leu Val Lys Gly Phe
            355             360             365

Tyr Pro Ser Asp Ile Ala Val Glu Trp Glu Ser Asn Gly Gln Pro Glu
            370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
            405             410             415

Asn Val Phe Ser Cys Ser Val Met His Glu Ala Leu His Asn His Tyr
            420             425             430

Thr Gln Lys Ser Leu Ser Leu Ser Leu Gly Lys
            435             440
```

```
<210> SEQ ID NO 153
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain_IgG4 mutant TA_DNA

<400> SEQUENCE: 153
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc cagcaccaag     360
ggcccttccg tgtttcccct ggccccttgc tccggtccaa catctgagag caccgccgcc     420
ctgggctgtc tggtgaagga ctacttccca gagcccgtga ccgtgagctg aacagcggc     480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctgcctacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
```

-continued

```
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                            1329
```

<210> SEQ ID NO 154
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG1 mutant TA_amino acid

<400> SEQUENCE: 154

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
```

-continued

```
305            310            315            320

Lys Val Ser Asn Lys Ala Leu Pro Ala Pro Ile Glu Lys Thr Ile Ser
                325                330                335

Lys Ala Lys Gly Gln Pro Arg Glu Pro Gln Val Tyr Thr Leu Pro Pro
                340                345                350

Ser Arg Asp Glu Leu Thr Lys Asn Gln Val Ser Leu Thr Cys Leu Val
                355                360                365

Lys Gly Phe Tyr Pro Ser Asp Ile Ala Val Glu Trp Glu Ser Asn Gly
        370                375                380

Gln Pro Glu Asn Asn Tyr Lys Thr Thr Pro Pro Val Leu Asp Ser Asp
385                390                395                400

Gly Ser Phe Phe Leu Tyr Ser Lys Leu Thr Val Asp Lys Ser Arg Trp
                405                410                415

Gln Gln Gly Asn Val Phe Ser Cys Ser Val Met His Glu Ala Leu His
                420                425                430

Asn His Tyr Thr Gln Lys Ser Leu Ser Leu Ser Pro Gly Lys
                435                440                445
```

<210> SEQ ID NO 155
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG1 mutant TA_DNA

<400> SEQUENCE: 155

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
```

-continued

```
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

```
<210> SEQ ID NO 156
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG1 mutant LALA_amino acid

<400> SEQUENCE: 156

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320
```

-continued

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

```
<210> SEQ ID NO 157
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG1 mutant LALA_DNA

<400> SEQUENCE: 157
gaggtgcagc tgttggagtc tggggaggc ttggtacagc ctggggggtc cctgagactc      60
tcctgtgcag cctctggatt caccttttagc agttatgata tgagctgggt ccgccaggct    120
ccagggaagg ggctggagtg ggtctcagtg atctcttctg atggtggtaa tacatattac    180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagccg ccgggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtaccctg cccccatccc gggatgagct gaccaagaac    1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
```

-continued

```
gtcttctcat gctccgtgat gcatgaggct ctgcacaacc actacacgca gaagagcctc      1320
tccctgtccc cgggtaaa                                                    1338
```

<210> SEQ ID NO 158
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG1 mutant LALATA_amino acid

<400> SEQUENCE: 158

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335
```

-continued

```
Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
            370             375             380

Gln Pro Glu Asn Asn Tyr Lys Thr Thr Pro Pro Val Leu Asp Ser Asp
        385             390             395             400

Gly Ser Phe Phe Leu Tyr Ser Lys Leu Thr Val Asp Lys Ser Arg Trp
                405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

```
<210> SEQ ID NO 159
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG1 mutant LALATA_DNA

<400> SEQUENCE: 159
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggaccccctga ggtcacatgc     780 gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
```

-continued

```
tccctgtccc cgggtaaa                                                    1338
```

<210> SEQ ID NO 160
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG1 mutant LALAPG_amino acid

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Val Ile Ser Ser Asp Gly Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
```

-continued

```
                340              345              350
Ser Arg Asp Glu Leu Thr Lys Asn Gln Val Ser Leu Thr Cys Leu Val
         355              360              365
Lys Gly Phe Tyr Pro Ser Asp Ile Ala Val Glu Trp Glu Ser Asn Gly
     370              375              380
Gln Pro Glu Asn Asn Tyr Lys Thr Thr Pro Pro Val Leu Asp Ser Asp
385              390              395              400
Gly Ser Phe Phe Leu Tyr Ser Lys Leu Thr Val Asp Lys Ser Arg Trp
             405              410              415
Gln Gln Gly Asn Val Phe Ser Cys Ser Val Met His Glu Ala Leu His
             420              425              430
Asn His Tyr Thr Gln Lys Ser Leu Ser Leu Ser Pro Gly Lys
         435              440              445
```

```
<210> SEQ ID NO 161
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG1 mutant LALAPG_DNA

<400> SEQUENCE: 161
gaggtgcagc tgttggagtc tggggggaggc ttggtacagc ctggggggtc cctgagactc      60
tcctgtgcag cctctggatt caccttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttcccect ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720 ctcttcccec caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

-continued

<210> SEQ ID NO 162
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG1 mutant LALAPGTA_amino
      acid

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Val Ile Ser Ser Asp Gly Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

-continued

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 163
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG1 mutant LALAPGTA_DNA

<400> SEQUENCE: 163

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttcCccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020
cagccccgag aaccacaggt gtatACCctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

<210> SEQ ID NO 164
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG4 wild type_amino acid

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe

```
              355               360               365
Tyr Pro Ser Asp Ile Ala Val Glu Trp Glu Ser Asn Gly Gln Pro Glu
        370               375               380
Asn Asn Tyr Lys Thr Thr Pro Pro Val Leu Asp Ser Asp Gly Ser Phe
385               390               395               400
Phe Leu Tyr Ser Arg Leu Thr Val Asp Lys Ser Arg Trp Gln Glu Gly
                405               410               415
Asn Val Phe Ser Cys Ser Val Met His Glu Ala Leu His Asn His Tyr
            420               425               430
Thr Gln Lys Ser Leu Ser Leu Ser Leu Gly Lys
        435               440
```

```
<210> SEQ ID NO 165
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG4 wild type_DNA

<400> SEQUENCE: 165
gaggtgcagc tgttggagtc tggggaggc ttggtacagc ctggggggtc cctgagactc      60
tcctgtgcag cctctggatt caccttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc cagcaccaag     360
ggcccttccg tgtttcccct ggccccttgc tcccggtcca catctgagag caccgccgcc     420
ctgggctgtc tggtgaagga ctacttccca gagcccgtga ccgtgagctg aacagcggc     480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg ataagcgggt ggagtctaa gtacggccct     660 ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctacatacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca cccctgtgc tggactctga tggcagcttc     1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                            1329
```

```
<210> SEQ ID NO 166
<211> LENGTH: 443
```

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 1_IgG4 mutant TA_amino acid

<400> SEQUENCE: 166

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Val Ile Ser Ser Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Ala Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365
```

-continued

```
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
            435                 440
```

```
<210> SEQ ID NO 167
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 1_IgG4 mutant TA_DNA

<400> SEQUENCE: 167
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagtg atctcttctg atggtggtaa tacatattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc cagcaccaag     360
ggcccttccg tgtttccccct ggccccttgc tcccggtcca catctgagag caccgccgcc     420
ctgggctgtc tggtgaagga ctacttccca gagcccgtga ccgtgagctg aacagcggc      480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctgcctacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacacccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                           1329
```

```
<210> SEQ ID NO 168
<211> LENGTH: 446
<212> TYPE: PRT
<213> ORGANISM: Artificial Sequence
```

-continued

<220> FEATURE:
<223> OTHER INFORMATION: Description of Artificial Sequence: Synthetic
      polypeptide
<220> FEATURE:
<223> OTHER INFORMATION: IgG heavy chain 2_IgG1 mutant TA_amino acid

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

```
<210> SEQ ID NO 169
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG1 mutant TA_DNA

<400> SEQUENCE: 169
gaggtgcagc tgttggagtc tggggggggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc      420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338

<210> SEQ ID NO 170
<211> LENGTH: 446
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<223> OTHER INFORMATION: IgG heavy chain 2_IgG1 mutant LALA_amino acid

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
```

-continued

```
       385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

```
<210> SEQ ID NO 171
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG1 mutant LALA_DNA

<400> SEQUENCE: 171
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720 ctcttcccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                 1338
```

```
<210> SEQ ID NO 172
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: IgG heavy chain 2_IgG1 mutant LALATA_amino acid

<400> SEQUENCE: 172

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Gln Met Gly Arg Val Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

```
<210> SEQ ID NO 173
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG1 mutant LALATA_DNA

<400> SEQUENCE: 173
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca gcccagcaa caccaaggtg gacaagaaag ttgagcccaa atcttgtgac     660
aaaactcaca catgcccacc gtgcccagca cctgaagccg ccggggggacc gtcagtcttc     720 ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtatacccctg ccccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                 1338
```

```
<210> SEQ ID NO 174
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 2_IgG1 mutant LALAPG_amino acid
```

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

-continued

```
Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 175
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG1 mutant LALAPG_DNA

<400> SEQUENCE: 175
gaggtgcagc tgttggagtc tggggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338

<210> SEQ ID NO 176
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 2_IgG1 mutant LALAPGTA_amino
      acid

<400> SEQUENCE: 176
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415
```

-continued

```
Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
        435                 440                 445

<210> SEQ ID NO 177
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG1 mutant LALAPGTA_DNA

<400> SEQUENCE: 177
gaggtgcagc tgttggagtc tggggggaggc ttggtacagc ctgggggtc cctgagactc      60 tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccccct ggcaccctcc tccaagagca cctctgggggg cacagcggcc     420 ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttcccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cggcgcccccc atcgagaaaa ccatctccaa agccaaaggg    1020
cagccccgag aaccacaggt gtaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctccccgtgct ggactccgac    1200 ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                1338

<210> SEQ ID NO 178
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 2_IgG4 wild type_amino acid

<400> SEQUENCE: 178

Glu Val Gln Leu Leu Glu Ser Gly Gly Gly Leu Val Gln Pro Gly Gly
```

```
1                5                   10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Gly Leu Glu Trp Val
             35                  40                  45

Ser Ala Ile Ser Pro Gln Met Gly Arg Val Tyr Tyr Ala Asp Ser Val
             50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Met Ala Leu Asp Phe Asp Tyr Trp Gly Gln Gly Thr Leu Val
             100                 105                 110

Thr Val Ser Ser Ala Ser Thr Lys Gly Pro Ser Val Phe Pro Leu Ala
             115                 120                 125

Pro Cys Ser Arg Ser Thr Ser Glu Ser Thr Ala Ala Leu Gly Cys Leu
         130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Lys Thr Tyr Thr Cys Asn Val Asp His Lys Pro Ser Asn Thr
             195                 200                 205

Lys Val Asp Lys Arg Val Glu Ser Lys Tyr Gly Pro Pro Cys Pro Ser
         210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                 245                 250                 255

Cys Val Val Val Asp Val Ser Gln Glu Asp Pro Glu Val Gln Phe Asn
             260                 265                 270

Trp Tyr Val Asp Gly Val Glu Val His Asn Ala Lys Thr Lys Pro Arg
             275                 280                 285

Glu Glu Gln Phe Asn Ser Thr Tyr Arg Val Val Ser Val Leu Thr Val
         290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                 325                 330                 335

Gly Gln Pro Arg Glu Pro Gln Val Tyr Thr Leu Pro Pro Ser Gln Glu
             340                 345                 350

Glu Met Thr Lys Asn Gln Val Ser Leu Thr Cys Leu Val Lys Gly Phe
             355                 360                 365

Tyr Pro Ser Asp Ile Ala Val Glu Trp Glu Ser Asn Gly Gln Pro Glu
         370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                 405                 410                 415

Asn Val Phe Ser Cys Ser Val Met His Glu Ala Leu His Asn His Tyr
             420                 425                 430
```

Thr Gln Lys Ser Leu Ser Leu Ser Leu Gly Lys
        435                 440

<210> SEQ ID NO 179
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG4 wild type_DNA

<400> SEQUENCE: 179
gaggtgcagc tgttggagtc tggggggaggc ttggtacagc ctggggggtc cctgagactc       60
tcctgtgcag cctctggatt caccttagc agttatgata tgagctgggt ccgccaggct      120
ccagggaagg ggctggagtg ggtctcagcg atctcgccgc agatgggtcg ggtgtattac      180
gctgattctg taaaaggtcg gttcaccatc tccagagaca attccaagaa cacgctgtat      240
ctgcaaatga acagcctgag agccgaggac acggccgtgt attactgtgc gagaatggcg      300
cttgatttcg actactgggg ccagggtaca ctggtcaccg tgagctcagc cagcaccaag      360
ggcccttccg tgtttcccct ggcccccttgc tcccggtcca catctgagag caccgccgcc      420
ctgggctgtc tggtgaagga ctacttccca gagcccgtga ccgtgagctg gaacagcggc      480
gccctgacaa gcggcgtgca cacatttccc gccgtgctgc agagctccgg cctgtactcc      540
ctgtctagcg tggtgacagt gccttcctct agcctgggca ccaagacata tacctgtaac      600
gtggaccaca gccaagcaa taccaaggtg gataagcggg tggagtctaa gtacggccct      660
ccttgcccta gctgtcctgc tccagagttt ctgggcggcc cttccgtgtt cctgtttcca      720
cccaaaccaa aggacacact gatgatctct agaacaccag aggtgacctg cgtggtggtg      780
gacgtgagcc aggaggatcc cgaggtgcag ttcaactggt acgtggatgg cgtggaggtg      840
cacaatgcca gaccaagcc aagagaggag cagtttaact ctacatacag ggtggtgagc      900
gtgctgaccg tgctgcacca ggattggctc aacggcaagg agtataagtg caaggtgtcc      960
aataagggcc tgccctcctc tatcgagaag acaatctcta aggctaaggg ccagccaaga     1020
gagcctcagg tgtacaccct gcctccaagc caggaggaga tgacaaagaa ccaggtgtcc     1080
ctgacatgtc tggtgaaggg cttctatccc tccgacatcg ccgtggagtg ggagtctaat     1140
ggccagcctg agaacaatta caagaccaca cccctgtgc tggactctga tggcagcttc     1200
tttctgtatt ccaggctgac cgtggataag tctcggtggc aggagggcaa cgtgttcagc     1260
tgctctgtga tgcacgaagc cctgcataat cactatactc agaaaagtct gtcactgtca     1320
ctgggaaag                                                             1329

<210> SEQ ID NO 180
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 2_IgG4 mutant TA_amino acid

<400> SEQUENCE: 180

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
        20                  25                  30

Asp Met Ser Trp Val Arg Gln Ala Pro Gly Lys Gly Leu Glu Trp Val
        35                  40                  45

Ser Ala Ile Ser Pro Gln Met Gly Arg Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
        100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Ala Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
```

-continued

<210> SEQ ID NO 181
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 2_IgG4 mutant TA_DNA

<400> SEQUENCE: 181
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctcgccgc agatgggtcg ggtgtattac     180
gctgattctg taaaaggtcg gttcaccatc tccagagaca attccaagaa cacgctgtat     240
ctgcaaatga cagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg aacagcggc     480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca gaccaagcc aagagaggag cagtttaact ctgcctacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca cccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                           1329

<210> SEQ ID NO 182
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG1 mutant TA_amino acid

<400> SEQUENCE: 182

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

-continued

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 183
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 3_IgG1 mutant TA_DNA

<400> SEQUENCE: 183
gaggtgcagc tgttggagtc tggggggaggc ttggtacagc ctggggggtc cctgagactc        60
tcctgtgcag cctctggatt caccttagc agttatgata tgagctgggt ccgccaggct       120
ccagggaagg ggctggagtg ggtctcagcg atcgatccgt gggggggtaa tatttattac       180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctcagc ctccaccaag       360
ggcccatcgg tcttcccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaactcc tggggggacc gtcagtcttc       720 ctcttcccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cgcctaccgt       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtataccctg cccccatccc gggatgagct gaccaagaac      1080
caggtcagcc tgacctgcct ggtcaaaggc ttctatccca gcgacatcgc cgtggagtgg      1140
gagagcaatg gcagccggga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338

<210> SEQ ID NO 184
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG1 mutant LALA_amino acid

<400> SEQUENCE: 184

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val

```
            35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 185
```

<211> LENGTH: 1338
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<223> OTHER INFORMATION: IgG heavy chain 3_IgG1 mutant LALA_DNA

<400> SEQUENCE: 185

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcgatccgt ggggggtaa tatttattac     180 gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg cggggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

<210> SEQ ID NO 186
<211> LENGTH: 446
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: IgG heavy chain 3_IgG1 mutant LALALATA_amino acid

<400> SEQUENCE: 186

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45
```

```
Ser Ala Ile Asp Pro Leu Gly Gly Asn Ile Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Met Ala Leu Asp Phe Asp Tyr Trp Gly Gln Gly Thr Leu Val
            100             105             110

Thr Val Ser Ser Ala Ser Thr Lys Gly Pro Ser Val Phe Pro Leu Ala
            115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Lys Val Glu Pro Lys Ser Cys Asp Lys Thr His Thr
    210             215             220

Cys Pro Pro Cys Pro Ala Pro Glu Ala Ala Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Ala Lys Thr
            275             280             285

Lys Pro Arg Glu Glu Gln Tyr Asn Ser Ala Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335

Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
    370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

<210> SEQ ID NO 187
<211> LENGTH: 1338
<212> TYPE: DNA

-continued

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 3_IgG1 mutant LALATA_DNA

<400> SEQUENCE: 187

```
gaggtgcagc tgttggagtc tggggggaggc ttggtacagc ctggggggtc cctgagactc      60
tcctgtgcag cctctggatt caccctttagc agttatgata tgagctgggt ccgccaggct     120
ccagggaagg ggctggagtg ggtctcagcg atcgatccgt tgggggggtaa tatttattac     180 gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

<210> SEQ ID NO 188
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG1 mutant LALAPG_amino acid

<400> SEQUENCE: 188

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 189
<211> LENGTH: 1338
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: IgG heavy chain 3_IgG1 mutant LALAPG_DNA

<400> SEQUENCE: 189

```
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atcgatccgt ggggggggtaa tatttattac     180 gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttcccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cggcgcccccc atcgagaaaa ccatctccaa agccaaaggg    1020
cagccccgag aaccacaggt gtatacccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

<210> SEQ ID NO 190
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG1 mutant LALAPGTA_amino
      acid

<400> SEQUENCE: 190

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 191
<211> LENGTH: 1338
<212> TYPE: DNA
<213> ORGANISM: Artificial Sequence
<220> FEATURE:
<223> OTHER INFORMATION: Description of Artificial Sequence: Synthetic

```
        polynucleotide
<220> FEATURE:
<223> OTHER INFORMATION: IgG heavy chain 3_IgG1 mutant LALAPGTA_DNA

<400> SEQUENCE: 191
gaggtgcagc tgttggagtc tgggggaggc ttggtacagc ctgggggggtc cctgagactc      60 tcctgtgcag cctctggatt caccttagc agttatgata tgagctgggt ccgccaggct     120
ccagggaagg ggctggagtg ggtctcagcg atcgatccgt tggggggtaa tatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca gcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338

<210> SEQ ID NO 192
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG4 wild type_amino acid

<400> SEQUENCE: 192

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
            85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
            435                 440
```

<210> SEQ ID NO 193
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: IgG heavy chain 3_IgG4 wild type_DNA

<400> SEQUENCE: 193

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcgatccgt tggggggtaa tatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggccccttgc tccggtcca catctgagag caccgccgcc     420
ctgggctgtc tggtgaagga ctacttccca gagcccgtga ccgtgagctg aacagcggc     480 gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg ataagcgggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctacatacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                           1329
```

<210> SEQ ID NO 194
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 3_IgG4 mutant TA_amino acid

<400> SEQUENCE: 194

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Asp Pro Leu Gly Gly Asn Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                    85                90                95

Ala Arg Met Ala Leu Asp Phe Asp Tyr Trp Gly Gln Gly Thr Leu Val
            100               105               110

Thr Val Ser Ser Ala Ser Thr Lys Gly Pro Ser Val Phe Pro Leu Ala
            115               120               125

Pro Cys Ser Arg Ser Thr Ser Glu Ser Thr Ala Ala Leu Gly Cys Leu
            130               135               140

Val Lys Asp Tyr Phe Pro Glu Pro Val Thr Val Ser Trp Asn Ser Gly
145               150               155               160

Ala Leu Thr Ser Gly Val His Thr Phe Pro Ala Val Leu Gln Ser Ser
                165               170               175

Gly Leu Tyr Ser Leu Ser Ser Val Val Thr Val Pro Ser Ser Ser Leu
                180               185               190

Gly Thr Lys Thr Tyr Thr Cys Asn Val Asp His Lys Pro Ser Asn Thr
                195               200               205

Lys Val Asp Lys Arg Val Glu Ser Lys Tyr Gly Pro Pro Cys Pro Ser
            210               215               220

Cys Pro Ala Pro Glu Phe Leu Gly Gly Pro Ser Val Phe Leu Phe Pro
225               230               235               240

Pro Lys Pro Lys Asp Thr Leu Met Ile Ser Arg Thr Pro Glu Val Thr
                245               250               255

Cys Val Val Val Asp Val Ser Gln Glu Asp Pro Glu Val Gln Phe Asn
                260               265               270

Trp Tyr Val Asp Gly Val Glu Val His Asn Ala Lys Thr Lys Pro Arg
                275               280               285

Glu Glu Gln Phe Asn Ser Ala Tyr Arg Val Val Ser Val Leu Thr Val
            290               295               300

Leu His Gln Asp Trp Leu Asn Gly Lys Glu Tyr Lys Cys Lys Val Ser
305               310               315               320

Asn Lys Gly Leu Pro Ser Ser Ile Glu Lys Thr Ile Ser Lys Ala Lys
                325               330               335

Gly Gln Pro Arg Glu Pro Gln Val Tyr Thr Leu Pro Pro Ser Gln Glu
                340               345               350

Glu Met Thr Lys Asn Gln Val Ser Leu Thr Cys Leu Val Lys Gly Phe
                355               360               365

Tyr Pro Ser Asp Ile Ala Val Glu Trp Glu Ser Asn Gly Gln Pro Glu
            370               375               380

Asn Asn Tyr Lys Thr Thr Pro Pro Val Leu Asp Ser Asp Gly Ser Phe
385               390               395               400

Phe Leu Tyr Ser Arg Leu Thr Val Asp Lys Ser Arg Trp Gln Glu Gly
                405               410               415

Asn Val Phe Ser Cys Ser Val Met His Glu Ala Leu His Asn His Tyr
                420               425               430

Thr Gln Lys Ser Leu Ser Leu Ser Leu Gly Lys
            435               440
```

<210> SEQ ID NO 195
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 3_IgG4 mutant TA_DNA

```
<400> SEQUENCE: 195
gaggtgcagc tgttggagtc tggggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atcgatccgt tggggggtaa tatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tccgggtcca catctgagag caccgccgcc     420
ctgggctgtc tggtgaagga ctacttccca gagcccgtga ccgtgagctg gaacagcggc     480
gccctgacaa cggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca gaccaagcc aagagaggag cagtttaact ctgcctacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                            1329

<210> SEQ ID NO 196
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG1 mutant TA_amino acid

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95
```

```
Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 197
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG1 mutant TA_DNA

<400> SEQUENCE: 197

-continued

```
gaggtgcagc tgttggagtc tggggggaggc ttggtacagc ctgggggggtc cctgagactc          60 tcctgtgcag cctctggatt cacctttagc agttatgata tgagctgggt ccgccaggct         120
ccagggaagg ggctggagtg ggtctcagcg atctctccgt attcgggtag gatttattac         180
gctgattctg taaaaggtcg gttcaccatc tccagagaca attccaagaa cacgctgtat         240
ctgcaaatga acagcctgag agccgaggac acggccgtgt attactctgc gagaatggcg         300
cttgatttcg actactgggg ccagggtaca ctggtcaccg tgagctcagc ctccaccaag         360
ggcccatcgg tcttccccct ggcaccctcc tccaagagca cctctggggg cacagcggcc         420
ctgggctgcc tggtcaagga ctacttcccc gaaccggtga cggtgtcgtg gaactcaggc         480
gccctgacca gcggcgtgca caccttcccg gctgtcctac agtcctcagg actctactcc         540
ctcagcagcg tggtgaccgt gccctccagc agcttgggca cccagaccta catctgcaac         600
gtgaatcaca agcccagcaa caccaaggtg gacaagaaag ttgagcccaa atcttgtgac         660
aaaactcaca catgcccacc gtgcccagca cctgaactcc tggggggacc gtcagtcttc         720
ctcttccccc caaaacccaa ggacaccctc atgatctccc ggacccctga ggtcacatgc         780
gtggtggtgg acgtgagcca cgaagaccct gaggtcaagt tcaactggta cgtggacggc         840
gtggaggtgc ataatgccaa gacaaagccg cgggaggagc agtacaacag cgcctaccgt         900
gtggtcagcg tcctcaccgt cctgcaccag gactggctga atggcaagga gtacaagtgc         960
aaggtctcca acaaagccct cccagccccc atcgagaaa ccatctccaa agccaaaggg        1020
cagccccgag aaccacaggt gtataccctg cccccatccc gggatgagct gaccaagaac        1080
caggtcagcc tgacctgcct ggtcaaaggc ttctatccca gcgacatcgc cgtggagtgg        1140
gagagcaatg ggcagccgga gaacaactac aagaccacgc ctcccgtgct ggactccgac        1200
ggctccttct tcctctacag caagctcacc gtggacaaga gcaggtggca gcaggggaac        1260
gtcttctcat gctccgtgat gcatgaggct ctgcacaacc actacacgca gaagagcctc        1320
tccctgtccc cgggtaaa                                                      1338
```

```
<210> SEQ ID NO 198
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG1 mutant LALA_amino acid

<400> SEQUENCE: 198

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110
```

```
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 199
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG1 mutant LALA_DNA

<400> SEQUENCE: 199
gaggtgcagc tgttggagtc tggggggaggc ttggtacagc ctggggggtc cctgagactc      60
```

```
tcctgtgcag cctctggatt cacctttagc agttatgata tgagctgggt ccgccaggct    120
ccagggaagg ggctggagtg ggtctcagcg atctctccgt attcgggtag gatttattac    180
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagccg ccggggggacc gtcagtcttc    720 ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338
```

```
<210> SEQ ID NO 200
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG1 mutant LALATA_amino acid

<400> SEQUENCE: 200

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
```

-continued

```
            115                 120                 125
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
                195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Ala Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 201
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG1 mutant LALATA_DNA

<400> SEQUENCE: 201

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
```

-continued

```
ccagggaagg ggctggagtg ggtctcagcg atctctccgt attcgggtag gatttattac       180
gctgattctg taaaaggtcg gttcaccatc tccagagaca attccaagaa cacgctgtat       240
ctgcaaatga acagcctgag agccgaggac acggccgtgt attactctgc gagaatggcg       300
cttgatttcg actactgggg ccagggtaca ctggtcaccg tgagctcagc ctccaccaag       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaagccg ccggggggacc gtcagtcttc       720 ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cgcctaccgt       900
gtggtcagcg tcctcaccgt cctgcaccag gactggctga atggcaagga gtacaagtgc       960
aaggtctcca acaaagccct cccagccccc atcgagaaaa ccatctccaa agccaaaggg      1020
cagccccgag aaccacaggt gtataccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338
```

```
<210> SEQ ID NO 202
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG1 mutant LALAPG_amino acid

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130              135              140

Val Lys Asp Tyr Phe Pro Glu Pro Val Thr Val Ser Trp Asn Ser Gly
145              150              155              160

Ala Leu Thr Ser Gly Val His Thr Phe Pro Ala Val Leu Gln Ser Ser
            165              170              175

Gly Leu Tyr Ser Leu Ser Ser Val Val Thr Val Pro Ser Ser Ser Leu
            180              185              190

Gly Thr Gln Thr Tyr Ile Cys Asn Val Asn His Lys Pro Ser Asn Thr
            195              200              205

Lys Val Asp Lys Lys Val Glu Pro Lys Ser Cys Asp Lys Thr His Thr
    210              215              220

Cys Pro Pro Cys Pro Ala Pro Glu Ala Ala Gly Gly Pro Ser Val Phe
225              230              235              240

Leu Phe Pro Pro Lys Pro Lys Asp Thr Leu Met Ile Ser Arg Thr Pro
            245              250              255

Glu Val Thr Cys Val Val Val Asp Val Ser His Glu Asp Pro Glu Val
            260              265              270

Lys Phe Asn Trp Tyr Val Asp Gly Val Glu Val His Asn Ala Lys Thr
    275              280              285

Lys Pro Arg Glu Glu Gln Tyr Asn Ser Thr Tyr Arg Val Val Ser Val
    290              295              300

Leu Thr Val Leu His Gln Asp Trp Leu Asn Gly Lys Glu Tyr Lys Cys
305              310              315              320

Lys Val Ser Asn Lys Ala Leu Gly Ala Pro Ile Glu Lys Thr Ile Ser
            325              330              335

Lys Ala Lys Gly Gln Pro Arg Glu Pro Gln Val Tyr Thr Leu Pro Pro
            340              345              350

Ser Arg Asp Glu Leu Thr Lys Asn Gln Val Ser Leu Thr Cys Leu Val
            355              360              365

Lys Gly Phe Tyr Pro Ser Asp Ile Ala Val Glu Trp Glu Ser Asn Gly
    370              375              380

Gln Pro Glu Asn Asn Tyr Lys Thr Thr Pro Pro Val Leu Asp Ser Asp
385              390              395              400

Gly Ser Phe Phe Leu Tyr Ser Lys Leu Thr Val Asp Lys Ser Arg Trp
            405              410              415

Gln Gln Gly Asn Val Phe Ser Cys Ser Val Met His Glu Ala Leu His
            420              425              430

Asn His Tyr Thr Gln Lys Ser Leu Ser Leu Ser Pro Gly Lys
            435              440              445
```

<210> SEQ ID NO 203
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG1 mutant LALAPG_DNA

<400> SEQUENCE: 203
gaggtgcagc tgttggagtc tggggggaggc ttggtacagc ctggggggtc cctgagactc        60
tcctgtgcag cctctggatt caccttttagc agttatgata tgagctgggt ccgccaggct       120
ccagggaagg ggctggagtg ggtctcagcg atctctccgt attcgggtag gatttattac       180

-continued

```
gctgattctg taaaaggtcg gttcaccatc tccagagaca attccaagaa cacgctgtat    240
ctgcaaatga acagcctgag agccgaggac acggccgtgt attactctgc gagaatggcg    300
cttgatttcg actactgggg ccagggtaca ctggtcaccg tgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagccg ccggggggacc gtcagtcttc    720 ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                  1338
```

<210> SEQ ID NO 204
<211> LENGTH: 446
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<223> OTHER INFORMATION: IgG heavy chain 4_IgG1 mutant LALAPGTA_amino
     acid

<400> SEQUENCE: 204

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
              130                  135                  140
Val Lys Asp Tyr Phe Pro Glu Pro Val Thr Val Ser Trp Asn Ser Gly
145                  150                  155                  160

Ala Leu Thr Ser Gly Val His Thr Phe Pro Ala Val Leu Gln Ser Ser
                165                  170                  175

Gly Leu Tyr Ser Leu Ser Ser Val Val Thr Val Pro Ser Ser Ser Leu
                180                  185                  190

Gly Thr Gln Thr Tyr Ile Cys Asn Val Asn His Lys Pro Ser Asn Thr
                195                  200                  205

Lys Val Asp Lys Lys Val Glu Pro Lys Ser Cys Asp Lys Thr His Thr
            210                  215                  220

Cys Pro Pro Cys Pro Ala Pro Glu Ala Ala Gly Gly Pro Ser Val Phe
225                  230                  235                  240

Leu Phe Pro Pro Lys Pro Lys Asp Thr Leu Met Ile Ser Arg Thr Pro
                245                  250                  255

Glu Val Thr Cys Val Val Val Asp Val Ser His Glu Asp Pro Glu Val
                260                  265                  270

Lys Phe Asn Trp Tyr Val Asp Gly Val Glu Val His Asn Ala Lys Thr
            275                  280                  285

Lys Pro Arg Glu Glu Gln Tyr Asn Ser Ala Tyr Arg Val Val Ser Val
            290                  295                  300

Leu Thr Val Leu His Gln Asp Trp Leu Asn Gly Lys Glu Tyr Lys Cys
305                  310                  315                  320

Lys Val Ser Asn Lys Ala Leu Gly Ala Pro Ile Glu Lys Thr Ile Ser
                325                  330                  335

Lys Ala Lys Gly Gln Pro Arg Glu Pro Gln Val Tyr Thr Leu Pro Pro
                340                  345                  350

Ser Arg Asp Glu Leu Thr Lys Asn Gln Val Ser Leu Thr Cys Leu Val
                355                  360                  365

Lys Gly Phe Tyr Pro Ser Asp Ile Ala Val Glu Trp Glu Ser Asn Gly
            370                  375                  380

Gln Pro Glu Asn Asn Tyr Lys Thr Thr Pro Pro Val Leu Asp Ser Asp
385                  390                  395                  400

Gly Ser Phe Phe Leu Tyr Ser Lys Leu Thr Val Asp Lys Ser Arg Trp
                405                  410                  415

Gln Gln Gly Asn Val Phe Ser Cys Ser Val Met His Glu Ala Leu His
            420                  425                  430

Asn His Tyr Thr Gln Lys Ser Leu Ser Leu Ser Pro Gly Lys
            435                  440                  445
```

<210> SEQ ID NO 205
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG1 mutant LALAPGTA_DNA

<400> SEQUENCE: 205

```
gaggtgcagc tgttggagtc tgggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
```

```
ctgcaaatga acagcctgag agccgaggac acggccgtgt attactctgc gagaatggcg      300
cttgatttcg actactgggg ccagggtaca ctggtcaccg tgagctcagc ctccaccaag      360
ggcccatcgg tcttccccct ggcaccctcc tccaagagca cctctggggg cacagcggcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca gcccagcaac caccaaggtg gacaagaaag ttgagcccaa atcttgtgac      660
aaaactcaca catgcccacc gtgcccagca cctgaagccg ccgggggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cgcctaccgt      900
gtggtcagcg tcctcaccgt cctgcaccag gactggctga atggcaagga gtacaagtgc      960
aaggtctcca acaaagccct cggcgccccc atcgagaaaa ccatctccaa agccaaaggg     1020
cagccccgag aaccacaggt gtataccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338
```

```
<210> SEQ ID NO 206
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG4 wild type_amino acid

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140
```

-continued

```
Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
                165             170             175

Gly Leu Tyr Ser Leu Ser Ser Val Val Thr Val Pro Ser Ser Ser Leu
            180             185             190

Gly Thr Lys Thr Tyr Thr Cys Asn Val Asp His Lys Pro Ser Asn Thr
        195             200             205

Lys Val Asp Lys Arg Val Glu Ser Lys Tyr Gly Pro Pro Cys Pro Ser
    210             215             220

Cys Pro Ala Pro Glu Phe Leu Gly Gly Pro Ser Val Phe Leu Phe Pro
225             230             235             240

Pro Lys Pro Lys Asp Thr Leu Met Ile Ser Arg Thr Pro Glu Val Thr
            245             250             255

Cys Val Val Val Asp Val Ser Gln Glu Asp Pro Glu Val Gln Phe Asn
            260             265             270

Trp Tyr Val Asp Gly Val Glu Val His Asn Ala Lys Thr Lys Pro Arg
        275             280             285

Glu Glu Gln Phe Asn Ser Thr Tyr Arg Val Val Ser Val Leu Thr Val
    290             295             300

Leu His Gln Asp Trp Leu Asn Gly Lys Glu Tyr Lys Cys Lys Val Ser
305             310             315             320

Asn Lys Gly Leu Pro Ser Ser Ile Glu Lys Thr Ile Ser Lys Ala Lys
            325             330             335

Gly Gln Pro Arg Glu Pro Gln Val Tyr Thr Leu Pro Pro Ser Gln Glu
            340             345             350

Glu Met Thr Lys Asn Gln Val Ser Leu Thr Cys Leu Val Lys Gly Phe
        355             360             365

Tyr Pro Ser Asp Ile Ala Val Glu Trp Glu Ser Asn Gly Gln Pro Glu
    370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
            405             410             415

Asn Val Phe Ser Cys Ser Val Met His Glu Ala Leu His Asn His Tyr
            420             425             430

Thr Gln Lys Ser Leu Ser Leu Ser Leu Gly Lys
        435             440
```

```
<210> SEQ ID NO 207
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG4 wild type_DNA

<400> SEQUENCE: 207
gaggtgcagc tgttggagtc tgggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
```

-continued

```
cttgatttcg actactgggg ccagggtaca ctggtcaccg tgagctcagc cagcaccaag      360
ggcccttccg tgtttcccct ggccccttgc tcccggtcca catctgagag caccgccgcc      420
ctgggctgtc tggtgaagga ctacttccca gagcccgtga ccgtgagctg gaacagcggc      480
gccctgacaa gcggcgtgca cacatttccc gccgtgctgc agagctccgg cctgtactcc      540
ctgtctagcg tggtgacagt gccttcctct agcctgggca ccaagacata tacctgtaac      600
gtggaccaca agcccaagcaa taccaaggtg gataagcggg tggagtctaa gtacggccct      660
ccttgcccta gctgtcctgc tccagagttt ctgggcggcc cttccgtgtt cctgtttcca      720
cccaaaccaa aggacacact gatgatctct agaacaccag aggtgacctg cgtggtggtg      780
gacgtgagcc aggaggatcc cgaggtgcag ttcaactggt acgtggatgg cgtggaggtg      840
cacaatgcca agaccaagcc aagagaggag cagtttaact ctacatacag ggtggtgagc      900
gtgctgaccg tgctgcacca ggattggctc aacggcaagg agtataagtg caaggtgtcc      960
aataagggcc tgccctcctc tatcgagaag acaatctcta aggctaaggg ccagccaaga     1020
gagcctcagg tgtacaccct gcctccaagc caggaggaga tgacaaagaa ccaggtgtcc     1080
ctgacatgtc tggtgaaggg cttctatccc tccgacatcg ccgtggagtg ggagtctaat     1140
ggccagcctg agaacaatta caagaccaca cccctgtgc tggactctga tggcagcttc     1200
tttctgtatt ccaggctgac cgtggataag tctcggtggc aggagggcaa cgtgttcagc     1260
tgctctgtga tgcacgaagc cctgcataat cactatactc agaaaagtct gtcactgtca     1320
ctgggaaag                                                             1329
```

<210> SEQ ID NO 208
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 4_IgG4 mutant TA_amino acid

<400> SEQUENCE: 208

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ser
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Ala Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```

```
<210> SEQ ID NO 209
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 4_IgG4 mutant TA_DNA

<400> SEQUENCE: 209
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactctgc gagaatggcg     300
cttgatttcg actactgggg ccagggtaca ctggtcaccg tgagctcagc cagcaccaag     360
```

-continued

```
ggcccttccg tgtttcccct ggcccctttgc tcccggtcca catctgagag caccgccgcc      420
ctgggctgtc tggtgaagga ctacttccca gagcccgtga ccgtgagctg aacagcggc       480 gccctgacaa gcggcgtgca cacatttccc gccgtgctgc agagctccgg cctgtactcc      540
ctgtctagcg tggtgacagt gccttcctct agcctgggca ccaagacata tacctgtaac      600
gtggaccaca agccaagcaa taccaaggtg ataagcgggg tggagtctaa gtacggccct      660
ccttgcccta gctgtcctgc tccagagttt ctgggcggcc cttccgtgtt cctgtttcca      720
cccaaaccaa aggacacact gatgatctct agaacaccag aggtgacctg cgtggtggtg      780
gacgtgagcc aggaggatcc cgaggtgcag ttcaactggt acgtggatgg cgtggaggtg      840
cacaatgcca agaccaagcc aagagaggag cagtttaact ctgcctacag ggtggtgagc      900
gtgctgaccg tgctgcacca ggattggctc aacggcaagg agtataagtg caaggtgtcc      960
aataagggcc tgccctcctc tatcgagaag acaatctcta aggctaaggg ccagccaaga     1020
gagcctcagg tgtacaccct gcctccaagc caggaggaga tgacaaagaa ccaggtgtcc     1080
ctgacatgtc tggtgaaggg cttctatccc tccgacatcg ccgtggagtg ggagtctaat     1140
ggccagcctg agaacaatta caagaccaca ccccctgtgc tggactctga tggcagcttc     1200
tttctgtatt ccaggctgac cgtggataag tctcggtggc aggagggcaa cgtgttcagc     1260
tgctctgtga tgcacgaagc cctgcataat cactatactc agaaaagtct gtcactgtca     1320
ctgggaaag                                                            1329
```

```
<210> SEQ ID NO 210
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG1 mutant TA_amino acid

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

-continued

```
              165             170             175
Gly Leu Tyr Ser Leu Ser Ser Val Val Thr Val Pro Ser Ser Ser Leu
            180             185             190
Gly Thr Gln Thr Tyr Ile Cys Asn Val Asn His Lys Pro Ser Asn Thr
            195             200             205
Lys Val Asp Lys Lys Val Glu Pro Lys Ser Cys Asp Lys Thr His Thr
210             215             220
Cys Pro Pro Cys Pro Ala Pro Glu Leu Leu Gly Gly Pro Ser Val Phe
225             230             235             240
Leu Phe Pro Pro Lys Pro Lys Asp Thr Leu Met Ile Ser Arg Thr Pro
            245             250             255
Glu Val Thr Cys Val Val Val Asp Val Ser His Glu Asp Pro Glu Val
            260             265             270
Lys Phe Asn Trp Tyr Val Asp Gly Val Glu Val His Asn Ala Lys Thr
            275             280             285
Lys Pro Arg Glu Glu Gln Tyr Asn Ser Ala Tyr Arg Val Val Ser Val
            290             295             300
Leu Thr Val Leu His Gln Asp Trp Leu Asn Gly Lys Glu Tyr Lys Cys
305             310             315             320
Lys Val Ser Asn Lys Ala Leu Pro Ala Pro Ile Glu Lys Thr Ile Ser
            325             330             335
Lys Ala Lys Gly Gln Pro Arg Glu Pro Gln Val Tyr Thr Leu Pro Pro
            340             345             350
Ser Arg Asp Glu Leu Thr Lys Asn Gln Val Ser Leu Thr Cys Leu Val
            355             360             365
Lys Gly Phe Tyr Pro Ser Asp Ile Ala Val Glu Trp Glu Ser Asn Gly
            370             375             380
Gln Pro Glu Asn Asn Tyr Lys Thr Thr Pro Pro Val Leu Asp Ser Asp
385             390             395             400
Gly Ser Phe Phe Leu Tyr Ser Lys Leu Thr Val Asp Lys Ser Arg Trp
            405             410             415
Gln Gln Gly Asn Val Phe Ser Cys Ser Val Met His Glu Ala Leu His
            420             425             430
Asn His Tyr Thr Gln Lys Ser Leu Ser Leu Ser Pro Gly Lys
            435             440             445
```

<210> SEQ ID NO 211
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG1 mutant TA_DNA

<400> SEQUENCE: 211

```
gaggtgcagc tgttggagtc tggggggagc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcggggctg atgggggtcc gtcttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
```

-continued

```
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaactcc tggggggacc gtcagtcttc      720
ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cgcctaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtatccctg ccccatccc gggatgagct gaccaagaac      1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                    1338
```

<210> SEQ ID NO 212
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG1 mutant LALA_amino acid

<400> SEQUENCE: 212

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

-continued

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
            210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 213
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG1 mutant LALA_DNA

<400> SEQUENCE: 213
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atcggggctg atggggggtcc gtcttattac     180 gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
```

-continued

```
gccctgacca gcggcgtgca caccttcccg gctgtcctac agtcctcagg actctactcc      540
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaagccg ccggggggacc gtcagtcttc      720 ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtatacccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338
```

```
<210> SEQ ID NO 214
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG1 mutant LALATA_amino acid

<400> SEQUENCE: 214

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
                275                 280                 285

Lys Pro Arg Glu Glu Gln Tyr Asn Ser Ala Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 215
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG1 mutant LALATA_DNA

<400> SEQUENCE: 215
gaggtgcagc tgttggagtc tgggggaggc ttggtacagc ctggggggtc cctgagactc        60
tcctgtgcag cctctggatt caccttttagc agttatgata tgagctgggt ccgccaggct       120
ccagggaagg ggctggagtg ggtctcagcg atcgggggctg atgggggtcc gtcttattac      180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctcagc ctccaccaag       360
ggcccatcgg tcttcccccct ggcaccctcc tccaagagca cctctggggg cacagcggcc      420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540

-continued

```
ctcagcagcg tggtgaccgt gccctccagc agcttgggca cccagaccta catctgcaac      600
gtgaatcaca agcccagcaa caccaaggtg gacaagaaag ttgagcccaa atcttgtgac      660
aaaactcaca catgcccacc gtgcccagca cctgaagccg ccggggggacc gtcagtcttc      720 ctcttccccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cgcctaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtataccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                    1338
```

<210> SEQ ID NO 216
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG1 mutant LALAPG_amino acid

<400> SEQUENCE: 216

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
              195                 200                 205
Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 217
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG1 mutant LALAPG_DNA

<400> SEQUENCE: 217

```
gaggtgcagc tgttggagtc tgggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atcggggctg atgggggtcc gtcttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc tccaccaag     360 ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
```

```
gtgaatcaca agcccagcaa caccaaggtg gacaagaaag ttgagcccaa atcttgtgac      660
aaaactcaca catgcccacc gtgcccagca cctgaagccg ccggggggacc gtcagtcttc      720 ctcttcccc caaaacccaa ggacaccctc atgatctccc ggacccctga ggtcacatgc      780
gtggtggtgg acgtgagcca cgaagaccct gaggtcaagt tcaactggta cgtggacggc      840
gtggaggtgc ataatgccaa gacaaagccg cgggaggagc agtacaacag cacgtaccgt      900
gtggtcagcg tcctcaccgt cctgcaccag gactggctga atggcaagga gtacaagtgc      960
aaggtctcca acaaagccct cggcgccccc atcgagaaaa ccatctccaa agccaaaggg     1020
cagccccgag aaccacaggt gtatacccctg ccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338
```

```
<210> SEQ ID NO 218
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG1 mutant LALAPGTA_amino
      acid

<400> SEQUENCE: 218

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205
```

```
Lys Val Asp Lys Lys Val Glu Pro Lys Ser Cys Asp Lys Thr His Thr
    210             215                 220

Cys Pro Pro Cys Pro Ala Pro Glu Ala Ala Gly Gly Pro Ser Val Phe
225             230                 235                 240

Leu Phe Pro Pro Lys Pro Lys Asp Thr Leu Met Ile Ser Arg Thr Pro
            245             250                 255

Glu Val Thr Cys Val Val Val Asp Val Ser His Glu Asp Pro Glu Val
            260             265                 270

Lys Phe Asn Trp Tyr Val Asp Gly Val Glu Val His Asn Ala Lys Thr
        275             280             285

Lys Pro Arg Glu Glu Gln Tyr Asn Ser Ala Tyr Arg Val Val Ser Val
    290             295             300

Leu Thr Val Leu His Gln Asp Trp Leu Asn Gly Lys Glu Tyr Lys Cys
305             310             315                 320

Lys Val Ser Asn Lys Ala Leu Gly Ala Pro Ile Glu Lys Thr Ile Ser
            325             330                 335

Lys Ala Lys Gly Gln Pro Arg Glu Pro Gln Val Tyr Thr Leu Pro Pro
            340             345                 350

Ser Arg Asp Glu Leu Thr Lys Asn Gln Val Ser Leu Thr Cys Leu Val
            355             360                 365

Lys Gly Phe Tyr Pro Ser Asp Ile Ala Val Glu Trp Glu Ser Asn Gly
    370             375                 380

Gln Pro Glu Asn Asn Tyr Lys Thr Thr Pro Pro Val Leu Asp Ser Asp
385             390                 395                 400

Gly Ser Phe Phe Leu Tyr Ser Lys Leu Thr Val Asp Lys Ser Arg Trp
            405             410                 415

Gln Gln Gly Asn Val Phe Ser Cys Ser Val Met His Glu Ala Leu His
            420             425                 430

Asn His Tyr Thr Gln Lys Ser Leu Ser Leu Ser Pro Gly Lys
        435             440             445
```

<210> SEQ ID NO 219
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG1 mutant LALAPGTA_DNA

<400> SEQUENCE: 219

```
gaggtgcagc tgttggagtc tggggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atcggggctg atggggtcc gtcttattac     180 gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca cgcggcgtgca caccttcccg gctgtcctac agtcctcagg actctactcc     540
ctcagcagcg tggtgaccgt gccctccagc agcttgggca cccagaccta catctgcaac     600
```

-continued

```
gtgaatcaca agcccagcaa caccaaggtg gacaagaaag ttgagcccaa atcttgtgac      660
aaaactcaca catgcccacc gtgcccagca cctgaagccg ccggggggacc gtcagtcttc    720 ctcttcccccc caaaacccaa ggacaccctc atgatctccc ggaccectga ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cgcctaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020 cagcccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338
```

<210> SEQ ID NO 220
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG4 wild type_amino acid

<400> SEQUENCE: 220

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
```

```
        210             215             220

Cys Pro Ala Pro Glu Phe Leu Gly Gly Pro Ser Val Phe Leu Phe Pro
225                 230             235                 240

Pro Lys Pro Lys Asp Thr Leu Met Ile Ser Arg Thr Pro Glu Val Thr
                245             250             255

Cys Val Val Val Asp Val Ser Gln Glu Asp Pro Glu Val Gln Phe Asn
                260             265             270

Trp Tyr Val Asp Gly Val Glu Val His Asn Ala Lys Thr Lys Pro Arg
            275             280             285

Glu Glu Gln Phe Asn Ser Thr Tyr Arg Val Val Ser Val Leu Thr Val
        290             295             300

Leu His Gln Asp Trp Leu Asn Gly Lys Glu Tyr Lys Cys Lys Val Ser
305             310             315             320

Asn Lys Gly Leu Pro Ser Ser Ile Glu Lys Thr Ile Ser Lys Ala Lys
                325             330             335

Gly Gln Pro Arg Glu Pro Gln Val Tyr Thr Leu Pro Pro Ser Gln Glu
            340             345             350

Glu Met Thr Lys Asn Gln Val Ser Leu Thr Cys Leu Val Lys Gly Phe
            355             360             365

Tyr Pro Ser Asp Ile Ala Val Glu Trp Glu Ser Asn Gly Gln Pro Glu
        370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
                405             410             415

Asn Val Phe Ser Cys Ser Val Met His Glu Ala Leu His Asn His Tyr
                420             425             430

Thr Gln Lys Ser Leu Ser Leu Ser Leu Gly Lys
            435             440
```

<210> SEQ ID NO 221
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG4 wild type_DNA

<400> SEQUENCE: 221

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atcgggggctg atgggggtcc gtcttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg gaacagcggc     480
gccctgacaa gcggcgtgca cacatttccc gccgtgctgc agagctccgg cctgtactcc     540
ctgtctagcg tggtgacagt gccttcctct agcctgggca ccaagacata cctgtgtaac     600
gtggaccaca gccaagcaa taccaaggtg gataagcggg tggagtctaa gtacggccct     660
```

-continued

```
ccttgccta gctgtcctgc tccagagttt ctgggcggcc cttccgtgtt cctgtttcca      720
cccaaaccaa aggacacact gatgatctct agaacaccag aggtgacctg cgtggtggtg      780
gacgtgagcc aggaggatcc cgaggtgcag ttcaactggt acgtggatgg cgtggaggtg      840
cacaatgcca agaccaagcc aagagaggag cagtttaact ctacatacag ggtggtgagc      900
gtgctgaccg tgctgcacca ggattggctc aacggcaagg agtataagtg caaggtgtcc      960
aataagggcc tgccctcctc tatcgagaag acaatctcta aggctaaggg ccagccaaga      1020
gagcctcagg tgtacaccct gcctccaagc caggaggaga tgacaaagaa ccaggtgtcc      1080
ctgacatgtc tggtgaaggg cttctatccc tccgacatcg ccgtggagtg ggagtctaat      1140
ggccagcctg agaacaatta caagaccaca ccccctgtgc tggactctga tggcagcttc      1200
tttctgtatt ccaggctgac cgtggataag tctcggtggc aggagggcaa cgtgttcagc      1260
tgctctgtga tgcacgaagc cctgcataat cactatactc agaaaagtct gtcactgtca      1320
ctgggaaag                                                              1329
```

<210> SEQ ID NO 222
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 5_IgG4 mutant TA_amino acid

<400> SEQUENCE: 222

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Gly Ala Asp Gly Gly Pro Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220
```

-continued

```
Cys Pro Ala Pro Glu Phe Leu Gly Gly Pro Ser Val Phe Leu Phe Pro
225             230             235             240

Pro Lys Pro Lys Asp Thr Leu Met Ile Ser Arg Thr Pro Glu Val Thr
            245             250             255

Cys Val Val Val Asp Val Ser Gln Glu Asp Pro Glu Val Gln Phe Asn
            260             265             270

Trp Tyr Val Asp Gly Val Glu Val His Asn Ala Lys Thr Lys Pro Arg
            275             280             285

Glu Glu Gln Phe Asn Ser Ala Tyr Arg Val Val Ser Val Leu Thr Val
            290             295             300

Leu His Gln Asp Trp Leu Asn Gly Lys Glu Tyr Lys Cys Lys Val Ser
305             310             315             320

Asn Lys Gly Leu Pro Ser Ser Ile Glu Lys Thr Ile Ser Lys Ala Lys
                325             330             335

Gly Gln Pro Arg Glu Pro Gln Val Tyr Thr Leu Pro Pro Ser Gln Glu
            340             345             350

Glu Met Thr Lys Asn Gln Val Ser Leu Thr Cys Leu Val Lys Gly Phe
            355             360             365

Tyr Pro Ser Asp Ile Ala Val Glu Trp Glu Ser Asn Gly Gln Pro Glu
            370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
                405             410             415

Asn Val Phe Ser Cys Ser Val Met His Glu Ala Leu His Asn His Tyr
                420             425             430

Thr Gln Lys Ser Leu Ser Leu Ser Leu Gly Lys
            435             440
```

<210> SEQ ID NO 223
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 5_IgG4 mutant TA_DNA

<400> SEQUENCE: 223

```
gaggtgcagc tgttggagtc tggggggaggc ttggtacagc ctggggggtc cctgagactc      60
tcctgtgcag cctctggatt caccttagc agttatgata tgagctgggt ccgccaggct     120
ccagggaagg ggctggagtg ggtctcagcg atcggggctg atgggggtcc gtcttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg gaacagcggc     480
gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca agccaagcaa taccaaggtg gataagcggg tggagtctaa gtacggccct     660
ccttgcccta gctgtcctgc tccagagttt ctgggcggcc cttccgtgtt cctgtttcca     720
```

-continued

```
cccaaaccaa aggacacact gatgatctct agaacaccag aggtgacctg cgtggtggtg    780
gacgtgagcc aggaggatcc cgaggtgcag ttcaactggt acgtggatgg cgtggaggtg    840
cacaatgcca agaccaagcc aagagaggag cagtttaact ctgcctacag ggtggtgagc    900
gtgctgaccg tgctgcacca ggattggctc aacggcaagg agtataagtg caaggtgtcc    960
aataagggcc tgccctcctc tatcgagaag acaatctcta aggctaaggg ccagccaaga   1020
gagcctcagg tgtacaccct gcctccaagc caggaggaga tgacaaagaa ccaggtgtcc   1080
ctgacatgtc tggtgaaggg cttctatccc tccgacatcg ccgtggagtg ggagtctaat   1140
ggccagcctg agaacaatta caagaccaca ccccctgtgc tggactctga tggcagcttc   1200
tttctgtatt ccaggctgac cgtggataag tctcggtggc aggagggcaa cgtgttcagc   1260
tgctctgtga tgcacgaagc cctgcataat cactatactc agaaaagtct gtcactgtca   1320
ctgggaaag                                                            1329
```

<210> SEQ ID NO 224
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG1 mutant TA_amino acid

<400> SEQUENCE: 224

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240
```

-continued

```
Leu Phe Pro Pro Lys Pro Lys Asp Thr Leu Met Ile Ser Arg Thr Pro
            245             250                 255

Glu Val Thr Cys Val Val Val Asp Val Ser His Glu Asp Pro Glu Val
            260             265                 270

Lys Phe Asn Trp Tyr Val Asp Gly Val Glu Val His Asn Ala Lys Thr
            275             280                 285

Lys Pro Arg Glu Glu Gln Tyr Asn Ser Ala Tyr Arg Val Val Ser Val
    290                 295                 300

Leu Thr Val Leu His Gln Asp Trp Leu Asn Gly Lys Glu Tyr Lys Cys
305             310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 225
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG1 mutant TA_DNA

<400> SEQUENCE: 225

```
gaggtgcagc tgttggagtc tgggggaggc ttggtacagc ctggggggtc cctgagactc        60
tcctgtgcag cctctggatt cacctttagc agttatgata tgagctgggt ccgccaggct       120
ccagggaagg ggctggagtg ggtctcagcg atctctccgt attcgggtag gatttattac       180
gctgattctg taaaaggtcg gttcaccatc tccagagaca attccaagaa cacgctgtat       240
ctgcaaatga acagcctgag agccgaggac acggccgtgt attactgtgc gagaatggcg       300
cttgatttcg actactgggg ccagggtaca ctggtcaccg tgagctcagc ctccaccaag       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaactcc tggggggacc gtcagtcttc       720
ctcttccccc caaaacccaa ggacaccctc atgatctccc ggacccctga ggtcacatgc       780
```

-continued

```
gtggtggtgg acgtgagcca cgaagaccct gaggtcaagt tcaactggta cgtggacggc      840
gtggaggtgc ataatgccaa gacaaagccg cgggaggagc agtacaacag cgcctaccgt      900
gtggtcagcg tcctcaccgt cctgcaccag gactggctga atggcaagga gtacaagtgc      960
aaggtctcca acaaagccct cccagccccc atcgagaaaa ccatctccaa agccaaaggg     1020
cagccccgag aaccacaggt gtataccctg cccccatccc gggatgagct gaccaagaac     1080
caggtcagcc tgacctgcct ggtcaaaggc ttctatccca gcgacatcgc cgtggagtgg     1140
gagagcaatg ggcagccgga gaacaactac aagaccacgc ctcccgtgct ggactccgac     1200
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                   1338
```

```
<210> SEQ ID NO 226
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG1 mutant LALA_amino acid

<400> SEQUENCE: 226

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
```

-continued

```
                     245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445
```

<210> SEQ ID NO 227
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG1 mutant LALA_DNA

<400> SEQUENCE: 227

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggaccc gtcagtcttc     720 ctcttcccc caaaacccaa ggacaccctc atgatctccc ggaccctga ggtcacatgc     780 gtggtggtgg acgtgagcca cgaagaccct gaggtcaagt tcaactggta cgtggacggc     840
```

```
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtatacoctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338
```

<210> SEQ ID NO 228
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG1 mutant LALATA_amino acid

<400> SEQUENCE: 228

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 229
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG1 mutant LALATA_DNA

<400> SEQUENCE: 229

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttcccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
```

```
gtggtcagcg tcctcaccgt cctgcaccag gactggctga atggcaagga gtacaagtgc    960
aaggtctcca acaaagccct cccagccccc atcgagaaaa ccatctccaa agccaaaggg   1020
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                  1338
```

```
<210> SEQ ID NO 230
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG1 mutant LALAPG_amino acid

<400> SEQUENCE: 230

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

-continued

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

```
<210> SEQ ID NO 231
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG1 mutant LALAPG_DNA

<400> SEQUENCE: 231
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gattttttac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
```

```
aaggtctcca acaaagccct cggcgccccc atcgagaaaa ccatctccaa agccaaaggg    1020
cagccccgag aaccacaggt gtatacccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                  1338
```

```
<210> SEQ ID NO 232
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG1 mutant LALAPGTA_amino
      acid

<400> SEQUENCE: 232

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
        275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

```
<210> SEQ ID NO 233
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG1 mutant LALAPGTA_DNA

<400> SEQUENCE: 233
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc tccaccaag      360 ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttccccc caaaacccaa ggacaccctc atgatctccc ggaccccctga ggtcacatgc     780 gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900 gtggtcagc tcctcaccgt cctgcaccag gactggctga atggcaagga gtacaagtgc     960
aaggtctcca acaaagccct cggcgccccc atcgagaaaa ccatctccaa agccaaaggg    1020
```

-continued

```
cagccccgag aaccacaggt gtataccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtccc cgggtaaa                                                 1338
```

```
<210> SEQ ID NO 234
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG4 wild type_amino acid

<400> SEQUENCE: 234
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285
```

```
Glu Glu Gln Phe Asn Ser Thr Tyr Arg Val Val Ser Val Leu Thr Val
    290                 295             300

Leu His Gln Asp Trp Leu Asn Gly Lys Glu Tyr Lys Cys Lys Val Ser
305                 310             315                 320

Asn Lys Gly Leu Pro Ser Ser Ile Glu Lys Thr Ile Ser Lys Ala Lys
            325                 330             335

Gly Gln Pro Arg Glu Pro Gln Val Tyr Thr Leu Pro Pro Ser Gln Glu
            340                 345             350

Glu Met Thr Lys Asn Gln Val Ser Leu Thr Cys Leu Val Lys Gly Phe
        355                 360             365

Tyr Pro Ser Asp Ile Ala Val Glu Trp Glu Ser Asn Gly Gln Pro Glu
    370                 375             380

Asn Asn Tyr Lys Thr Thr Pro Pro Val Leu Asp Ser Asp Gly Ser Phe
385                 390                 395             400

Phe Leu Tyr Ser Arg Leu Thr Val Asp Lys Ser Arg Trp Gln Glu Gly
            405                 410             415

Asn Val Phe Ser Cys Ser Val Met His Glu Ala Leu His Asn His Tyr
            420                 425             430

Thr Gln Lys Ser Leu Ser Leu Ser Leu Gly Lys
        435                 440
```

```
<210> SEQ ID NO 235
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG4 wild type_DNA

<400> SEQUENCE: 235
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tcccggtcca tctgagagag caccgccgcc     420
ctgggctgtc tggtgaagga ctacttccca gagcccgtga ccgtgagctg gaacagcggc     480
gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct      660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca gaccaagcc aagagaggag cagtttaact ctacatacag ggtggtgagc     900
gtgctgaccg tgctgcacca ggattggctc aacggcaagg agtataagtg caaggtgtcc     960 aataagggc tgccctcctc tatcgagaag acaatctcta aggctaaggg ccagccaaga    1020
gagcctcagg tgtacacccct gcctccaagc caggaggaga tgacaaagaa ccaggtgtcc    1080
```

-continued

```
ctgacatgtc tggtgaaggg cttctatccc tccgacatcg ccgtggagtg ggagtctaat    1140
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                            1329
```

<210> SEQ ID NO 236
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 6_IgG4 mutant TA_amino acid

<400> SEQUENCE: 236

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Met Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Ala Tyr Arg Val Val Ser Val Leu Thr Val
```

-continued

```
          290               295               300
Leu His Gln Asp Trp Leu Asn Gly Lys Glu Tyr Lys Cys Lys Val Ser
305               310               315               320

Asn Lys Gly Leu Pro Ser Ser Ile Glu Lys Thr Ile Ser Lys Ala Lys
              325               330               335

Gly Gln Pro Arg Glu Pro Gln Val Tyr Thr Leu Pro Pro Ser Gln Glu
              340               345               350

Glu Met Thr Lys Asn Gln Val Ser Leu Thr Cys Leu Val Lys Gly Phe
          355               360               365

Tyr Pro Ser Asp Ile Ala Val Glu Trp Glu Ser Asn Gly Gln Pro Glu
          370               375               380

Asn Asn Tyr Lys Thr Thr Pro Pro Val Leu Asp Ser Asp Gly Ser Phe
385               390               395               400

Phe Leu Tyr Ser Arg Leu Thr Val Asp Lys Ser Arg Trp Gln Glu Gly
              405               410               415

Asn Val Phe Ser Cys Ser Val Met His Glu Ala Leu His Asn His Tyr
              420               425               430

Thr Gln Lys Ser Leu Ser Leu Ser Leu Gly Lys
          435               440
```

```
<210> SEQ ID NO 237
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 6_IgG4 mutant TA_DNA

<400> SEQUENCE: 237
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagaatggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg gaacagcggc     480
gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggcccct     660 ccttgcccta gctgtcctgc tccagagttt ctgggcggcc cttccgtgtt cctgtttcca     720
cccaaaccaa aggacacact gatgatctct agaaccaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctgcctacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
```

-continued

```
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                            1329
```

```
<210> SEQ ID NO 238
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG1 mutant TA_amino acid

<400> SEQUENCE: 238

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Ala Tyr Arg Val Val Ser Val
    290                 295                 300
```

-continued

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 239
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG1 mutant TA_DNA

<400> SEQUENCE: 239
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc ctccaccaag     360
ggcccatcgg tcttcccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaactcc tggggggacc gtcagtcttc     720 ctcttcccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtatacccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
```

-continued

```
ggctccttct tcctctacag caagctcacc gtggacaaga gcaggtggca gcaggggaac     1260
gtcttctcat gctccgtgat gcatgaggct ctgcacaacc actacacgca gaagagcctc     1320
tccctgtccc cgggtaaa                                                    1338
```

<210> SEQ ID NO 240
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG1 mutant LALA_amino acid

<400> SEQUENCE: 240

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320
```

```
Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

```
<210> SEQ ID NO 241
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG1 mutant LALA_DNA

<400> SEQUENCE: 241
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccggggggacc gtcagtcttc     720 ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cacgtaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
```

-continued

```
gtcttctcat gctccgtgat gcatgaggct ctgcacaacc actacacgca gaagagcctc      1320
tccctgtccc cgggtaaa                                                    1338
```

<210> SEQ ID NO 242
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG1 mutant LALATA_amino acid

<400> SEQUENCE: 242

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

-continued

```
              325              330              335
Lys Ala Lys Gly Gln Pro Arg Glu Pro Gln Val Tyr Thr Leu Pro Pro
            340              345              350

Ser Arg Asp Glu Leu Thr Lys Asn Gln Val Ser Leu Thr Cys Leu Val
            355              360              365

Lys Gly Phe Tyr Pro Ser Asp Ile Ala Val Glu Trp Glu Ser Asn Gly
            370              375              380

Gln Pro Glu Asn Asn Tyr Lys Thr Thr Pro Pro Val Leu Asp Ser Asp
        385              390              395              400

Gly Ser Phe Phe Leu Tyr Ser Lys Leu Thr Val Asp Lys Ser Arg Trp
                405              410              415

Gln Gln Gly Asn Val Phe Ser Cys Ser Val Met His Glu Ala Leu His
                420              425              430

Asn His Tyr Thr Gln Lys Ser Leu Ser Leu Ser Pro Gly Lys
            435              440              445

<210> SEQ ID NO 243
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG1 mutant LALALTA_DNA

<400> SEQUENCE: 243
gaggtgcagc tgttggagtc tggggggaggc ttggtacagc ctgggggggtc cctgagactc      60 tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg ccgggggacc gtcagtcttc     720
ctcttccccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cccagccccc atcgagaaaa ccatctccaa agccaaaggg    1020
cagccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
```
tccctgtccc cgggtaaa                                        1338

<210> SEQ ID NO 244
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG1 mutant LALAPG_amino acid

<400> SEQUENCE: 244

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

```
Lys Ala Lys Gly Gln Pro Arg Glu Pro Gln Val Tyr Thr Leu Pro Pro
            340             345             350

Ser Arg Asp Glu Leu Thr Lys Asn Gln Val Ser Leu Thr Cys Leu Val
            355             360             365

Lys Gly Phe Tyr Pro Ser Asp Ile Ala Val Glu Trp Glu Ser Asn Gly
            370             375             380

Gln Pro Glu Asn Asn Tyr Lys Thr Thr Pro Pro Val Leu Asp Ser Asp
        385             390             395             400

Gly Ser Phe Phe Leu Tyr Ser Lys Leu Thr Val Asp Lys Ser Arg Trp
                405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

```
<210> SEQ ID NO 245
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG1 mutant LALAPG_DNA

<400> SEQUENCE: 245
gaggtgcagc tgttggagtc tggggggaggc ttggtacagc ctgggggggtc cctgagactc        60 tcctgtgcag cctctggatt caccttttagc agttatgata tgagctgggt ccgccaggct       120
ccagggaagg ggctggagtg ggtctcagcg atctctccgt attcgggtag gatttattac       180
gctgattctg taaaaggtcg gttcaccatc tccagagaca attccaagaa cacgctgtat       240
ctgcaaatga acagcctgag agccgaggac acggccgtgt attactgtgc gagactggcg       300
cttgatttcg actactgggg ccagggtaca ctggtcaccg tgagctcagc ctccaccaag       360
ggcccatcgg tcttcccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaggtg gacaagaaag ttgagcccaa atcttgtgac       660
aaaactcaca catgcccacc gtgcccagca cctgaagccg ccgggggacc gtcagtcttc       720
ctcttccccc caaaacccaa ggacaccctc atgatctccc ggacccctga ggtcacatgc       780
gtggtggtgg acgtgagcca cgaagaccct gaggtcaagt tcaactggta cgtggacggc       840
gtggaggtgc ataatgccaa gacaaagccg cgggaggagc agtacaacag cacgtaccgt       900
gtggtcagcg tcctcaccgt cctgcaccag gactggctga atggcaagga gtacaagtgc       960
aaggtctcca caaagcccct cggcgccccc atcgagaaaa ccatctccaa agccaaaggg      1020
cagccccgag aaccacaggt gtataccctg cccccatccc gggatgagct gaccaagaac      1080
caggtcagcc tgacctgcct ggtcaaaggc ttctatccca gcgacatcgc cgtggagtgg      1140
gagagcaatg ggcagccgga gaacaactac aagaccacgc ctcccgtgct ggactccgac      1200
ggctccttct tcctctacag caagctcacc gtggacaaga gcaggtggca gcaggggaac      1260
gtcttctcat gctccgtgat gcatgaggct ctgcacaacc actacacgca gaagagcctc      1320
tccctgtccc cgggtaaa                                                    1338
```

```
<210> SEQ ID NO 246
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG1 mutant LALAPGTA_amino
      acid

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Ala Ile Ser Pro Tyr Ser Gly Arg Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Ala Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
            325                 330                 335

Lys Ala Lys Gly Gln Pro Arg Glu Pro Gln Val Tyr Thr Leu Pro Pro
```

```
            340             345             350
Ser Arg Asp Glu Leu Thr Lys Asn Gln Val Ser Leu Thr Cys Leu Val
        355             360             365

Lys Gly Phe Tyr Pro Ser Asp Ile Ala Val Glu Trp Glu Ser Asn Gly
        370             375             380

Gln Pro Glu Asn Asn Tyr Lys Thr Thr Pro Pro Val Leu Asp Ser Asp
385             390             395             400

Gly Ser Phe Phe Leu Tyr Ser Lys Leu Thr Val Asp Lys Ser Arg Trp
            405             410             415

Gln Gln Gly Asn Val Phe Ser Cys Ser Val Met His Glu Ala Leu His
            420             425             430

Asn His Tyr Thr Gln Lys Ser Leu Ser Leu Ser Pro Gly Lys
            435             440             445
```

<210> SEQ ID NO 247
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG1 mutant LALAPGTA_DNA

<400> SEQUENCE: 247

```
gaggtgcagc tgttggagtc tggggggaggc ttggtacagc ctggggggtc cctgagactc      60
tcctgtgcag cctctggatt caccttttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc ctccaccaag     360
ggcccatcgg tcttccccct ggcaccctcc tccaagagca cctctggggg cacagcggcc     420
ctgggctgcc tggtcaagga ctacttcccc gaaccggtga cggtgtcgtg gaactcaggc     480
gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca agcccagcaa caccaaggtg gacaagaaag ttgagcccaa atcttgtgac     660
aaaactcaca catgcccacc gtgcccagca cctgaagccg cggggggacc gtcagtcttc     720 ctcttcccc caaaacccaa ggacaccctc atgatctccc ggacccctga ggtcacatgc     780
gtggtggtgg acgtgagcca cgaagaccct gaggtcaagt tcaactggta cgtggacggc     840
gtggaggtgc ataatgccaa gacaaagccg cgggaggagc agtacaacag cgcctaccgt     900
gtggtcagcg tcctcaccgt cctgcaccag gactggctga atggcaagga gtacaagtgc     960
aaggtctcca acaaagccct cggcgccccc atcgagaaaa ccatctccaa agccaaaggg    1020 cagcccccgag aaccacaggt gtataccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct tcctctacag caagctcacc gtggacaaga gcaggtggca gcaggggaac    1260
gtcttctcat gctccgtgat gcatgaggct ctgcacaacc actacacgca gaagagcctc    1320
tccctgtccc cgggtaaa                                                   1338
```

-continued

<210> SEQ ID NO 248
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG4 wild type_amino acid

<400> SEQUENCE: 248

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Ser
        210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

-continued

```
Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly Lys
        435                 440
```

```
<210> SEQ ID NO 249
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG4 wild type_DNA

<400> SEQUENCE: 249
gaggtgcagc tgttggagtc tggggggaggc ttggtacagc ctggggggtc cctgagactc      60
tcctgtgcag cctctggatt cacctttagc agttatgata tgagctgggt ccgccaggct     120
ccagggaagg ggctggagtg ggtctcagcg atctctccgt attcgggtag gatttattac     180
gctgattctg taaaaggtcg gttcaccatc tccagagaca attccaagaa cacgctgtat     240
ctgcaaatga acagcctgag agccgaggac acggccgtgt attactgtgc gagactggcg     300
cttgatttcg actactgggg ccagggtaca ctggtcaccg tgagctcagc cagcaccaag     360
ggcccttccg tgtttcccct ggcccccttgc tcccggtcca catctgagag caccgccgcc     420
ctgggctgtc tggtgaagga ctacttccca gagcccgtga ccgtgagctg gaacagcggc     480
gccctgacaa gcggcgtgca cacatttccc gccgtgctgc agagctccgg cctgtactcc     540
ctgtctagcg tggtgacagt gccttcctct agcctgggca ccaagacata tacctgtaac     600
gtggaccaca gccaagcaa taccaaggtg gataagcggg tggagtctaa gtacggccct     660
ccttgcccta gctgtcctgc tccagagttt ctgggcggcc cttccgtgtt cctgtttcca     720
cccaaaccaa aggacacact gatgatctct agaacaccag aggtgacctg cgtggtggtg     780
gacgtgagcc aggaggatcc cgaggtgcag ttcaactggt acgtggatgg cgtggaggtg     840
cacaatgcca agaccaagcc aagagaggag cagtttaact ctacatacag ggtggtgagc     900
gtgctgaccg tgctgcacca ggattggctc aacggcaagg agtataagtg caaggtgtcc     960
aataagggcc tgccctcctc tatcgagaag acaatctcta aggctaaggg ccagccaaga    1020
gagcctcagg tgtacaccct gcctccaagc caggaggaga tgacaaagaa ccaggtgtcc    1080
ctgacatgtc tggtgaaggg cttctatccc tccgacatcg ccgtggagtg ggagtctaat    1140
ggccagcctg agaacaatta caagaccaca ccccctgtgc tggactctga tggcagcttc    1200
tttctgtatt ccaggctgac cgtggataag tctcggtggc aggagggcaa cgtgttcagc    1260
tgctctgtga tgcacgaagc cctgcataat cactatactc agaaaagtct gtcactgtca    1320
ctgggaaag                                                             1329
```

```
<210> SEQ ID NO 250
```

-continued

```
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: IgG heavy chain 7_IgG4 mutant TA_amino acid

<400> SEQUENCE: 250

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Pro Tyr Ser Gly Arg Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Leu Asp Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Ser
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Ala Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365
```

Tyr Pro Ser Asp Ile Ala Val Glu Trp Glu Ser Asn Gly Gln Pro Glu
    370             375             380

Asn Asn Tyr Lys Thr Thr Pro Pro Val Leu Asp Ser Asp Gly Ser Phe
385             390             395             400

Phe Leu Tyr Ser Arg Leu Thr Val Asp Lys Ser Arg Trp Gln Glu Gly
            405             410             415

Asn Val Phe Ser Cys Ser Val Met His Glu Ala Leu His Asn His Tyr
            420             425             430

Thr Gln Lys Ser Leu Ser Leu Ser Leu Gly Lys
        435             440

<210> SEQ ID NO 251
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: IgG heavy chain 7_IgG4 mutant TA_DNA

<400> SEQUENCE: 251
gaggtgcagc tgttggagtc tggggggaggc ttggtacagc ctgggggggtc cctgagactc        60 tcctgtgcag cctctggatt caccttttagc agttatgata tgagctgggt ccgccaggct       120
ccagggaagg ggctggagtg ggtctcagcg atctctccgt attcgggtag gatttattac       180
gctgattctg taaaaggtcg gttcaccatc tccagagaca attccaagaa cacgctgtat       240
ctgcaaatga acagcctgag agccgaggac acggccgtgt attactgtgc gagactggcg       300
cttgatttcg actactgggg ccagggtaca ctggtcaccg tgagctcagc cagcaccaag       360
ggcccttccg tgtttcccct ggcccccttgc tcccggtcca catctgagag caccgccgcc       420
ctgggctgtc tggtgaagga ctacttccca gagcccgtga ccgtgagctg gaacagcggc       480
gccctgacaa gcggcgtgca cacatttccc gccgtgctgc agagctccgg cctgtactcc       540
ctgtctagcg tggtgacagt gccttcctct agcctgggca ccaagacata tacctgtaac       600
gtggaccaca gccaagcaa taccaaggtg gataagcggg tggagtctaa gtacggcccct       660 ccttgcccta gctgtcctgc tccagagttt ctgggcggcc cttccgtgtt cctgtttcca       720
cccaaaccaa aggacacact gatgatctct agaacaccag aggtgacctg cgtggtggtg       780
gacgtgagcc aggaggatcc cgaggtgcag ttcaactggt acgtggatgg cgtggaggtg       840
cacaatgcca gaccaagcc aagagaggag cagtttaact ctgcctacag ggtggtgagc       900
gtgctgaccg tgctgcacca ggattggctc aacggcaagg agtataagtg caaggtgtcc       960
aataagggcc tgcctcctc tatcgagaag acaatctcta aggctaaggg ccagcccaaga      1020 gagcctcagg tgtacacccct gcctccaagc caggaggaga tgacaaagaa ccaggtgtcc      1080
ctgacatgtc tggtgaaggg cttctatccc tccgacatcg ccgtggagtg ggagtctaat      1140
ggccagcctg agaacaatta caagaccaca ccccctgtgc tggactctga tggcagcttc      1200
tttctgtatt ccaggctgac cgtggataag tctcggtggc aggagggcaa cgtgttcagc      1260
tgctctgtga tgcacgaagc cctgcataat cactatactc agaaaagtct gtcactgtca      1320
ctgggaaag                                                             1329

<210> SEQ ID NO 252
<211> LENGTH: 17
<212> TYPE: PRT

-continued

```
<213> ORGANISM: Artificial
<220> FEATURE:
<223> OTHER INFORMATION: heavy chain complementarity determining region
      2 wherein X1 is A or V, X2 is S, D or G, X3 is Y, P, S or A and X4
      is D, Q, L or Y, X5 is N, M, S, or G, X6 is N, R or P, X7 is T, V,
      I or S
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 252

Xaa Ile Xaa Xaa Xaa Xaa Gly Xaa Xaa Tyr Tyr Ala Asp Ser Val Lys
1               5                   10                  15

Gly

<210> SEQ ID NO 253
<211> LENGTH: 7
<212> TYPE: PRT
<213> ORGANISM: Artificial
<220> FEATURE:
<223> OTHER INFORMATION: heavy chain complementarity determining region
      3 wherein X is M or L
<220> FEATURE:
<221> NAME/KEY: misc_feature
<222> LOCATION: (1)..(1)
<223> OTHER INFORMATION: Xaa can be any naturally occurring amino acid

<400> SEQUENCE: 253

Xaa Ala Leu Asp Phe Asp Tyr
1               5

<210> SEQ ID NO 254
<211> LENGTH: 7
<212> TYPE: PRT
<213> ORGANISM: Artificial
<220> FEATURE:
<223> OTHER INFORMATION: light chain complementarity determining region
      2 wherein X9 is D, S or R, X10 is S or N, and X11 is N or Q
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 254

Xaa Asn Xaa Xaa Arg Pro Ser
1               5

<210> SEQ ID NO 255
<211> LENGTH: 11
<212> TYPE: PRT
<213> ORGANISM: Artificial
<220> FEATURE:
<223> OTHER INFORMATION: light chain complementarity determining region
      3 wherein X12 is A or S
<220> FEATURE:
<221> NAME/KEY: misc_feature
<222> LOCATION: (1)..(1)
<223> OTHER INFORMATION: Xaa can be any naturally occurring amino acid
```

-continued

```
<400> SEQUENCE: 255

Xaa Ser Phe Ser Asp Glu Leu Gly Ala Tyr Val
1               5                   10
```

ANTIBODY FOR SPECIFICALLY BINDING TO LYSYL-TRNA SYNTHETASE N-TERMINAL DOMAIN EXPOSED TO EXTRACELLULAR MEMBRANE

RELATED APPLICATION DATA

This application is a National Stage Application under 35 U.S.C. 371 of co-pending PCT application number PCT/KR2019/011998 designating the United States and filed Sep. 17, 2019; which claims the benefit of KR application number 10-2018-0111046 and filed Sep. 17, 2018 each of which are hereby incorporated by reference in their entireties.

The present invention relates to an antibody that specifically binds to the lysyl-tRNA synthase N-terminal domain exposed to the extracellular membrane, more specifically, it specifically binds to the lysyl-tRNA synthetase (KRS, Lysyl-tRNA synthetase)N-terminal domain exposed to the extracellular membrane having a specific CDR (complementarity determining region) sequence described herein, and relates to the use for the prevention, treatment or diagnosis of cancer, cancer metastasis, or diseases related to immune cell migration of a composition comprising an antibody or fragment thereof having high affinity and stability or the antibody and fragment thereof as an active ingredient.

SEQUENCE LISTING

The instant application contains a Sequence Listing which has been submitted electronically in ASCII format and is hereby incorporated by reference in its entirety. Said ASCII copy, created on Jan. 29, 2024, is named 009041_00006_US_SL_updated.txt and is 531,045 bytes in size.

BACKGROUND OF THE INVENTION

Recent studies have established that human lysyl-tRNA synthetase (KRS) generally present in the cytosol translocates to the plasma membrane (cell membrane) to interact with a 67-kDa laminin receptor (67LR) present on the plasma membrane, thereby promoting the migration of tumor (or cancer) cells to affect cancer metastasis (Dae Gyu Kim et al., Chemical inhibition of prometastatic lysyl-tRNA synthetase-laminin receptor interaction, Nat Chem Biol. 2014 January; 10 (1): 29-34, Dae Gyu Kim et. al. Interaction of two translational components, lysyl-tRNA synthetase and p40/37LRP, in plasma membrane promotes laminin-dependent cell migration, FASEB J. (2012) 26, 4142-4159). Human KRS (Genbank Accession No. NP_005539.1, etc) comprises an N-terminal extension (1-72), an anticodon-binding domain (73-209), and a catalytic domain (220-597). Human KRS is an enzyme essential for protein synthesis, and normally resides within the multi-tRNA synthetase complex (MSC) in the cytosol. However, after the introduction of laminin signal, p38 MAPK phosphorylates KRS at the T52 residues, and KRS translocates to the cell membrane, where KRS protects 67LR from ubiquitin-mediated degradation. It has also been reported that KRS translocated to the cell membrane accelerates cancer metastasis by stabilizing and interacting with 67LR associated with cancer metastasis.

At this time, the fact that Myc-KRS41-597 (ΔN) with a deletion of 40 terminal residues in N-terminal extension (N-ext) is not localized on the plasma membrane indicates that the KRS N-ext region is an essential region in the translocation of KRS to the cell membrane. As for cancer metastasis, specifically, the KRS N-ext region has been known to be involved in the binding of KRS and 67LR in the interaction thereof. To use this fact for therapeutic or diagnostic purposes, it is necessary to specifically target a particular site (especially, KRS N-ext) in the KRS protein according to the characteristics of several domains constituting the KRS protein. Accordingly, the present inventors produced an antibody that specifically binds to the KRS N-terminus, which does not show a cross-reaction that also binds to ARS (Korean Patent Application No. 10-2018-0035446).

However, the affinity of previous antibodies targeting KRS N-terminus is lower than that of various antibodies in the complete IgG form. Therefore, there is a need to construct an antibody having a higher affinity for the KRS N-terminus.

DETAILED DESCRIPTION OF THE INVENTION

Technical Problem

Therefore, the present invention was completed by modifying the existing antibody light chain variable region and heavy chain variable region, in order to produce an antibody having a better binding affinity to the KRS N-terminal domain than the existing antibody that specifically binds to the KRS N-terminal domain exposed to the extracellular membrane.

Therefore, the object of the present invention is to provide that an antibody or fragment thereof that specifically binds to an extracellularly exposed lysyl-tRNA synthetase (KRS, Lysyl-tRNA synthetase)N-terminal region, the antibody or fragment thereof comprises:

(a) a heavy chain variable region (VH) comprising
  (i) heavy chain complementarity determining region 1 (CDR1) containing the amino acid sequence SYDMS (SEQ ID NO: 1);
  (ii) heavy chain complementarity determining region 2 (CDR2) containing the amino acid sequence $X_1IX_2X_3X_4X_5GX_6X_7YYADSVKG$ (SEQ ID NO: 252), and wherein $X_1$ is A or V, $X_2$ is S, D or G, $X_3$ is Y, P, S or A and $X_4$ is D, Q, L or Y, $X_5$ is N, M, S, or G, $X_6$ is N, R or P, $X_7$ is T, V, I or S; and
  (iii) heavy chain complementarity determining region 3 (CDR3) containing an amino acid sequence $X_8ALDFDY$ (SEQ ID NO: 253), and wherein $X_8$ is M or L, and (b) a light chain variable region (VL) comprising
  (i) light chain complementarity determining region 1 (CDR1) containing the amino acid sequence TGSSSNIGSNYVT (SEQ ID NO: 7);
  (ii) light chain complementarity determining region 2 (CDR2) comprising amino acid sequence $X_9NX_{10}X_{11}RPS$ (SEQ ID NO: 254), wherein $X_9$ is D, S or R, $X_{10}$ is S or N, and $X_{11}$ is N or Q; and
  (iii) light chain complementarity determining region 3 (CDR3) containing an amino acid sequence $X_{12}SFSDELGAYV$ (SEQ ID NO: 255), and wherein $X_{12}$ is A or S.

Another object of the present invention is to provide a polynucleotide encoding an antibody or fragment thereof, a recombinant expression vector comprising the polynucleotide, and a cell transformed with the vector.

Another object of the present invention is to provide that a method for producing an antibody or fragment thereof specifically binding to an extracellularly exposed lysyl-tRNA synthetase (KRS)N-terminal region, the method comprising:

(a) transforming host cells with the recombinant expression vector;

(b) incubating the transformed host cells to produce an antibody or fragment thereof; and (c) collecting the antibody or fragment thereof produced in the host cells.

Another object of the present invention is to provide a pharmaceutical composition for preventing or inhibiting cancer and cancer metastasis comprising the antibody or fragment thereof as an active ingredient.

In addition, another object of the present invention is to provide a pharmaceutical composition for preventing or inhibiting cancer metastasis consisting of the antibody or fragment thereof as an active ingredient.

In addition, another object of the present invention is to provide a pharmaceutical composition for preventing or inhibiting cancer metastasis consisting essentially of the antibody or fragment thereof as an active ingredient.

Another object of the present invention is to provide a composition for prevention or treatment of an immune cell migration-related disease comprising the antibody or fragment thereof as an active ingredient.

In addition, another object of the present invention is to provide a composition for prevention or treatment of an immune cell migration-related disease consisting of the antibody or fragment thereof as an active ingredient.

In addition, another object of the present invention is to provide a composition for prevention or treatment of an immune cell migration-related disease consisting essentially of the antibody or fragment thereof as an active ingredient.

Another object of the present invention is to provide a composition for diagnosing of an immune cell migration-related disease comprising the antibody or fragment thereof as an active ingredient.

In addition, another object of the present invention is to provide a composition for diagnosing of an immune cell migration-related disease consisting of the antibody or fragment thereof as an active ingredient.

In addition, another object of the present invention is to provide a composition for diagnosing of an immune cell migration-related disease consisting essentially of the antibody or fragment thereof as an active ingredient.

Another object of the present invention is to provide use of the antibody or fragment thereof for preparing an agent for preventing or inhibiting cancer and cancer metastasis.

Another object of the present invention is to provide a method for preventing or inhibiting cancer and cancer metastasis, administering an effective amount of a composition comprising the antibody or fragment thereof to a subject in need thereof.

Another object of the present invention is to provide a use of the antibody or fragment thereof for preparing an agent for cancer or cancer metastasis diagnosis.

Another object of the present invention is to provide that a method for diagnosing cancer or cancer metastasis, the method comprising:

a) obtaining a biological sample from an individual (subject) suspected of cancer metastasis;

b) administering a composition comprising the antibody or a fragment thereof to the sample or subject;

c) detecting the expression level of the KRS protein in the sample or subject of step b); and

d) comparing the expression level of the KRS protein with a normal control group, and diagnosing that cancer and cancer metastasis have occurred when the expression level of KRS is increased.

Another object of the present invention is to provide use of the antibody or fragment thereof for preparing an agent for treatment of an immune cell migration-related disease.

Another object of the present invention is to provide a method for treating an immune cell migration-related disease, administering an effective amount of a composition comprising the antibody or fragment thereof to a subject in need thereof.

Another object of the present invention is to provide use of the antibody or fragment thereof of claim 1 for preparing an agent for diagnosis of an immune cell migration-related disease.

Another object of the present invention is to provide that a method for diagnosing an immune cell migration-related disease, the method comprising:

a) obtaining a biological sample from a subject suspected of an immune cell migration-related disease;

b) administering a composition comprising the antibody or a fragment thereof to the sample or subject;

c) detecting the expression level of the KRS protein in the sample or subject of step b); and d) comparing the expression level of the KRS protein with a normal control group, and diagnosing as an immune cell migration-related disease when the expression level of KRS is increased.

Technical Solution

In order to achieve the above object, the present invention provides that an antibody or fragment thereof that specifically binds to an extracellularly exposed lysyl-tRNA synthetase (KRS, Lysyl-tRNA synthetase)N-terminal region, the antibody or fragment thereof comprises:

(a) a heavy chain variable region (VH) comprising (i) heavy chain complementarity determining region 1 (CDR1) containing the amino acid sequence SYDMS (SEQ ID NO: 1);

(ii) heavy chain complementarity determining region 2 (CDR2) containing the amino acid sequence $X_1IX_2X_3X_4X_5GX_6X_7YYADSVKG$, and wherein $X_1$ is A or V, $X_2$ is S, D or G, $X_3$ is Y, P, S or A and $X_4$ is D, Q, L or Y, $X_5$ is N, M, S, or G, $X_6$ is N, R or P, $X_7$ is T, V, I or S; and (iii) heavy chain complementarity determining region 3 (CDR3) containing an amino acid sequence $X_8$ALDFDY (SEQ ID NO: 253), and wherein $X_8$ is M or L, and (b) a light chain variable region (VL) comprising (i) light chain complementarity determining region 1 (CDR1) containing the amino acid sequence TGSSSNIGSNYVT (SEQ ID NO: 7);

(ii) light chain complementarity determining region 2 (CDR2) comprising amino acid sequence $X_9NX_{10}X_{11}RPS$ (SEQ ID NO: 254), wherein $X_9$ is D, S or R, $X_{10}$ is S or N, and $X_{11}$ is N or Q; and (iii) light chain complementarity determining region 3 (CDR3) containing an amino acid sequence $X_{12}$SFSDELGAYV (SEQ ID NO: 255), and wherein $X_{12}$ is A or S.

In order to achieve the above object, the present invention provides a polynucleotide encoding an antibody or fragment thereof, a recombinant expression vector comprising the polynucleotide, and a cell transformed with the vector.

Still another aspect of the present invention is to provide a method for producing an antibody or fragment thereof specifically binding to an extracellularly exposed lysyl-tRNA synthetase (KRS)N-terminal region, the method comprising:

(a) transforming host cells with the recombinant expression vector;

(b) incubating the transformed host cells to produce an antibody or fragment thereof; and (c) collecting the antibody or fragment thereof produced in the host cells.

To achieve another object of the present invention, the present invention provides a pharmaceutical composition for preventing or inhibiting cancer and cancer metastasis comprising the antibody or fragment thereof as an active ingredient.

In addition, the present invention provides a pharmaceutical composition for preventing or inhibiting cancer metastasis consisting of the antibody or fragment thereof as an active ingredient.

In addition, the present invention provides a pharmaceutical composition for preventing or inhibiting cancer metastasis consisting essentially of the antibody or fragment thereof as an active ingredient.

To achieve another object of the present invention, the present invention provides a composition for prevention or treatment of an immune cell migration-related disease comprising the antibody or fragment thereof as an active ingredient.

In addition, the present invention provides a composition for prevention or treatment of an immune cell migration-related disease consisting of the antibody or fragment thereof as an active ingredient.

In addition, the present invention provides a composition for prevention or treatment of an immune cell migration-related disease consisting essentially of the antibody or fragment thereof as an active ingredient.

To achieve another object of the present invention, present invention provides a composition for diagnosing of an immune cell migration-related disease comprising the antibody or fragment thereof as an active ingredient.

In addition, the present invention provides a composition for diagnosing of an immune cell migration-related disease consisting of the antibody or fragment thereof as an active ingredient.

In addition, the present invention provides a composition for diagnosing of an immune cell migration-related disease consisting essentially of the antibody or fragment thereof as an active ingredient.

To achieve another object of the present invention, the present invention provides use of the antibody or fragment thereof for preparing an agent for preventing or inhibiting cancer and cancer metastasis.

To achieve another object of the present invention, the present invention provides a method for preventing or inhibiting cancer and cancer metastasis, administering an effective amount of a composition comprising the antibody or fragment thereof to a subject in need thereof.

To achieve another object of the present invention, present invention provides a use of the antibody or fragment thereof for preparing an agent for cancer or cancer metastasis diagnosis.

To achieve another object of the present invention, the present invention provides that a method for diagnosing cancer or cancer metastasis, the method comprising: a) obtaining a biological sample from an individual (subject) suspected of cancer metastasis;

b) administering a composition comprising the antibody or a fragment thereof to the sample or subject;

c) detecting the expression level of the KRS protein in the sample or subject of step b); and d) comparing the expression level of the KRS protein with a normal control group, and diagnosing that cancer and cancer metastasis have occurred when the expression level of KRS is increased.

To achieve another object of the present invention, the present invention provides use of the antibody or fragment thereof for preparing an agent for treatment of an immune cell migration-related disease.

To achieve another object of the present invention, the present invention provides a method for treating an immune cell migration-related disease, administering an effective amount of a composition comprising the antibody or fragment thereof to a subject in need thereof.

To achieve another object of the present invention, the present invention provides use of the antibody or fragment thereof of claim 1 for preparing an agent for diagnosis of an immune cell migration-related disease.

To achieve another object of the present invention, the present invention provides that a method for diagnosing an immune cell migration-related disease, the method comprising:

a) obtaining a biological sample from a subject suspected of an immune cell migration-related disease;

b) administering a composition comprising the antibody or a fragment to the sample or subject;

c) detecting the expression level of the KRS protein in the sample or subject of step b); and d) comparing the expression level of the KRS protein with a normal control group, and diagnosing as an immune cell migration-related disease when the expression level of KRS is increased.

Hereinafter, the present invention will be described in detail.

As used herein, the term "extracellularly exposed lysyl-tRNA synthetase (KRS)N-terminal region" refers to a particular sequence exposed to the extracellular space or on the surface of the cell membrane when KRS produced in cells is translocated to the cell membrane (or plasma membrane), and may normally refer to a partial or full-length sequence of a 1- to 72-amino acid region in the KRS N-terminus. In addition, there is sequence similarity across species in the KRS N-terminal region, and especially, the KRS N-terminal region may contain the amino acid sequence defined by SEQ ID NO: 177.

As used herein, the term "KRS" refers to the full-length polypeptide known as lysyl-tRNA synthetase or any KRS fragment sequence comprising the N-terminal region. As described above, the antibodies or fragments thereof according to the present invention specifically detect the extracellularly exposed KRS N-terminal region, and thus also can detect the foregoing KRS full-length polypeptide or any KRS fragment sequence containing the N-terminal region. The specific sequence of KRS is not particularly limited as long as the sequence contains the polypeptide defined by SEQ ID NO: 117 and is known as lysyl-tRNA synthetase in the art. For instance, KRS of the present invention includes: a sequence derived from a human (*Homo sapiens*) and known as NCBI (Genbank) Accession No. NP_005539.1 or the like; a sequence derived from a mouse (*Mus musculus*) and known as NCBI (Genbank) Accession No. NP_444322.1 or the like; and a sequence derived from a rat (*Rattus norvegicus*) and known as NCBI (Genbank) Accession No. XP_006255692.1 or the like, and besides, reference may be made to the following sequence information, but is not limited thereto: XP_005004655.1 (guinea-pig: *Cavia porcellus*), XP_021503253.1 (gerbil, Meriones unguiculatus), XP_002711778.1 (rabbit, Oryctolagus *cuniculus*), XP_536777.2 (dog, *Canis lupus familiaris*), XP_003126904.2 (swine, *Sus scrofa*), XP_011755768.1 (monkey, *Macaca* nemestrina), XP_008984479.1 (marmoset, Callithrix jacchus), XP_019834275.1 (cow, Bos *indicus*), XP_511115.2 (chimpanzee, Pan troglodytes). Most preferably, it may be known as NCBI (Genbank) Genbank Accession No. NP_005539.1.

In the present invention, the "antibody" is also called immunoglobulin (Ig) and is a generic term for proteins that are involved in biological immunity by selectively acting on antigens. A whole antibody found in nature usually consists of two pairs of light chain (LC) and heavy chain (HC), each of which is a polypeptide composed of several domains, or has two pairs of HC/LC as a basic unit. There are five types of heavy chains constituting mammalian antibodies, which are denoted by the Greek letters: $\alpha$, $\delta$, $\varepsilon$, $\epsilon$, and $\mu$, and different types of heavy chains constitute different types of antibodies: IgA, IgD, IgE, IgG and IgM, respectively. There are two types of light chains constituting mammalian antibodies, which are denoted by $\lambda$ and $\kappa$.

The heavy and light chains of antibodies are structurally divided into a variable region and a constant region according to the variability of amino acid sequence. The constant region of the heavy chain is composed of three or four heavy chain constant regions, such as CH1, CH2, and CH3 (IgA, IgD, and IgG antibodies) and CH4 (IgE and IgM antibodies), according to the type of antibody, and the light chain has one constant region CL. The variable regions of the heavy and light chains are each composed of one domain of a heavy chain variable region (VH) or a light chain variable region (VL). The light chain and the heavy chain are linked to each other by one covalent disulfide linkage while variable regions and constant regions thereof are arranged in parallel, and two heavy chain molecules, which are linked with the light chains, are linked to each other by two covalent disulfide linkages, thereby forming a whole antibody. The whole antibody specifically binds to an antigen through the variable regions of the heavy and light chains. The whole antibody is composed of two pairs of heavy and light chains (HC-LC), and thus one whole antibody molecule has divalent mono-specificity in which one whole antibody molecule binds to two same antigens through two variable regions.

The variable regions of the antibody, which comprise antigen-binding sites, are each divided into framework regions (FRs) with low sequence variability and complementary determining regions (CDRs), which are hypervariable regions with high sequence variability. In VH and VL, three CDRs and four FRs are arranged in the order of FR1-CDR1-FR2-CDR2-FR3-CDR3-FR4 in a direction from the N-terminal to the C-terminal. CDRs, which have the highest sequence variability in the variable regions of the antibody, are sites that directly bind to an antigen, and are very important in antigen specificity of the antibody.

The present invention provides an antibody or fragment thereof that specifically binds to an extracellularly exposed lysyl-tRNA synthetase (KRS, Lysyl-tRNA synthetase)N-terminal region, the antibody or fragment thereof comprises:
(a) a heavy chain variable region (VH) comprising
(i) heavy chain complementarity determining region 1 (CDR1) containing the amino acid sequence SYDMS (SEQ ID NO: 1);

(ii) heavy chain complementarity determining region 2 (CDR2) containing the amino acid sequence $X_1IX_2X_3X_4X_5GX_6X_7YYADSVKG$, and wherein $X_1$ is A or V, $X_2$ is S, D or G, $X_3$ is Y, P, S or A and $X_4$ is D, Q, L or Y, $X_5$ is N, M, S, or G, $X_6$ is N, R or P, $X_7$ is T, V, I or S; and
(iii) heavy chain complementarity determining region 3 (CDR3) containing an amino acid sequence $X_8$ALDFDY (SEQ ID NO:253), and wherein $X_8$ is M or L, and
(b) a light chain variable region (VL) comprising
(i) light chain complementarity determining region 1 (CDR1) containing the amino acid sequence TGSSSNIGSNYVT (SEQ ID NO: 7);
(ii) light chain complementarity determining region 2 (CDR2) comprising amino acid sequence $X_9NX_{10}X_{11}RPS$ (SEQ ID NO: 254), wherein $X_9$ is D, S or R, $X_{10}$ is S or N, and $X_{11}$ is N or Q; and
(iii) light chain complementarity determining region 3 (CDR3) containing an amino acid sequence $X_{12}SFSDELGAYV$ (SEQ ID NO: 255), and wherein $X_{12}$ is A or S.

Specifically, wherein (a) the heavy chain variable region (VH) comprises a heavy chain complementarity determining region 1 (CDR1) containing the amino acid sequence defined by SEQ ID NO: 1; and heavy chain complementarity determining region 2 (CDR2) containing at least one amino acid sequence selected from the group consisting of SEQ ID NO: 3, SEQ ID NO: 17, SEQ ID NO: 19, SEQ ID NO: 21, SEQ ID NO: 23, and SEQ ID NO: 118, and heavy chain complementarity determining region 3 (CDR3) containing at least one amino acid sequence selected from the group consisting of SEQ ID NO: 5 and SEQ ID NO: 25, and wherein (b) the light chain variable region (VL) comprises a light chain complementarity determining region 1 (CDR1) containing the amino acid sequence defined by SEQ ID NO: 7; a light chain complementarity determining regions 2 (CDR2) containing at least one amino acid sequence selected from the group consisting of SEQ ID NO: 9, SEQ ID NO: 27 and SEQ ID NO: 29; a light chain complementarity determining region 3 (CDR3) containing at least one amino acid sequence selected from the group consisting of SEQ ID NO: 13 and SEQ ID NO: 15.

Antibodies composed of the CDR sequences have excellent ability to specifically bind to the KRS N-terminal region exposed to the outer cell membrane. This is well described in the specification examples of the present invention.

In an example of the present invention, in order to produce an antibody that specifically binds to the KRS N-terminal region exposed to the outer cell membrane and has high affinity, after improving the heavy chain variable region and the light chain variable region of the existing N3 antibody (application number: 10-2018-0035446), the improved library was selected through yeast expression.

Through primary, secondary, and tertiary FACS screening, N3-1, N3-3, and N3-4 scFvs having high affinity and specificity in the KRS N-terminal region were selected, and a new N3-5 scFv in which its VH and VL were combined with each other was selected.

Then, in order to select an improved library that specifically binds to the GST-bound KRS N-terminus and has high affinity, a library having an improved heavy chain variable region of N3-3 scFv was selected. N3-6, N3-7, N3-8, and N3-9 scFvs having high affinity and specificity in the KRS N-terminal region were selected through primary, secondary, tertiary, and fourth FACS screening.

Among them, in order to improve the productivity and stability of the N3-8 IgG antibody having the highest affinity, 7 kinds of antibodies (N3-8-1, N3-8-2, N3-8-3, N3-8-4, N3-8-5, N3-8-6, N3-8-7) were obtained by introducing mutations in the heavy and light chain regions of N3-8.

As a result, antibodies of N3-1 IgG, N3-3 IgG, N3-4 IgG, N3-5 IgG, N3-6 IgG, N3-7 IgG, N3-8 IgG, N3-9 IgG, N3-8-1 IgG, N3-8-2 IgG, N3-8-3 IgG, N3-8-4 IgG, N3-8-5 IgG, N3-8-6 IgG, and N3-8-7 IgG were prepared and it was confirmed that the antibody also showed high affinity to the KRS N-terminus.

The 'antibody or fragment thereof that specifically binds to the KRS N-terminal region exposed to the extracellular membrane' according to the present invention is not limited thereto, but preferably, as an antibody comprising the CDR composition of the heavy chain variable region and the light chain variable region as follows, the following i, ii, iii, iv, v, vi, vii, viii, ix, x, xi, xii and xiii respectively represent the CDR combinations of the N3-1, N3-3, N3-4, N3-5, N3-6, N3-7, N3-8, N3-9, N3-8-1, N3-8-2, N3-8-3, N3-8-4, N3-8-5, N3-8-6 and N3-8-7 antibodies of examples:

The antibody or fragment thereof of claim 1, wherein the antibody or fragment thereof comprises i) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 3, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 13;

ii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 3, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

iii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 118, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 13;

iv) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 118, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

v) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 17, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

vi) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 19, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

vii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

viii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 23, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

ix) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 27, and light chain complementary determining region 3 (CDR3) containing the amino acid sequence defined by SEQ ID NO: 15;

x) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3 (CDR3) containing the amino acid sequence defined by SEQ ID NO: 5, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 29, and light chain complementary determining region 3 (CDR3) containing the amino acid sequence defined by SEQ ID NO: 15;

xi) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3

(CDR3) containing the amino acid sequence defined by SEQ ID NO: 25, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 9, and light chain complementary determining region 3 (CDR3) containing the amino acid sequence defined by SEQ ID NO: 15;

xii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3 (CDR3) containing the amino acid sequence defined by SEQ ID NO: 25, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 27, and light chain complementary determining region 3 (CDR3) containing the amino acid sequence defined by SEQ ID NO: 15; or xiii) an antibody comprising an antibody heavy variable region (VH) comprising heavy chain complementary determining region 1 (CDR1) containing the amino acid sequence defined by SEQ ID NO: 1, heavy chain complementary determining region 2 (CDR2) containing the amino acid sequence defined by SEQ ID NO: 21, heavy chain complementary determining region 3 (CDR3) containing the amino acid sequence defined by SEQ ID NO: 25, and an antibody light chain variable region (VL) comprising light chain complementary determining region 1 (CDR1) containing the amino acid sequence defined by SEQ ID NO: 7, light chain complementary determining region 2 (CDR2) containing the amino acid sequence defined by SEQ ID NO: 29, and light chain complementary determining region 3 (CDR3) containing the amino acid sequence defined by SEQ ID NO: 15.

Most preferably, the antibody or fragment thereof according to the present invention is characterized by comprising a heavy chain variable region (VH) and a light chain variable region (VL) as follows:

In the antibody or fragment thereof, the heavy chain variable region includes one or more amino acid sequences selected from the group consisting of SEQ ID NO: 31, SEQ ID NO: 35, SEQ ID NO: 37, SEQ ID NO: 39, SEQ ID NO: 41, SEQ ID NO: 43, SEQ ID NO: 45, and SEQ ID NO: 47, and the light chain variable region includes one or more amino acid sequences selected from the group consisting of SEQ ID NO: 49, SEQ ID NO: 51, SEQ ID NO: 53, and SEQ ID NO: 55.

Preferably, it is an antibody containing a heavy chain variable region comprising an amino acid sequence defined by SEQ ID NO: 31 and a light chain variable region comprising an amino acid sequence defined by SEQ ID NO: 49; A heavy chain variable region comprising an amino acid sequence defined by SEQ ID NO: 31 and a light chain variable region comprising an amino acid sequence defined by SEQ ID NO: 51; A heavy chain variable region comprising an amino acid sequence defined by SEQ ID NO: 35 and a light chain variable region comprising an amino acid sequence defined by SEQ ID NO: 49; A heavy chain variable region comprising an amino acid sequence defined by SEQ ID NO: 35 and a light chain variable region comprising an amino acid sequence defined by SEQ ID NO: 51; A heavy chain variable region comprising an amino acid sequence defined by SEQ ID NO: 37 and a light chain variable region comprising an amino acid sequence defined by SEQ ID NO: 51; A heavy chain variable region comprising an amino acid sequence defined by SEQ ID NO: 39 and a light chain variable region comprising an amino acid sequence defined by SEQ ID NO: 51; A heavy chain variable region comprising an amino acid sequence defined by SEQ ID NO: 41 and a light chain variable region comprising an amino acid sequence defined by SEQ ID NO: 51; A heavy chain variable region comprising an amino acid sequence defined by SEQ ID NO: 43 and a light chain variable region comprising an amino acid sequence represented by SEQ ID NO: 51; A heavy chain variable region comprising an amino acid sequence represented by SEQ ID NO: 45 and a light chain variable region comprising an amino acid sequence represented by SEQ ID NO: 51; A heavy chain variable region comprising an amino acid sequence represented by SEQ ID NO: 45 and a light chain variable region comprising an amino acid sequence represented by SEQ ID NO: 53; A heavy chain variable region comprising an amino acid sequence defined by SEQ ID NO: 45 and a light chain variable region comprising an amino acid sequence defined by SEQ ID NO: 55; A heavy chain variable region comprising an amino acid sequence defined by SEQ ID NO: 47 and a light chain variable region comprising an amino acid sequence defined by SEQ ID NO: 51; A heavy chain variable region comprising an amino acid sequence defined by SEQ ID NO: 47 and a light chain variable region comprising an amino acid sequence defined by SEQ ID NO: 53; A heavy chain variable region comprising an amino acid sequence defined by SEQ ID NO: 47 and a light chain variable region comprising an amino acid sequence defined by SEQ ID NO: 55.

The IgG type antibody comprising the heavy chain variable region (VH) and the light chain variable region (VL) may be specifically an antibody characterized by consisting of a heavy chain comprising at least one amino acid sequence selected from the group consisting of SEQ ID NO: 89, SEQ ID NO: 93, SEQ ID NO: 95, SEQ ID NO: 97, SEQ ID NO: 99, SEQ ID NO: 101, SEQ ID NO: 103 and SEQ ID NO: 105, and a light chain comprising at least one amino acid sequences selected from the group consisting of SEQ ID NO: 107, SEQ ID NO: 109, SEQ ID NO: 111, SEQ ID NO: 113, and SEQ ID NO: 115.

Most preferably, it is an antibody containing a heavy chain comprising an amino acid sequence defined by SEQ ID NO: 89 and a light chain comprising an amino acid sequence defined by SEQ ID NO: 107; A heavy chain comprising an amino acid sequence defined by SEQ ID NO: 89 and a light chain comprising an amino acid sequence defined by SEQ ID NO: 109; A heavy chain comprising an amino acid sequence defined by SEQ ID NO: 93 and a light chain comprising an amino acid sequence defined by SEQ ID NO: 107; A heavy chain comprising an amino acid sequence defined by SEQ ID NO: 93 and a light chain comprising an amino acid sequence defined by SEQ ID NO: 109; A heavy chain comprising an amino acid sequence defined by SEQ ID NO: 95 and a light chain comprising an amino acid sequence defined by SEQ ID NO: 109; A heavy chain comprising an amino acid sequence defined by SEQ ID NO: 97 and a light chain comprising an amino acid sequence defined by SEQ ID NO: 109; A heavy chain comprising an amino acid sequence defined by SEQ ID NO: 99 and a light chain comprising an amino acid sequence defined by SEQ ID NO: 109; A heavy chain comprising an amino acid sequence defined by SEQ ID NO: 101 and a light chain comprising an amino acid sequence defined by SEQ ID NO: 109; A heavy chain comprising the amino acid sequence defined by SEQ ID NO: 103 and a light chain comprising the amino acid sequence defined by SEQ ID NO: 111; A heavy chain comprising an amino acid sequence defined by SEQ ID NO: 103 and a light chain comprising an amino acid sequence defined by SEQ ID NO: 113; A heavy chain comprising an amino acid sequence defined by SEQ ID NO: 103 and a light chain comprising an amino acid sequence defined by SEQ ID NO: 115; A heavy chain comprising an amino acid sequence defined by SEQ ID NO: 105 and a light chain comprising an amino acid sequence defined by SEQ ID NO: 111; A heavy chain comprising an amino acid sequence defined by SEQ ID NO: 105 and a light chain comprising an amino acid sequence defined by SEQ ID NO: 113; A heavy chain comprising an amino acid sequence defined by SEQ ID NO: 105 and a light chain comprising an amino acid sequence defined by SEQ ID NO: 115; It is an antibody comprising a heavy chain comprising the amino acid sequence defined by SEQ ID NO: 99 and a light chain comprising the amino acid sequence defined by SEQ ID NO: 111.

The "antibody specifically binding to the extracellularly exposed KRS N-terminal region" according to the present invention is not limited to the type thereof as long as the antibody has the above CDR combinations or VH and VL combinations. As a specific example, the antibody may be selected from the group consisting of IgG, IgA, IgM, IgE, and IgD antibodies, and may be preferably an IgG antibody.

The antibodies of the present invention may be monoclonal antibodies or polyclonal antibodies as long as the antibodies have the above CDR combinations or VH and VL combinations that specifically bind to the KRS N-terminal region, but are preferably monoclonal antibodies, which are a group of antibodies each having substantially identical amino acid sequences in heavy and light chains.

The antibody of the present invention may be derived from any animals including mammals including humans, and birds, and may be preferably derived from humans. However, the antibody of the present invention may be a chimeric antibody including a portion of the antibody derived from humans and a portion of the antibody derived from a different species of animal. That is, the present invention includes all of chimeric antibodies, humanized antibodies, and human antibodies, and may be preferably human antibodies.

In addition, the fragment of the antibody of the present invention refers to an antibody fragment that retains antigen-specific binding ability of a whole antibody. Preferably, the fragment retains at least 20%, 50%, 70%, 80%, 90%, 95%, or 100% of the KRS N-terminal binding affinity of the mother antibody. Specifically, the fragment may be in the form of Fab, F(ab)2, Fab', F(ab')2, Fv, diabody, scFv, or the like.

Fab (fragment, antigen-binding) is an antigen-binding fragment of an antibody, and is composed of a heavy chain and a light chain each consisting of one variable domain and one constant domain. F(ab')2 is a fragment produced by pepsin hydrolysis of an antibody, and F(ab')2 has a form in which two Fab molecules are linked via disulfide bonds at the heavy-chain hinge region. F(ab') is a monomeric antibody fragment in which a heavy-chain hinge is added to a Fab separated from F(ab')2 fragment by the reduction of disulfide bonds thereof. Fv (variable fragment) is an antibody fragment composed of only respective variable regions of the heavy and light chains. scFv (single chain variable fragment) is a recombinant antibody fragment in which a heavy chain variable region (VH) and a light chain variable region (VL) are linked to each other via a flexible peptide linker. The diabody refers to a fragment in which VH and VL of scFv are linked by a very short linker and thus cannot be bound to each other, and bind to VL and VH of another scFv in the same form, respectively, to form a dimer.

For the purposes of the present invention, the fragment of the antibody is not limited to the structure or conformation thereof as long as the fragment of the antibody retains binding specificity to the KRS N-terminal region, but may be preferably scFv. The scFv according to the present invention has a CDR conformation or VH and VL conformation specific to the KRS N-terminal region, and the sequence thereof is not particularly limited as long as the C-terminal of VH and the N-terminal of VL are linked through a linker. The linker is not particularly limited to the type thereof as long as it is known as a linker applied to scFv in the art, but may be a peptide containing the amino acid sequence defined by SEQ ID NO: 57. Specifically, the scFv of the present invention may contain the amino acid sequence selected from the group consisting of SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85 and SEQ ID NO: 87.

The antibody or fragment thereof of the present invention may comprise a conservative amino acid substitution (also called a conservative variant of the antibody) that does not substantially change biological activity thereof.

In addition, the foregoing antibody or fragment thereof of the present invention may be conjugated to an enzyme, a fluorescent material, a radioactive material, and a protein, but is not limited thereto. Also, methods of conjugating the above materials to the antibody have been well known in the art.

In addition, the present invention provides a polynucleotide encoding the antibody or fragment thereof.

In the present specification, the polynucleotide may be described as an oligonucleotide or a nucleic acid, and includes: DNA or RNA analogues (e.g., peptide nucleic acids and non-naturally occurring nucleotide analogues) generated using DNA molecules (e.g., cDNA or genomic DNA), RNA molecules (e.g., mRNA), or nucleotide analogues; and hybrids thereof. The polynucleotide may be single-stranded or double-stranded.

The polynucleotide refers to a nucleotide sequence encoding an antibody composed of heavy and light chains each having a CDR conformation or VH and VL conformation specific to the KRS N-terminal region. The polynucleotide of the present invention is not particularly limited to the sequence thereof as long as the sequence encodes the antibody or fragment thereof of the present invention. The polynucleotides encoding the foregoing CDR sequences in the above-described antibodies according to the present invention are not particularly limited to the sequences thereof, but may preferably contain the nucleotide sequence defined by SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30 or SEQ ID NO: 119.

In addition, the polynucleotides encoding the foregoing VH and VL in the antibody according to the present invention are not particularly limited to the sequences thereof, but may preferably contain the nucleotide sequence defined by SEQ ID NO: 32 (VH), SEQ ID NO: 34 (VL), SEQ ID NO: 36 (VH), SEQ ID NO: 38 (VH), SEQ ID NO: 40 (VH), SEQ ID NO: 42 (VH), SEQ ID NO: 44 (VH), SEQ ID NO: 46 (VH), SEQ ID NO: 48 (VH), SEQ ID NO: 50 (VL), SEQ ID NO: 52 (VL), SEQ ID NO: 54 (VL) or SEQ ID NO: 56 (VL).

In addition, the polynucleotide encoding the fragment of the antibody may preferably contain the nucleotide sequence of any one selected from the group consisting of SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86 and SEQ ID NO: 88, which encode scFv fragments according to the present invention.

The polynucleotides encoding the antibody or fragment thereof of the present invention may be obtained by a method known in the art. For example, on the basis of DNA sequences encoding a part or the entirety of the heavy and light chains of the antibody or corresponding amino acid sequences, the polynucleotides may be synthesized by the oligonucleotide synthesis methods that are known in the art, e.g., a polymerase chain reaction (PCR) method.

The present invention provides a recombinant expression vector comprising the polynucleotide encoding the antibody or fragment thereof according to the present invention.

As used herein, the "recombinant", used interchangeably with "genetic manipulation", and refers to the construction of a gene in the form that does not exist in nature, by using molecular cloning experiment techniques, such as gene transformation, cleavage, or linkage.

As used herein, the term "expression" refers to the production of proteins or nucleic acids in cells.

As used herein, the term "recombinant expression vector" is a vector that can express a target protein or nucleic acid (RNA) in a suitable host cell, and refers to a gene construct comprising essential control elements that are operably linked to be capable of expressing a polynucleotide (gene) insert. The term "operably linked" refers to the functional linkage of a nucleic acid expression control sequence and a nucleic acid sequence encoding a target protein or RNA so as to perform general functions, which means the linkage therebetween so as to allow a gene to be expressed by the expression control sequence. The expression control sequence refers to a DNA sequence that controls the expression of an operably linked polynucleotide sequence in a particular host cell. Such an expression control sequence includes a promoter for transcription, any operator sequence for controlling transcription, a sequence for encoding a proper mRNA ribosomal binding site, a sequence for controlling the termination of transcription and translation, an initiation codon, a termination codon, a polyadenylation A signal, an enhancer, and the like.

The recombinant expression vector of the present invention is not particularly limited to the type thereof as long as the vector is ordinarily used in a field of cloning, and examples of the recombinant expression vector include a plasmid vector, a cosmid vector, a bacteriophage vector, and a viral vector, but are not limited thereto. Examples of the plasmid may include *Escherichia coli*-derived plasmids (pBR322, pBR325, pUC118, pUC119, and pET-22b (+)), *Bacillus subtilis*-derived plasmids (pUB110 and pTP5), and yeast-derived plasmids (YEp13, YEp24, and YCp50), and examples of the virus may include: animal viruses, such as retrovirus, adenovirus, or vaccinia virus; and insect viruses, such as baculovirus.

The recombinant expression vector according to the present invention means a gene construct that is operably linked so as to be capable of expressing, in a suitable host cell, a polynucleotide encoding the antibody or fragment thereof composed of heavy and light chains having the foregoing CDR or VH and VL conformations capable of specifically binding the KRS N-terminal region.

The polynucleotides encoding heavy and light chains of the antibody according to the present invention may be contained in separate recombinant expression vectors, respectively, or may be contained in one recombinant expression vector.

The present invention provides cells transformed with the above-described recombinant expression vector.

The cells of the present invention are not particularly limited to the type thereof as long as the cells can be used to express a polynucleotide encoding an antibody or a fragment thereof contained in the recombinant expression vector of the present invention. The cells (host cells) transformed with the recombinant expression vector according to the present invention may be prokaryotic cells (e.g., *E. coli*), eukaryotic cells (e.g., yeast or other fungi), plant cells (e.g., tobacco or tomato plant cells), animal cells (e.g., human cells, monkey cells, hamster cells, rat cells, mouse cells, or insect cells), or hybridomas derived therefrom. Preferably, the cells may be derived from mammals including humans.

Exemplary prokaryotes suitable for the present purpose include Gram-negative or Gram-positive organisms, for example, Enterobacteriaceae such as *Escherichia*, e.g., *E. coli*, *Enterobacter*, *Erwinia*, | *Klebsiella*, *Proteus*, *Salmonella*, e.g., *Salmonella typhimurium*, *Serratia*, e.g., *Serratia marcescens*, and *Shigella*, as well as Bacilli, e.g., *B. subtilis* and *B. licheniformis*, *Pseudomonas*, e.g., *P. aeruginosa*, and *Streptomyces*. The cells of the present invention are not particularly limited as long as the cells can express the vector of the present invention, but may be preferably *E. coli*.

*Saccharomyces cerevisiae* is most frequently used as a eukaryote for the cells of the present invention. However, a number of other genera, species, and strains can be used, but are not limited to, for example, *Schizosaccharomyces pombe*; *Kluyveromyces* hosts, such as, *K lactis*, *K. fragilis* (ATCC 12,424), K. *bulgaricus* (ATCC 16,045), K. *wickeramii* (ATCC 24,178), *K. waltii* (ATCC 56,500), K. *drosophilarum* (ATCC 36,906), *K. thermotolerans*, and *K. marxianus*; *Yarrowia* (EP 402,226); *Pichia pastoris* (EP 183,070); *Candida*; *Trichoderma* reesia (EP 244,234); *Neurospora crassa*; *Schwanniomyces*, such as *Schwanniomyces occidentalis*; and filamentous fungi, for example, *Neurospora*, *Penicillium*, *Tolypocladium*, and *Aspergillus* hosts, such as *A. nidulans* and *A. niger*.

The term "transformation" refers to a modification of the genotype of a host cell due to the introduction of exotic polynucleotides, and refers to an introduction of an exotic polynucleotide into a host cell regardless of a method used for the transformation. The exotic polynucleotide introduced into the host cell is incorporated into and maintained in the genome of the host cell, or is maintained without the incorporation thereinto, and the present invention includes both.

The recombinant expression vector capable of expressing the antibody or fragment thereof specifically binding to the KRS N-terminal region according to the present invention can be introduced into cells for producing the antibody or fragment thereof, by a method known in the art, for example, but is not limited to, transient transfection, microinjection, transduction, cell fusion, calcium phosphate precipitation, liposome-mediated transfection, DEAE dextran-mediated transfection, polybrene-mediated transfection, electroporation, gene gun, and known methods for introducing nucleic acids into cells, and then can transform the cells.

The present invention provides a method for preparing an antibody or fragment thereof specifically binding to an extracellularly exposed lysyl-tRNA synthetase (KRS)N-terminal region, the method comprising:

(a) transforming host cells with the recombinant expression vector;

(b) incubating the transformed host cells to produce an antibody or fragment thereof; and (c) collecting the antibody or fragment thereof produced in the host cells.

In step (a), in order to produce the antibody or fragment thereof according to the present invention, host cells are transformed with the recombinant expression vector, in which the polynucleotide encoding the antibody or fragment thereof is operably linked.

A person skilled in the art can perform the present step by selecting a suitable transformation method according to the selected host cells and recombinant expression vector as described above. The recombinant expression vectors comprising nucleotide sequences of heavy and light chains may be co-transformed in the same host cell to allow the heavy and light chains to be expressed in one cell, or the recombinant expression vectors comprising nucleotide sequences of heavy and light chains may be transformed in separate host cells to allow the heavy and light chains to be separately expressed.

In step (b), the transformed host cells are incubated to produce polypeptides of heavy and light chains of the antibody or fragment of the antibody according to the present invention from the recombinant expression vector introduced into the host cells.

The medium composition, incubation conditions, and incubation time for incubating the host cells may be appropriately selected according to a method ordinarily used in the art. The antibody molecules produced in the host cell may be accumulated in the cellular cytoplasm, may be secreted outside the cell or in the culture medium by a suitable signal sequence, or may be targeted using a periplasm or the like. It is also preferable that the antibody according to the present invention has a functional conformation through protein refolding using a method known in the art so as to maintain binding specificity to the KRS N-terminal. As for the production of IgG type antibody, heavy and light chains may be expressed in separate cells and then contacted with each other in a separate step to constitute the whole antibody, or heavy and light chains may be expressed in the same cell to form the whole antibody inside the cell.

In step (c), the antibody or fragment thereof produced in the host cells is obtained.

A person skilled in the art can properly select and control the collection method considering characteristics of polypeptides of the antibody or fragment thereof produced in the host cells, characteristics of the host cells, the mode of expression, or the targeting or not of the polypeptide. For example, the antibody or fragment thereof secreted into the culture medium can be collected by obtaining the culture medium, in which the host cells are cultured, removing impurities through centrifugation, and the like. In order to, as necessary, excrete the antibody present in specific organelles or cytoplasm in the cells to the outside of the cells and collect the antibody, the cells may be lysed within an extent that does not affect the functional structure of the antibody or the fragment thereof. The obtained antibody may be further subjected to a process of further removing impurities and carrying out concentration, through chromatography, filtration using a filter, dialysis, or the like.

The polypeptide in the manufacturing (production) method of the present invention may be the antibody or fragment thereof itself of the present invention, and a polypeptide to which another amino acid sequence other than the antibody or fragment thereof of the present invention is further bound. In this case, the amino acid sequence may be removed from the antibody or fragment thereof of the present invention by using a method well known to a person skilled in the art.

The antibody or fragment thereof of the present invention specifically binds to the KRS N-terminal region, and thus is useful in the diagnostic analysis for detecting and quantifying KRS proteins in, for example, particular cells, tissues, or serum. Especially, the extracellularly exposed KRS N-terminal region can be specifically detected without cell lysis.

The detection method of the present invention may comprise a step of preparing a sample, which is to be measured for the presence or absence of KRS (or extracellularly exposed KRS N-terminal peptide) and the concentration thereof by using the antibody or fragment thereof according to the present invention (step (1)), before contacting the antibody or fragment thereof according to the present invention with the sample.

A person skilled in the art may suitably select a known protein detection method using an antibody and prepare a sample suitable for the selected method. In addition, the sample may be cells or tissues obtained by biopsy, blood, whole blood, serum, plasma, saliva, cerebrospinal fluid, or the like, which is collected from a subject to be examined for the presence or absence of cancer (especially breast cancer or lung cancer) or cancer metastasis. Examples of the protein detection method using the antibody include, but are not limited to, western blotting, immune blotting, dot blotting, immunohistochemistry, enzyme-linked immunosorbent assay (ELISA), radioimmunoassay, competitive binding assay, immunoprecipitation, and the like. For example, for western blotting, a preparation may be made by adding a buffer suitable for electrophoresis to a sample or cell lysate, followed by boiling, and for immunohistochemistry, a treatment may be performed by immobilizing and blocking cells or tissue slices, followed by blocking.

Next, a step of contacting the antibody or fragment thereof according to the present invention with the sample prepared in the above-described step is performed (step (2)).

The antibody according to the present invention is an antibody or fragment thereof that has the above-described CDR or VH and VL conformations and specifically binds to the KRS N-terminal region, and specific types and sequence organization thereof are as described above.

The antibody or fragment thereof may be labeled with a general detectable moiety, for "detection" thereof. For instance, the antibody or fragment thereof may be labeled with a radioisotope or fluorescent label by using the known in the art. In addition, various enzyme-substrate labels are usable, and examples of the enzymatic label include: luciferase, such as *drosophila* luciferase and bacterial luciferase (U.S. Pat. No. 4,737,456), luciferin, 2,3-dihydrophthalazine dionise, malate dehydrogenase, urase, peroxidase such as horseradish peroxidase (HRPO), alkaline phosphatase, β-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase, and the like. Techniques for conjugating enzymes to antibodies are known in the art. The labels may be directly or indirectly conjugated to antibodies using various known techniques. For instance, the antibody may be conjugated to biotin, and any labels pertaining to three classes of widespread categories cited above may be conjugated to avidin or vice versa. Biotin may selectively bind to avidin, and therefore, this label may be conjugated to an antibody in such an indirect manner. Alternatively, in order to attain the indirect conjugation of a label to an antibody, the antibody may be conjugated to a small hapten (e.g., dioxin), and one of different types of labels recited above may be conjugated to an anti-hapten antibody (e.g., anti-dioxin antibody). Therefore, the indirect conjugation of a label to an antibody can be attained.

As used herein, the "contacting" is used in a general sense thereof, and refers to the mixing, binding, or touching of two or more substances. The contacting may be performed in vitro or in another container, or may be performed in situ, in vivo, in the subject, in the tissue, or in the cell.

Next, a step of detecting the antibody or fragment thereof according to the present invention from the sample after the execution of step (2) is performed (step (3)).

The "detection" is performed on a complex of the antibody or fragment thereof according to the present invention and an antigen, the complex being formed in the sample, and refers to the detection of the presence or absence of the KRS N-terminal peptide (or a protein including the peptide, for example, KRS) or the measurement (including qualitative measurement, quantitative measurement, or both) of the level of the peptide. Therefore, the detection method of the present invention may further comprise a step of removing extra antibodies or fragments thereof, which did not form the complex together with the KRS N-terminal region, after the execution of step (2) before step (3) to be described later.

When the antibody or fragment thereof used in step (2) described above contains a detectable moiety, such as fluorescence, radioactive isotope, or enzyme, which directly labels the antibody or fragment thereof, the detection may be carried out by a detection method for the corresponding moiety, known in the art. For instance, radioactivity may be measured by, for example, scintillation counting, and fluorescence may be quantified using a fluorometer.

When the antibody or fragment thereof, per se, used in step (2) described above does not contain the foregoing detectable moiety, the indirect detection using a secondary antibody labeled with fluorescence, radioactivity, enzyme, or the like may be carried out. The secondary antibody binds to the antibody or fragment thereof (primary antibody) according to the present invention.

The present invention provides a pharmaceutical composition for preventing or inhibiting cancer metastasis and a composition for diagnosing cancer comprising the antibody or fragment thereof of the present invention as an active ingredient.

The cancer is not particularly limited to the type thereof as long as the cancer is known as a malignant tumor in the art, and example thereof may be selected from the group consisting of breast cancer, large intestine cancer, lung cancer, small cell lung cancer, gastric cancer, liver cancer, blood cancer, bone cancer, pancreatic cancer, skin cancer, head or neck cancer, cutaneous or intraocular melanoma, uterine cancer, ovarian cancer, rectal cancer, anal cancer, colon cancer, fallopian tube carcinoma, endometrial carcinoma, cervical cancer, vaginal cancer, vulvar carcinoma, Hodgkin's disease, esophageal cancer, small intestine cancer, endocrine cancer, thyroid cancer, parathyroid carcinoma, adrenal cancer, soft tissue sarcoma, urethral cancer, penis cancer, prostate cancer, chronic or acute leukemia, lymphocyte lymphoma, bladder cancer, kidney or ureter cancer, renal cell carcinoma, renal pelvic carcinoma, CNS tumor, primary CNS lymphoma, spinal cord tumor, brain stem glioma, and pituitary adenoma. Preferably, the cancer may be breast cancer or pulmonary cancer.

The present invention may comprise the antibody or fragment thereof of the present invention alone or may further comprise at least one pharmaceutically acceptable carrier. As used herein, the term "pharmaceutically acceptable" refers to a non-toxic composition that is physiologically acceptable, does not inhibit action of an active ingredient when administered to humans, and does not normally cause severe side effects.

In the pharmaceutical composition according to the present invention, the antibody or fragment thereof may be administered in several oral and parental dosage forms during clinical administration. The antibody or fragment thereof, when formulated, may be prepared using a diluent or an excipient, such as a filler, an extender, a binder, a wetting agent, a disintegrant, or a surfactant, which is normally used. Solid formulations for oral administration include a tablet, a pill, a powder, granules, a capsule, a troche, and the like. These solid formulations may be prepared by mixing an aryl derivative of chemical formula 1 of the present invention or a pharmaceutically acceptable salt thereof with at least one excipient, for example, starch, calcium carbonate, sucrose or lactose, or gelatin. In addition, lubricants, such as magnesium stearate and talc, may be used besides to the simple excipients. Liquid formulations for oral administration include a suspension, a solution for internal use, an emulsion, a syrup, and the like. Besides simple diluents that are frequently used, such as water and liquid paraffin, several excipients, for example, a wetting agent, a sweetener, an aroma, a preservative, and the like may be contained in the liquid formulations.

Exemplary formulations for parenteral administration include a sterile aqueous solution, a non-aqueous solvent, a suspension solvent, an emulsion, a freeze-drying agent, and a suppository. The composition for treatment of the present invention may be prepared in the form of a freeze-dried cake or an aqueous solution in order to mix and store any physiologically acceptable carrier, excipient, or stabilizer and an antibody with preferable purity. The acceptable carrier, excipient, or stabilizer is non-toxic to a user at the used dose and concentration, and examples thereof include: buffers, for example, phosphoric acid, citric acid, and other organic acids; antioxidants including ascorbic acid; low-molecular weight (less than about 10 residues) polypeptides; proteins, for example, serum albumin, gelatin, or immunoglobulin; hydrophilic polymers, for example, polyvinyl pyrrolidone; amino acids, for example, glycine, glutamine, asparagine, arginine, or lysine; monosaccharides, disaccharides, and other carbohydrates including glucose, mannose, or dextrin; chelating agents, for example, EDT; sugar alcohols, for example, mannitol or sorbitol; salt-forming counter ions, for example, sodium; and (or) non-ionic surfactants, for example, Tween, pluronics, or polyethylene glycol (PEG).

The antibody of the present invention may be administered in a pharmaceutically effective amount to a subject fighting against cancer or an immune cell migration-related disease. As used herein, the term "pharmaceutically effective amount" refers to an amount showing a higher response compared with negative control, and preferably refers to an amount sufficient to treat cancer, an amount sufficient to prevent or inhibit cancer metastasis, and an amount sufficient to treat an immune cell migration-related disease. The total effective amount of the antibody or fragment thereof of the present invention may be administered to a patient as a single dose, or may be administered by a fractionated treatment protocol, in which multiple doses are administered for a long period of time. The dose of the antibody or fragment thereof of the present invention to the human body may be normally 0.01-100 mg/kg/week, preferably 0.1-20 mg/kg/week, and more preferably 5-10 mg/kg/week. However, as for the dose of the antibody or fragment thereof of the present invention, an effective dose thereof with respect to a patient is determined in consideration of various factors, for example, the route of administration of the pharmaceutical composition, the number of times of treatment, a patient's age, body weight, health condition, and sex, the severity of disease, the diet, and the excretion rate, and therefore, considering this fact, a person skilled in the art could determine a suitable effective amount of the antibody or fragment thereof of the present invention according to the particular use as a cancer metastasis preventor or inhibitor. The pharmaceutical composition according to the present invention is not particularly limited to the dosage form, route of administration, and administration method thereof as long as the composition shows effects of the present invention.

The route of administration of the composition of the present invention may be a known antibody administration method, for example, the injection or infusion by an intravenous, intraperitoneal, intracranial, subcutaneous, intramuscular, intraocular, intraarterial, cerebrospinal, or intralesional route, or the injection or infusion by the sustained release system described below. For example, the antibody of the present invention may be administered systemically or locally.

The pharmaceutical composition of the present invention may be used alone or in combination with surgery, hormone therapy, chemotherapy, and methods using biological response controller, for cancer or cancer metastasis.

The diagnosis and prognosis of cancer (or cancer metastasis) according to the present invention may be evaluated by detecting KRS proteins (especially, extracellularly exposed KRS N-terminal region) in the biological sample.

As used herein, the term "diagnosis" refers to identifying the presence or characteristics of a pathological condition. In the present invention, the diagnosis is to identify the occurrence or the likelihood (risk) of cancer or/and cancer metastasis or an immune cell migration-related disease.

The term "detection" is as described above, and the biological sample includes blood and other liquid samples having biological origins, biopsy specimens, solid tissue samples such as tissue culture, or cells derived therefrom. More specifically, examples of the biological sample may include, but are not limited to, tissues, extracts, cell lysates, whole blood, plasma, serum, saliva, ocular fluid, cerebrospinal fluid, sweat, urine, milk, ascites fluid, synovial fluid, peritoneal fluid, and the like. The sample may be obtained from animals, preferably mammals, and most preferably humans. The sample may be pre-treated before use for detection. Examples of the pretreatment may include filtration, distillation, extraction, concentration, interference ingredient deactivation, reagent addition, and the like. In addition, nucleic acids and proteins isolated from the sample may be used for detection.

The antibody or fragment thereof according to the present invention may be provided as a diagnostic kit. The kit is not particularly limited to the type thereof as long as the kit is known in the art as an assay kit that provides a peptide having an antibody or a particular binding domain as a component, and examples thereof include a kit for western blotting, ELISA, radioimmunoassay, radioimmunodiffusion, Ouchterlony immunodiffusion, rocket immunoelectrophoresis, immunohistochemistry, immunoprecipitation assay, complement fixation assay, FACS, a protein chip, or the like.

The antibody or fragment thereof of the present invention may be used in a kit, i.e., a packaged combination of reagents in predetermined amounts with instructions for performing the diagnostic assay. Where the antibody is labeled with an enzyme, the kit may include substrates and cofactors required by the enzyme (e.g., a substrate precursor which provides the chromophore or fluorophore). In addition, other additives may be included such as stabilizers, buffers (e.g., a block buffer or lysis buffer) and the like. The relative amounts of various reagents may be varied widely to provide concentrations in solution of the reagents which substantially optimize the sensitivity of the assay. The reagents may be provided as dry powders, usually lyophilized, including excipients which on dissolution will provide a reagent solution having an appropriate concentration.

In the present invention, the antibody is a polypeptide containing an Fc variant of a wild-type human IgG Fc region, and the Fc variant comprises at least one additional amino acid substitution as L117A, L118A, T182A, P212G of the wild-type human IgG1 Fc region defined by SEQ ID NO: 126 or T179A of the human IgG4 Fc region defined by SEQ ID NO: 138, the polypeptide is characterized in that it comprises a polypeptide having a reduced ADCC/CDC function compared to a polypeptide comprising a wild-type IgG Fc region.

In the present invention, the Fc region refers to the C-terminal region of an immunoglobulin heavy chain containing at least a part of the constant region, and includes a wild-type sequence Fc region and a variant Fc region. In the present invention, "Fc variant" refers to a polypeptide containing a modification in the Fc domain. The Fc variant of the present invention is defined according to the amino acid modification constituting it. Specifically, L118A is an Fc variant in which leucine is substituted for alanine at position 118, T182A is an Fc variant in which threonine is substituted for alanine at position 182, and P212G is an Fc variant in which proline is substituted for glycine at position 212 when compared to the parental Fc polypeptide. Amino acid modifications can be amino acid additions, amino acid deletions or amino acid substitutions. Amino acid substitutions can include naturally occurring amino acids and non-naturally occurring amino acids. Variants may include non-natural amino acids.

The "amino acid substitution" refers to the replacement of one or more existing amino acid residues by another different "replacement" amino acid residue within a given amino acid sequence.

Replacement residues or residues may be "naturally occurring amino acid residues" (ie, encoded by the genetic code), and may be selected from the group consisting of alanine (Ala); Arginine (Arg); Asparagine (Asn); Aspartic acid (Asp); Cysteine (Cys); Glutamine (Gln); Glutamic acid (Glu); Glycine (Gly); Histidine (His); Isoleucine (Ile): leucine (Leu); Lysine (Lys); Methionine (Met); Phenylalanine (Phe); Proline (Pro); Serine (Ser); Threonine (Thr); Tryptophan (Trp); Tyrosine (Tyr); and valine (Val).

The "ADCC/CDC function" means an antibody-dependent cell-mediated cytotoxicity (Antibody-dependent cellular cytotoxicity, ADCC), and a complement-dependent cytotoxicity (complement-dependent cytotoxicity, CDC)

function. The "complement-dependent cytotoxicity" (CDC) refers to the lysis of antigen-expressing cells by the antibody of the present invention in the presence of complement. "Antibody-dependent cell-mediated cytotoxicity" (ADCC) refers to non-specific cytotoxic cells (E.g. natural killer (NK) cells, neutrophils, and macrophages) expressing Fc receptors (FcRs) that recognize bound antibodies in target cells and therefore, it refers to a cell-mediated reaction that dissolves the target cell. CDC and ADCC can be measured using assays well known and available in the art. (Examples of reference: U.S. Pat. Nos. 5,500,362 and 5,821,337, and Clynes et al. (1998) Proc. Natl. Acad. Sci. (USA) 95:652-656). The constant region of the antibody is important for the ability of the antibody to fix complement and mediate cell dependent cytotoxicity. Thus, the isotype of the antibody can be selected based on whether it is desirable for the antibody to mediate cytotoxicity.

Specifically, the antibody of the present invention is specifically an antibody containing a heavy chain comprising one or more amino acid sequences selected from amino acid sequences represented by SEQ ID NOs: 140, 142, 144, 146, 148, 150, 152 and a light chain comprising an amino acid sequence defined by SEQ ID NO: 91;

A heavy chain comprising one or more amino acid sequences selected from amino acid sequences defined by SEQ ID NOs: 140, 142, 144, 146, 148, 150, 152 and a light chain comprising an amino acid sequence defined by SEQ ID NO: 107;

A heavy chain comprising one or more amino acid sequences selected from amino acid sequences defined by SEQ ID NOs: 140, 142, 144, 146, 148, 150, 152 and a light chain comprising an amino acid sequence defined by SEQ ID NO: 109;

A heavy chain comprising one or more amino acid sequences selected from the amino acid sequences defined by SEQ ID NOs: 154, 156, 158, 160, 162, 164, 166 and a light chain comprising the amino acid sequence defined by SEQ ID NO: 107;

A heavy chain comprising one or more amino acid sequences selected from amino acid sequences defined by SEQ ID NOs: 154, 156, 158, 160, 162, 164, 166 and a light chain comprising an amino acid sequence defined by SEQ ID NO: 109;

A heavy chain comprising at least one amino acid sequence selected from among the amino acid sequences defined by SEQ ID NO: 168, 170, 172, 174, 176, 178, 180 and a light chain comprising an amino acid sequence defined by SEQ ID NO: 109;

A heavy chain comprising one or more amino acid sequences selected from amino acid sequences defined by SEQ ID NOs: 182, 184, 186, 188, 190, 192, and 194 and a light chain comprising an amino acid sequence defined by SEQ ID NO: 109;

A heavy chain comprising one or more amino acid sequences selected from amino acid sequences defined by SEQ ID NO: 224, 226, 228, 230, 232, 234, 236 and a light chain comprising an amino acid sequence defined by SEQ ID NO: 109;

A heavy chain comprising one or more amino acid sequences selected from amino acid sequences defined by SEQ ID NOs: 210, 212, 214, 216, 218, 220, 222 and a light chain comprising an amino acid sequence defined by SEQ ID NO: 109;

A heavy chain comprising one or more amino acid sequences selected from amino acid sequences defined by SEQ ID NOs: 224, 226, 228, 230, 232, 234, 236 and a light chain comprising an amino acid sequence defined by SEQ ID NO: 111;

A heavy chain comprising one or more amino acid sequences selected from amino acid sequences defined by SEQ ID NOs: 224, 226, 228, 230, 232, 234, 236 and a light chain comprising an amino acid sequence defined by SEQ ID NO: 113;

A heavy chain comprising one or more amino acid sequences selected from amino acid sequences defined by SEQ ID NOs: 224, 226, 228, 230, 232, 234, 236 and a light chain comprising an amino acid sequence defined by SEQ ID NO: 115;

A heavy chain comprising one or more amino acid sequences selected from amino acid sequences defined by SEQ ID NOs: 238, 240, 242, 244, 246, 248, 250 and a light chain comprising an amino acid sequence defined by SEQ ID NO: 111;

A heavy chain comprising one or more amino acid sequences selected from amino acid sequences defined by SEQ ID NOs: 238, 240, 242, 244, 246, 248, 250 and a light chain comprising an amino acid sequence defined by SEQ ID NO: 113;

A heavy chain comprising at least one amino acid sequence selected from the amino acid sequences defined by SEQ ID NO: 238, 240, 242, 244, 246, 248, 250 and a light chain comprising an amino acid sequence defined by SEQ ID NO: 115; or A heavy chain comprising at least one amino acid sequence selected from the amino acid sequences defined by SEQ ID NO: 196, 198, 200, 202, 204, 206, 208 and a light chain comprising the amino acid sequence defined by SEQ ID NO: 111

The present invention provides a composition for preventing or treating diseases related to immune cell migration, and a composition for diagnosing diseases related to immune cell migration, comprising the antibody or fragment thereof as an active ingredient.

In the present invention, the term immune cell migration-related disease, for example, may be selected from the group consisting of cardiovascular disease, fibrotic disease, inflammatory disease and Alport syndrome, but if excessive immune cell migration (and/or invasion) is known in the art as the major pathogenesis, then the specific type of disease is not particularly limited.

The cardiovascular disease may be, for example, selected from the group consisting of hypertension (including inflammatory complications caused by hypertension), pulmonary arterial hypertension, atherosclerosis, angina pectoris, myocardial infarction, ischemic cerebrovascular disease, arteriosclerosis, and mesenteric sclerosis, but the kind of the specific disease is not particularly limited.

The fibrotic disease may be selected from the group consisting of, for example, scleroderma, rheumatoid arthritis, Crohn's disease, ulcerative colitis, myelofibrosis, pulmonary fibrosis, hepatic fibrosis, liver cirrhosis, kidney fibrosis, glomerulosclerosis, myofibrosis, myofibrosis cordis, interstitial fibrosis, pancreatic fibrosis, splenic fibrosis, mediastinal fibrosis, vascular fibrosis, skin fibrosis, eye fibrosis, macular degeneration, joint fibrosis, thyroid fibrosis, endomyocardial fibrosis, peritoneal fibrosis, retroperitoneal fibrosis, progressive mass fibrosis, nephrogenic systemic fibrosis, systemic lupus erythematosus, hereditary fibrosis, infectious fibrosis, irritant fibrosis, fibrosis due to chronic autoimmunity, fibrosis due to antigen incompatibility during organ transplantation, fibrotic complications after surgery, fibrosis due to hyperlipidemia, fibrosis due to obesity, diabetic fibrosis, fibrosis due to hypertension, and occlusion due to stent insertion-related fibrosis, but the specific disease type is not particularly limited.

In the present invention, the inflammatory disease may preferably be selected from the group consisting of an autoimmune disease, inflammatory bowel disease, dermatitis (for example, atopic dermatitis, eczema, psoriasis, etc.), diabetic eye disease (diabetic retinopathy, etc.), peritonitis, osteomyelitis, cellulites, meningitis, encephalitis, pancreatitis, trauma-induced shock, bronchial asthma, rhinitis, sinusitis, tympanitis, pneumonia, gastritis, enteritis, cystic fibrosis, apoplexy (apoplexy, stroke, etc.), bronchitis, bronchiolitis, hepatitis (cirrhosis, non-alcoholic, steatohepatitis, etc.), nephritis (diabetic renal failure, etc.), proteinuria, arthritis (such as psoriatic arthritis, osteoarthritis), neuritis (diabetic neuropathy, multiple sclerosis, etc.), gout, spondylitis, Reiter's syndrome, polyarteritis nodosa, vasculitis, amyotrophic lateral sclerosis, Wegener's granulomatosis, hypercytokinemia, Polymyalgia rheumatica, articular cell arteritis, calcium crystalline arthritis, pseudogout, non-articular rheumatoid, bursitis, tendosynovitis, epicondylitis (tennis elbow), Charcot's joint, hemarthrosis, Henoch-Schonlein purpura, hypertrophic osteoarthritis, multicentric reticulocytoma, sarcoidosis, hemochromatosis, drepanocytosis, hyperlipoproteinemia, hypomagglobulinemia, hyperparathyroidism, acromegaly, Mediterranean fever, Behcet's disease, systemic lupus erythematosus, recurrent fever, psoriasis, multiple sclerosis, sepsis, septic shock, acute respiratory distress syndrome, multiple organs dysfunction, chronic obstructive pulmonary disease, acute lung injury, and broncho-pulmonary dysplasia, and also includes chronic inflammatory diseases, but the disease type is not particularly limited.

In the present invention, autoimmune diseases may be selected from the group consisting of rheumatoid arthritis, systemic scleroderma, systemic lupus erythematosus, psoriasis, asthma, ulcerative colitis, Behcet's disease, Crohn's disease, multiple sclerosis, dermatitis, collagen disease, vasculitis, arthritis, granulomatosis, organ specificity autoimmune diseases, ulcerative colitis and GvHD (graft-versus-host disease).

The chronic inflammatory disease refers to a condition in which they are chronicized with reference to the types of inflammatory diseases described above, and preferred examples thereof include asthma, atopic dermatitis, eczema, psoriasis, osteoarthritis, gout, psoriatic arthritis, cirrhosis, nonalcoholic steatohepatitis, chronic obstructive pulmonary disease, rhinitis, diabetic retinopathy, diabetic renal failure, diabetic neuropathy and multiple sclerosis, but are not limited thereto.

In addition, the antibody of the present invention may be administered in a pharmaceutically effective amount to an individual suffering from a disease related to immune cell migration. In the above, the term 'pharmaceutically effective amount' refers to an amount that exhibits a higher response compared to the negative control group, and preferably refers to an amount sufficient to treat diseases related to immune cell migration. The total effective amount of the antibody or fragment thereof of the present invention, the formulation of the composition, the method of administration and the route of administration are described above.

The pharmaceutical composition of the present invention can be used alone or in combination with surgery, hormone therapy, chemotherapy, and methods using biological response modifiers for the prevention or treatment of diseases related to immune cell migration.

Diagnosis and prognosis of diseases related to immune cell migration according to the present invention can be performed by detecting a KRS protein (especially, a KRS N-terminal region exposed on the extracellular membrane) in a biological sample.

In addition, the present invention provides the use of the antibody or fragment thereof for preparing an agent for preventing or inhibiting cancer and cancer metastasis.

In addition, the present invention provides a method for preventing or inhibiting cancer and cancer metastasis, administering an effective amount of a composition comprising the antibody or fragment thereof to an individual in need thereof.

In addition, the present invention provides the use of the antibody or fragment thereof for preparing an agent for cancer or cancer metastasis diagnosis.

The present invention provides a method for diagnosing cancer or cancer metastasis, the method comprising:

a) obtaining a biological sample from an individual (subject) suspected of cancer metastasis;

b) administering a composition comprising the antibody or a fragment thereof to the sample or subject;

c) detecting the expression level of the KRS protein in the sample or subject of step b); and d) comparing the expression level of the KRS protein with a normal control group, and diagnosing that cancer and cancer metastasis have occurred when the expression level of KRS is increased.

The present invention provides the use of the antibody or fragment thereof for preparing an agent for treatment of an immune cell migration-related disease.

The present invention provides the use of the antibody or fragment thereof for preparing an agent for diagnosis of an immune cell migration-related disease.

The present invention provides a method for treating an immune cell migration-related disease, administering an effective amount of a composition comprising the antibody or fragment thereof to a subject in need thereof.

The present invention provides a method for diagnosing an immune cell migration-related disease, the method comprising:

a) obtaining a biological sample from a subject suspected of an immune cell migration-related disease;

b) administering a composition comprising the antibody or a fragment thereof to the sample or subject;

c) detecting the expression level of the KRS protein in the sample or subject of step b); and d) comparing the expression level of the KRS protein with a normal control group, and diagnosing as an immune cell migration-related disease when the expression level of KRS is increased.

In one embodiment, the present invention provides a method of diagnosing and treating cancer and cancer metastasis comprising the steps of:

a) obtaining a biological sample from an individual (subject) suspected of cancer metastasis;

b) administering a composition comprising the antibody or a fragment thereof to the sample or subject;

c) detecting the expression level of the KRS protein in the sample or subject of step b); and d) comparing the expression level of the KRS protein with a normal control group, and diagnosing that cancer and cancer metastasis have occurred when the expression level of KRS is increased; and e) administering a therapeutic drug for treating cancer and cancer metastasis to the diagnosed individual or treating the disease through surgery.

In one embodiment, the present invention provides a method for diagnosing and treating diseases related to immune cell migration, comprising the steps of:

a) obtaining a biological sample from a subject suspected of an immune cell migration-related disease;

b) administering a composition comprising the antibody or a fragment thereof of claim 1 to the sample or subject;

c) detecting the expression level of the KRS protein in the sample or subject of step b); and d) comparing the expression level of the KRS protein with a normal control group, and diagnosing as an immune cell migration-related disease when the expression level of KRS is increased.

e) administering a therapeutic drug for treating a disease related to immune cell migration to the diagnosed individual or treating the disease through surgery.

The step e) is a step of performing treatment of the disease to the individual whose disease is diagnosed in the step d) through means such as administration of therapeutic drugs or surgery.

The 'treatment' of the present invention generally refers to improving the symptoms of cancer and cancer metastasis or immune cell migration related disease, this may include curing, substantially preventing, or improving the condition of cancer and cancer metastasis or immune cell migration related diseases, and it includes, but is not limited to, alleviating, curing, or preventing one symptom or most of the symptoms resulting from the disease.

The therapeutic drug is not particularly limited as long as it is a kind of drug commonly used for the treatment of cancer, cancer metastasis, or immune cell migration related diseases, and in one embodiment, it may be to treat one or more drugs selected from the group consisting of an anti-cancer agent, an anti-inflammatory agent (such as a steroid agent as a representative example), and a pulmonary arterial hypertension therapeutic agent, but is not limited thereto.

The therapeutic drug is administered to an individual in a 'therapeutically effective amount', and the therapeutically effective amount can be determined by those skilled in the art, the effective dose for a patient can be determined by considering various factors such as the severity of the patient, diet and excretion rate as well as the patient's age, weight, health condition, sex, and disease. The route of administration of the therapeutic drug is not particularly limited, and may be administered orally or parenterally, and includes both local administration as well as systemic administration. The parenteral administration may be, but is not limited to, intranasal drug application, subcutaneous injection, and the like, and as another example, intramuscular injection, intravenous injection, or the like may be used.

As used herein, the term "comprising" is used synonymously with "containing" or "being characterized", and does not exclude additional ingredients or steps not mentioned in the composition or method. The term "consisting of" means excluding additional elements, steps, or ingredients not otherwise specified. The term "essentially consisting of" means including the mentioned elements or steps as well as any element or step that does not substantially affect basic characteristics of the mentioned elements or steps in the scope of compositions or methods.

Advantageous Effect

Accordingly, the present invention provides an antibody that has a specific CDR (complementarity determining region) sequence described herein and specifically binds to the KRS N-terminal region exposed to the extracellular membrane. The method of the present invention can be usefully used to prepare an antibody having a higher affinity for the KRS N-terminus than a conventional antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR CARRYING OUT INVENTION

Hereinafter, the present invention will be described in detail.

However, the following examples are merely for illustrating the present invention and are not intended to limit the scope of the present invention.

Example 1: Construction of Yeast Cell Surface Expression Library for Increasing Affinity The affinity for the N-terminus of the antibody N3 (application number: 10-2018-0035446) targeting the N-terminus of the existing KRS is about 150 nM, which is lower than that of various antibodies in the complete IgG form. Accordingly, in order to increase the affinity to prepare an antibody having a better effect, the light chain variable region and the heavy chain variable region of the N3 antibody were improved.

Homology model was used to predict the approximate structure of N3, through which random mutations were introduced into the CDR regions predicted to play an important role in antigen binding. Specifically, in the library based on the heavy chain variable region, NNK, a degenerated codon, which can contain all 20 amino acid sequences for CDR3 residues was used. In the library based on the light chain variable region, NNK, a degenerated codon that can contain all 20 amino acid sequences, was used for CDR3 residues.

Specifically, the DNA encoding the designed library was amplified using a PCR technique and then concentrated using an ethanol precipitation method.

Yeast surface expression vector (C-aga2), which expresses aga2 protein at the C-terminus for homologous recombination, is treated with NheI and MluI restriction enzymes and purified using agarose gel extraction method and concentrated ethanol precipitation method.

Restriction enzyme-treated 4 μg vectors for 12 μg of each library-encoding DNA were transformed into yeast EBY100 for expression on the yeast surface by electroporation, and the library size was confirmed by measuring the number of colonies grown in the selective medium SD-CAA (20 g/L Glucose, 6.7 g/L Yeast nitrogen base without amino acids, 5.4 g/L Na$_2$HPO$_4$, 8.6 g/L NaH$_2$PO$_4$, 5 g/L casamino acids) through serial dilution.

Figure 1:
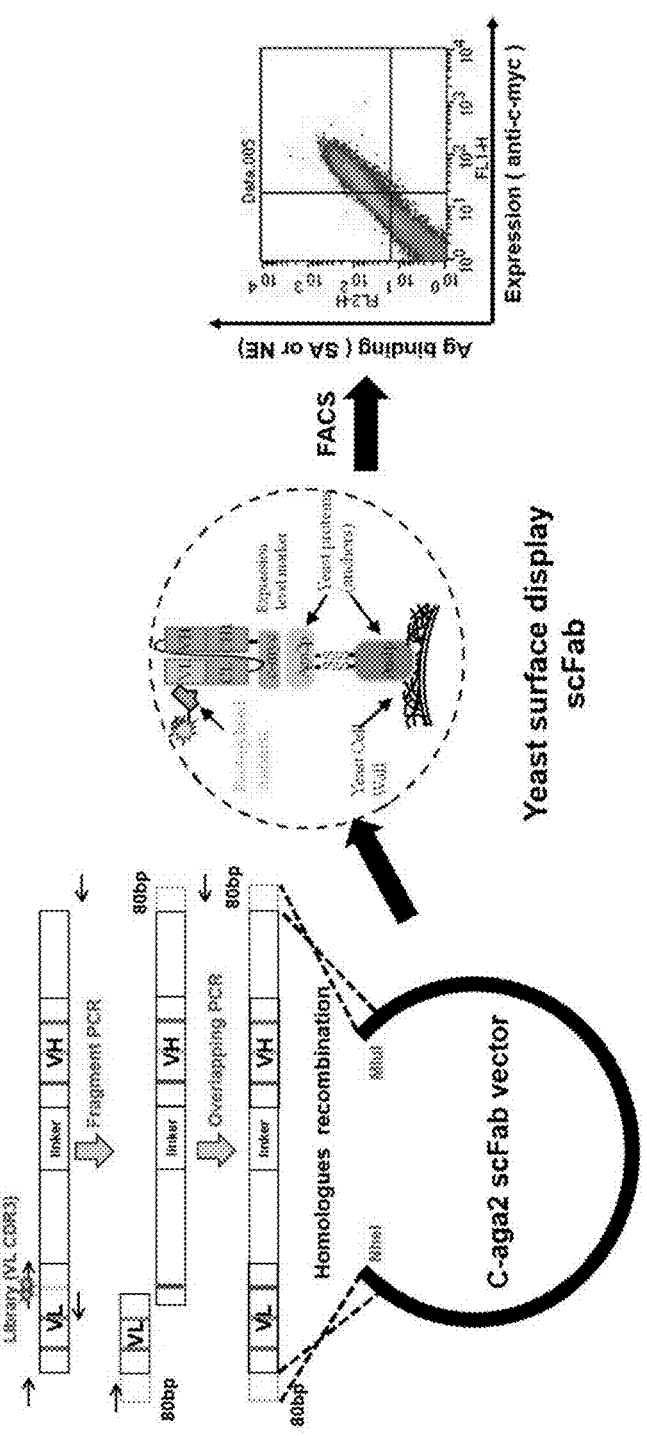
FIG. 1 is shown in a schematic diagram of selection and construction strategy of two libraries constructed based on each of the heavy chain variable region (VH) and light chain variable region (VL) of N3 in order to improve the affinity of the KRS N-terminal target antibody N3 to the KRS N-terminus.

This process is shown in FIG. 1.

Example 2: Selection of Light Chain Variable Region (VL) and Heavy Chain Variable Region (VH) with Improved Affinity to GST-Conjugated KRS (1-72) Peptide Two types of N3-based affinity improving libraries constructed in Example 1 were selected using GST-conjugated KRS (1-72) peptide as an antigen.

Specifically, a 10 nM level of purified GST-conjugated KRS (1-72) peptide was incubated with yeasts expressing a single-chain Fab (scFab)-type light chain variable region library on the cell surface using SG-CAA medium (20 g/L Galactose, 6.7 g/L Yeast nitrogen base without amino acids, 5.4 g/L Na$_2$HPO$_4$, 8.6 g/L NaH$_2$PO$_4$, 5 g/L casamino acids) for 1 hour at room temperature for primary FACS screening.

Thereafter, the GST-conjugated KRS (residues 1-72) peptide and yeasts expressing the library were reacted with PE-conjugated Streptavidin-R-phycoerythrin conjugate (SA-PE) at 4° C. for 20 minutes and were suspended by FACS (Fluorescence activated cell sorting, FACS Caliber; BD biosciences). Subsequently, a second FACS screening was performed with 1 nM KRS (residues 1-72) peptide conjugated with GST, and a third FACS screening was performed with 0.5 nM KRS (residues 1-72) peptide conjugated with GST.

Figure 2A:
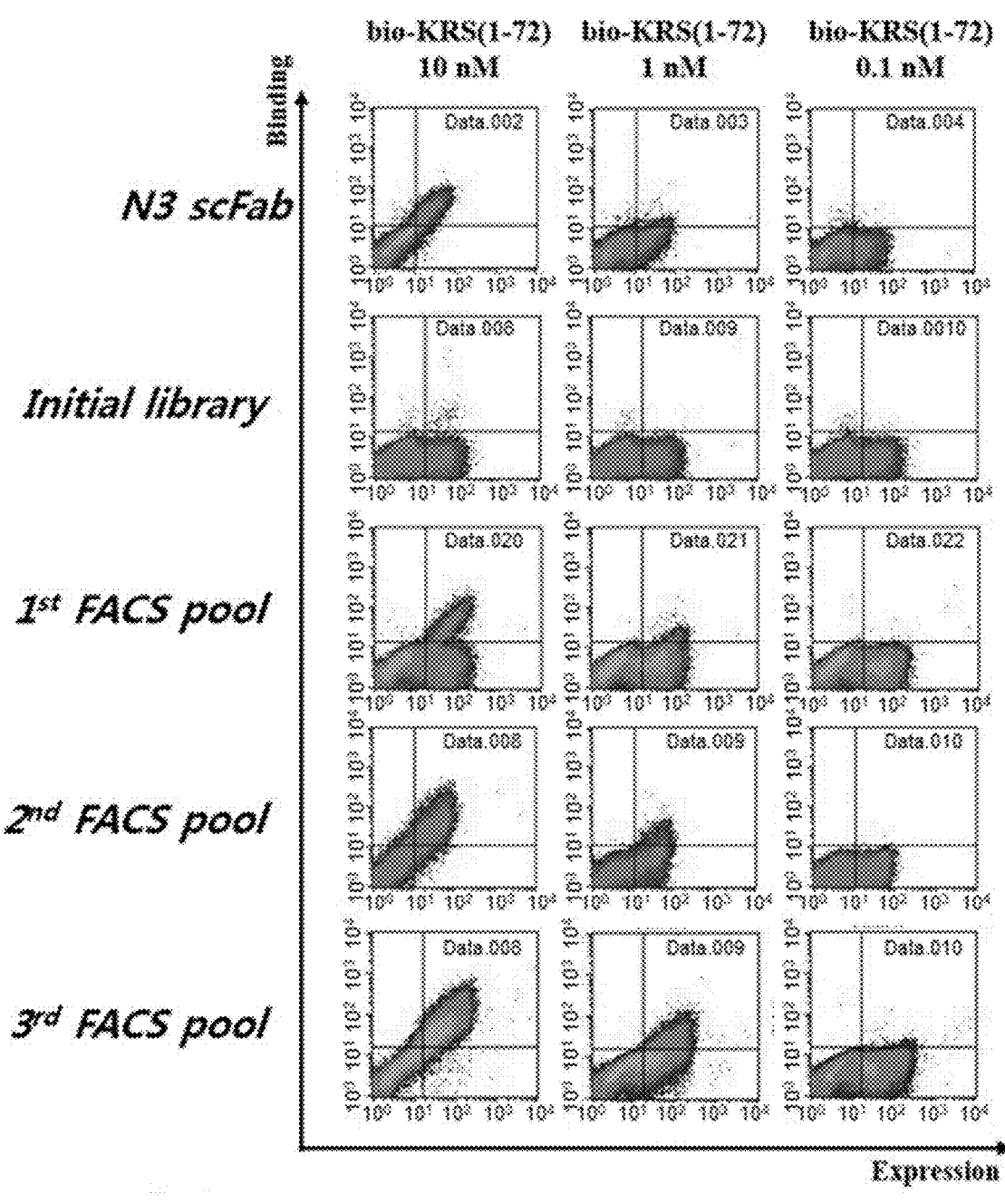
FIG. 2a shows the results of analysis of the KRS (1-72) peptide bound to 10 nM, 1 nM or 0.1 nM GST and the analyzed binding capacity by flow cytometry (FACS) for each step library-expressing yeast selected using FACS (Fluorescence Activated Cell Sorting).
Figure 2B:
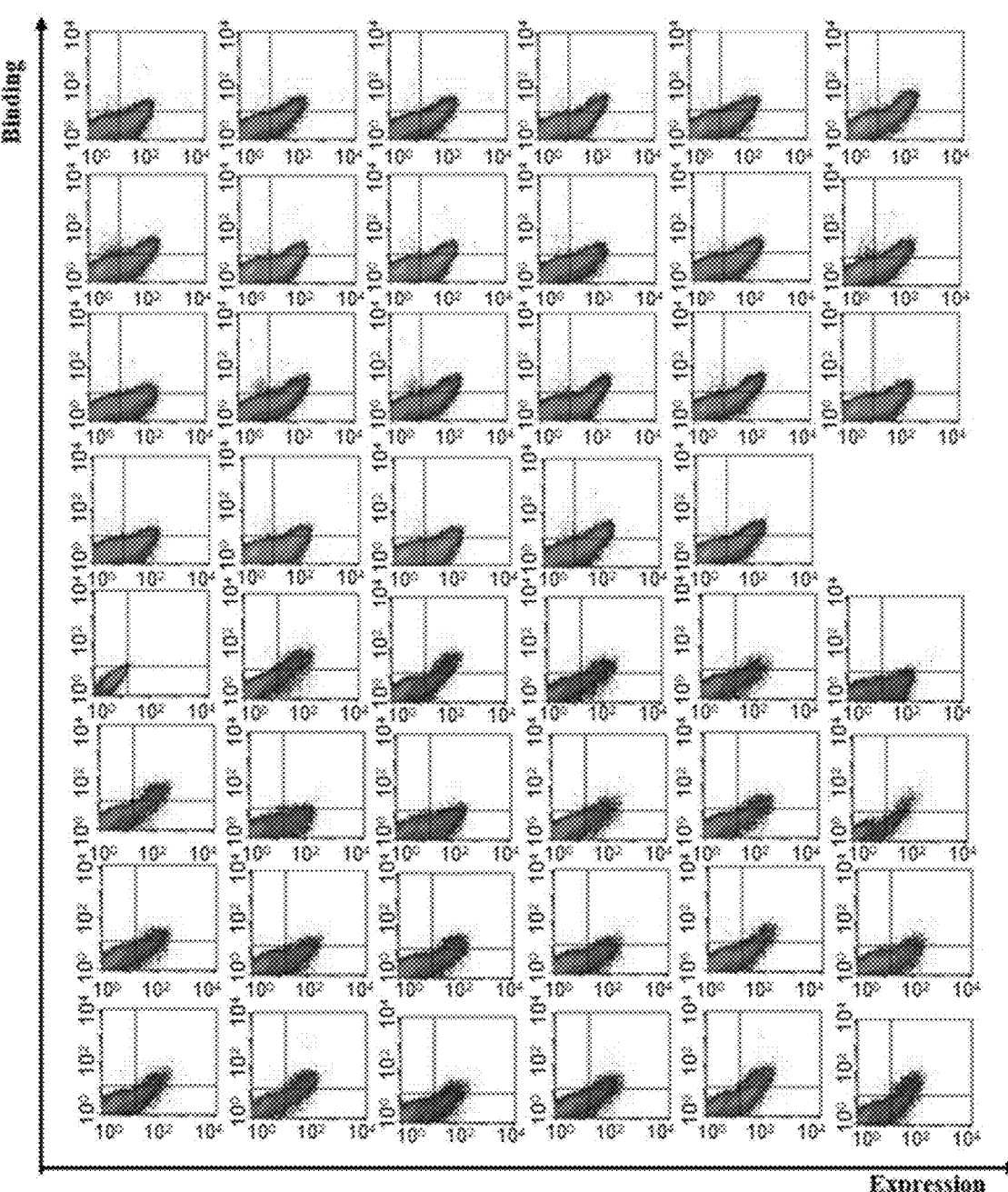
FIG. 2b shows the results of analyzing the KRS (1-72) peptide bound to 0.1 nM GST and the binding ability with a flow cytometer for yeasts expressing 47 individual clones in the final selected library.

As a result, as shown in FIGS. 2a and 2b, through the selection process using FACS, compared with the N3 antibody, it was confirmed that clones having high affinity for the GST-conjugated KRS (1-72) peptide were selected and the affinity was dependent to a heavy chain variable region (VH) or light chain variable region (VL). Three unique clones (N3-1, N3-3, and N3-4) having high affinity and specificity for GST-conjugated KRS (1-72) peptide were selected through individual clone binding ability analysis. In addition, another unique clone (N3-5) was constructed by combining the light chain variable region and the heavy chain variable region with each other. That is, a total of four unique clones (N3-1, N3-3, N3-4, N3-5) were selected.

Table 1 shows the CDR sequences of the light chain variable region and the heavy chain variable region of four individual clones showing high binding ability to GST-conjugated KRS (1-72) peptide. Table 2 shows the heavy chain variable region sequence and the light chain variable region sequence.

TABLE 1

| | Heavy | | | Light | | |
|---|---|---|---|---|---|---|
| | CDR H1 | CDR H2 | CDR H3 | CDR L1 | CDR L2 | CDR L3 |
| N3 | SYDMS (SEQ ID NO: 1) | AISYDNGNTY YADSVKG (SEQ ID NO: 3) | MALDFDY (SEQ ID NO: 5) | TGSSSNIGSN YVT (SEQ ID NO: 7) | DNSNRPS (SEQ ID NO: 9) | ASWDDSLSAY V (SEQ ID NO: 11) |
| N3-1 | SYDMS (SEQ ID NO: 1) | AISYDNGNTY YADSVKG (SEQ ID NO: 3) | MALDFDY (SEQ ID NO: 5) | TGSSSNIGSN YVT (SEQ ID NO: 7) | DNSNRPS (SEQ ID NO: 9) | ASFSDELGAY V (SEQ ID NO: 13) |
| N3-3 | SYDMS (SEQ ID NO: 1) | AISYDNGNTY YADSVKG (SEQ ID NO: 3) | MALDFDY (SEQ ID NO: 5) | TGSSSNIGSN YVT (SEQ ID NO: 7) | DNSNRPS (SEQ ID NO: 9) | SSFSDELGAY V (SEQ ID NO: 15) |
| N3-4 | SYDMS (SEQ ID NO: 1) | VISSDGGNTY YADSVKG (SEQ ID NO: 118) | MALDFDY (SEQ ID NO: 5) | TGSSSNIGSN YVT (SEQ ID NO: 7) | DNSNRPS (SEQ ID NO: 9) | ASFSDELGAY V (SEQ ID NO: 13) |
| N3-5 | SYDMS (SEQ ID NO: 1) | VISSDGGNTY YADSVKG (SEQ ID NO: 118) | MALDFDY (SEQ ID NO: 5) | TGSSSNIGSN YVT (SEQ ID NO: 7) | DNSNRPS (SEQ ID NO: 9) | SSFSDELGAY V (SEQ ID NO: 15) |

TABLE 2

| | | Sequence | SEQ ID NO: (Sequence name) |
|---|---|---|---|
| N3 | VH | EVQLLESGGGLVQPGGSLRLSCAASGFTF SSYDMSWVRQAPGKGLEWVSAISYDNGN TYYADSVKGRFTISRDNSKNTLYLQMNSLR AEDTAVYYSARMALDFDYWGQGTLVTVSS | SEQ ID NO: 31 (N3 VH) |
| | VL | QSVLTQPPSASGTPGQRVTISCTGSSSNIG SNYVTWYQQLPGTAPKLLIYDNSNRPSGV PDRFSGSKSGTSASLAISGLRSEDEADYYC ASWDDSLSAYVFGGGTKLTVL | SEQ ID NO: 33 (N3 VL) |

TABLE 2-continued

| Sequence | SEQ ID NO: (Sequence name) |
|---|---|
| N3-1 VH | EVQLLESGGGLVQPGGSLRLSCAASGFTF SSYDMSWVRQAPGKGLEWVSAISYDNGN TYYADSVKGRFTISRDNSKNTLYLQMNSLR AEDTAVYYSARMALDFDYWGQGTLVTVSS | SEQ ID NO: 31 (N3 VH) |
| VL | QSVLTQPPSASGTPGQRVTISCTGSSSNIG SNYVTWYQQLPGTAPKLLIYDNSNRPSGV PDRFSGSKSGTSASLAISGLQSEDEADYYC ASFSDELgAYVFGGGTKLTVL | SEQ ID NO: 49 (N3 VL mutant 1) |
| N3-3 VH | EVQLLESGGGLVQPGGSLRLSCAASGFTF SSYDMSWVRQAPGKGLEWVSAISYDNGN TYYADSVKGRFTISRDNSKNTLYLQMNSLR AEDTAVYYSARMALDFDYWGQGTLVTVSS | SEQ ID NO: 31 (N3 VH) |
| VL | QSVLTQPPSASGTPGQRVTISCTGSSSNIG SNYVTWYQQLPGTAPKLLIYDNSNRPSGV PDRFSGSKSGTSASLAISGLQSEDEADYYC SSFSDELgAYVFGGGTKLTVL | SEQ ID NO: 51 (N3 VL mutant 2) |
| N3-4 VH | EVQLLESGGGLVQPGGSLRLSCAASGFTF SSYDMSWVRQAPGKGLEWVSVISSDGGN TYYADSVKGRFTISRDNSKNTLYLQMNSLR AEDTAVYYSARMALDFDYWGQGTLVTVSS | SEQ ID NO: 35 (N3 VH mutant 1) |
| VL | QSVLTQPPSASGTPGQRVTISCTGSSSNIG SNYVTWYQQLPGTAPKLLIYDNSNRPSGV PDRFSGSKSGTSASLAISGLQSEDEADYYC ASFSDELgAYVFGGGTKLTVL | SEQ ID NO: 49 (N3 VL mutant 1) |
| N3-5 VH | EVQLLESGGGLVQPGGSLRLSCAASGFTF SSYDMSWVRQAPGKGLEWVSVISSDGGN TYYADSVKGRFTISRDNSKNTLYLQMNSLR AEDTAVYYSARMALDFDYWGQGTLVTVSS | SEQ ID NO: 35 (N3 VH mutant 1) |
| VL | QSVLTQPPSASGTPGQRVTISCTGSSSNIG SNYVTWYQQLPGTAPKLLIYDNSNRPSGV PDRFSGSKSGTSASLAISGLQSEDEADYYC SSFSDELgAYVFGGGTKLTVL | SEQ ID NO: 51 (N3 VL mutant 2) |

35

In addition, ELISA was performed to measure the affinity for the N-terminus of KRS to confirm whether the affinity for the N-terminus of KRS was increased.

Specifically, the N-terminal region (residues 1-72) peptide of KRS was coated in a 96-well EIA/RIA plate (COSTAR Corning) at 25° C. for 1 hour, and the plate was washed 3 times with PBS (pH 7.4, 137 mM NaCl, 12 mM phosphate, 2.7 mM KCl) (SIGMA) for 10 minutes. Thereafter, 4% BSA PBS (4% Bovine Serum Albumin, pH7.4, 137 mM NaCl, 12 mM phosphate, 2.7 mM KCl) (SIGMA) was treated for 1 hour, and then washed 3 times with PBS for 10 minutes. Then, the N3 antibody, N3-1 antibody, N3-3 antibody, N3-4 antibody, and N3-5 antibody of IgG-type were treated and incubated, respectively, and then the plate was washed three times with 0.1% PBST for 10 minutes. As a labeled antibody, horseradish peroxidase-conjugated anti-human mAb (SIGMA) was used. Then, it was reacted with TMB (3,3', 5,5'-Tetramethylbenzidine) (Sigma) and the absorbance was measured at 450 nm to quantify the antibody binding.

Figure 3A:
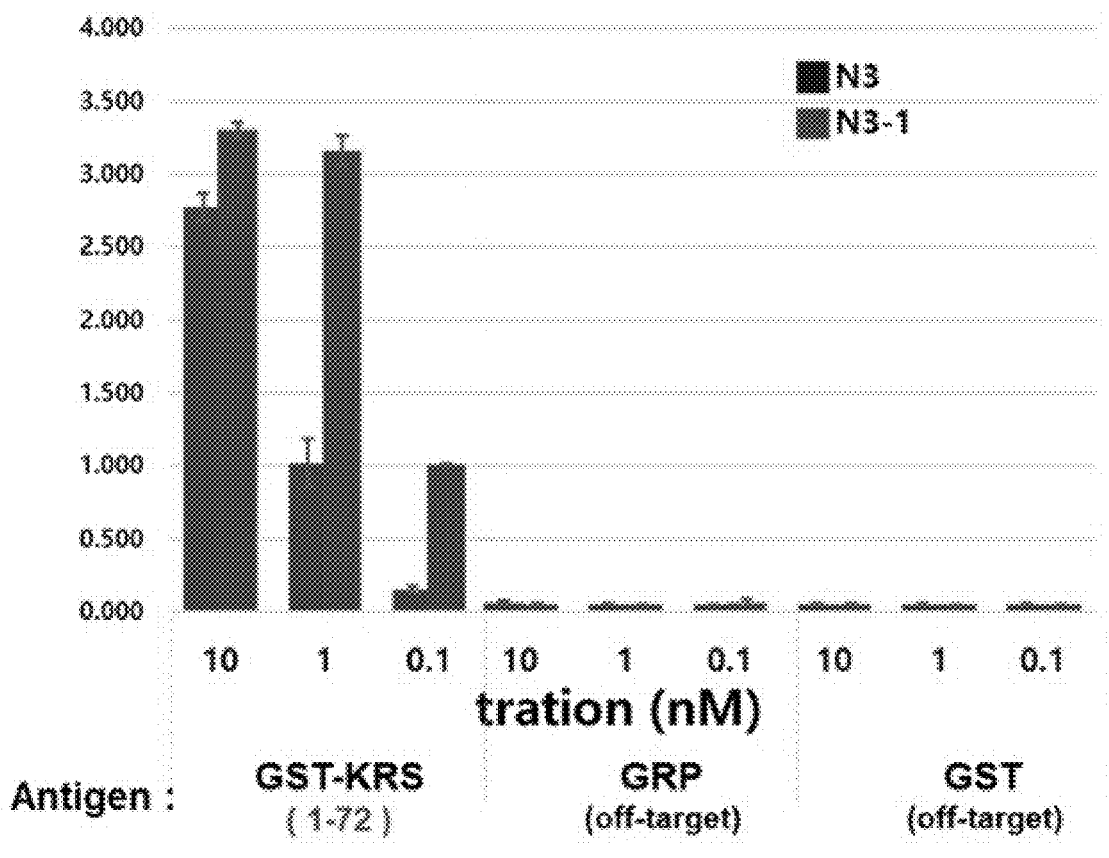
FIGS. 3a and 3b show ELISA results for measuring affinity for the N-terminus of KRS of the N3-1 antibody, N3-3 antibody, N3-4 antibody and N3-5 antibody selected as having high affinity and specificity for the peptide of KRS N-term (residues 1-72).
Figure 3B:
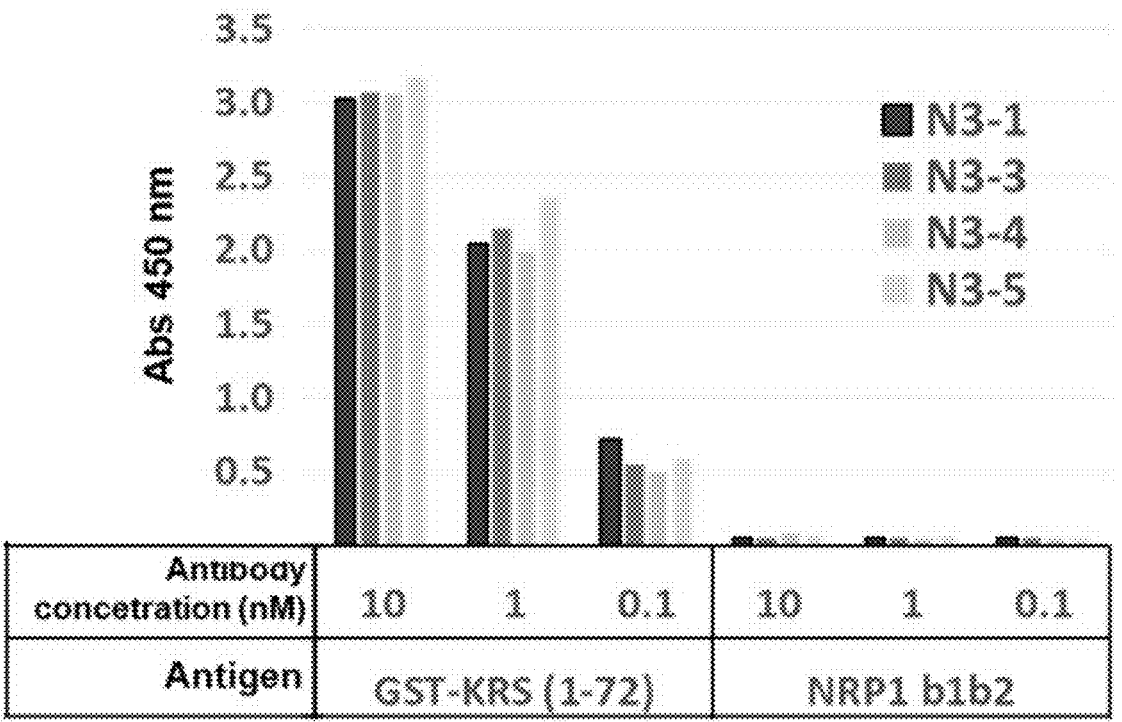

As a result, as shown in FIGS. 3a and 3b, it was confirmed that the affinity of the mutant N3-1, N3-3, N3-4, and N3-5 antibodies was increased compared to the wild-type N3 antibody. It was found that all clones did not bind to GST or NRP1-b1b2 used as a negative control. There was no significant difference in KRS binding ability between mutant antibodies N3-1, N3-3, N3-4, and N3-5.

Example 3: Comparison of Affinity Between N3 Antibody and N3-1 Antibody 3-1. Cell Migration Inhibitory Effect of Antibody Among the N3 mutant antibodies of Example 2, the N3-1 antibody was converted to an IgG antibody using a conven-tional method. The following experiment was performed using the converted IgG antibody.

Cell migration was measured using a 24-well transwell chamber having a commonly used polycarbonate membrane (8.0 µm pore size, Costar). The lower well was coated with 10 µg Laminin In the transwell chamber. Then, A549 cells were suspended in serum-free RPMI medium, and placed in the upper chamber at a concentration of $1 \times 10^5$ cells per well. N3, N3-1 IgG, and human mock IgG (control) were treated in the chamber at 10 nM or 100 nM, respectively, and incubated for 24 hours. The non-migrating cells present above the membrane were removed with a cotton swab. Then, it was washed twice with PBS and treated with 70% MeOH (in PBS) for 30 minutes. After washing twice with PBS, hematoxylin solution was treated for 30 minutes. Then, after washing the chamber three times with DW, the mem-brane in the chamber was cut and mounted on a slide glass to observe.

Figure 4:
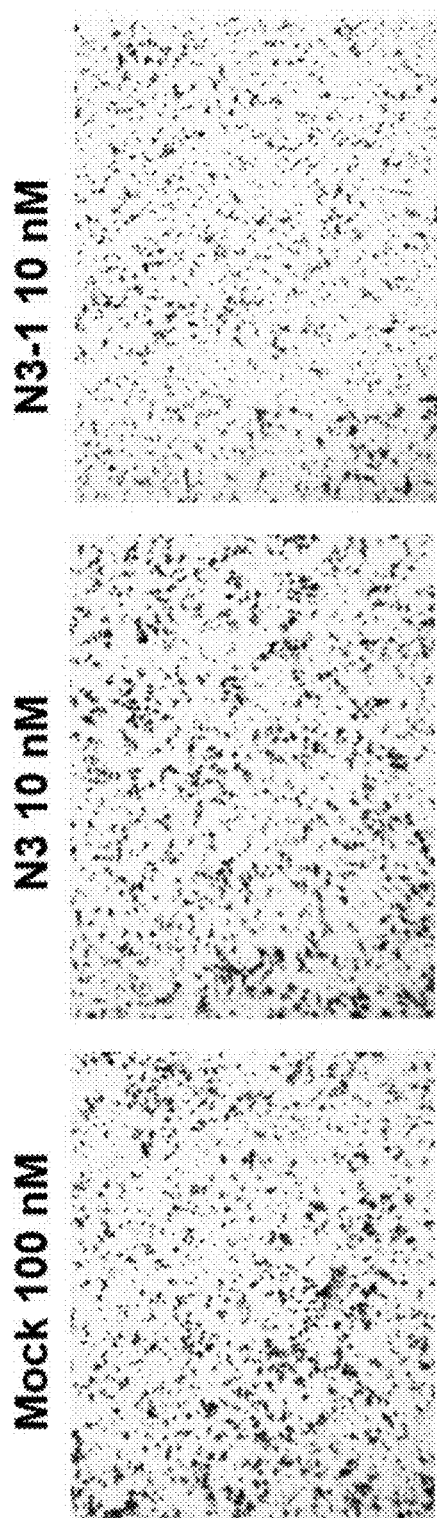
FIG. 4 shows the results of confirming the cell migration inhibitory effect of the N3 antibody and the N3-1 antibody.

As a result, as shown in FIG. 4, it was confirmed that the N3-1 antibody significantly inhibited the migration of A549 cells compared to the N3 antibody.

3-2. KRS Affinity Effect of Antibody

Using the purified protein of the KRS fragment (1-207aa) as an antigen, the binding ability to N3 and N3-1 antibodies was analyzed via Surface Plasmon Resonance (SPR).

The SPR experiment was performed using a Biacore T200 (GE Healthcare) equipped with a Series S sensor chip CM5 (GE Healthcare) at 25° C. After the antibody was immobi-lized on the chip using an amine coupling kit (GE Health-care), the antigen was diluted 4 times in PBS solution in the range of 4.8 nM-1250 nM and flowed for 60 seconds.

Thereafter, PBS was flowed for 300 seconds. The obtained data was analyzed with Biacore T200 Evaluation software v2.0 (GE Healthcare).

Figure 5:
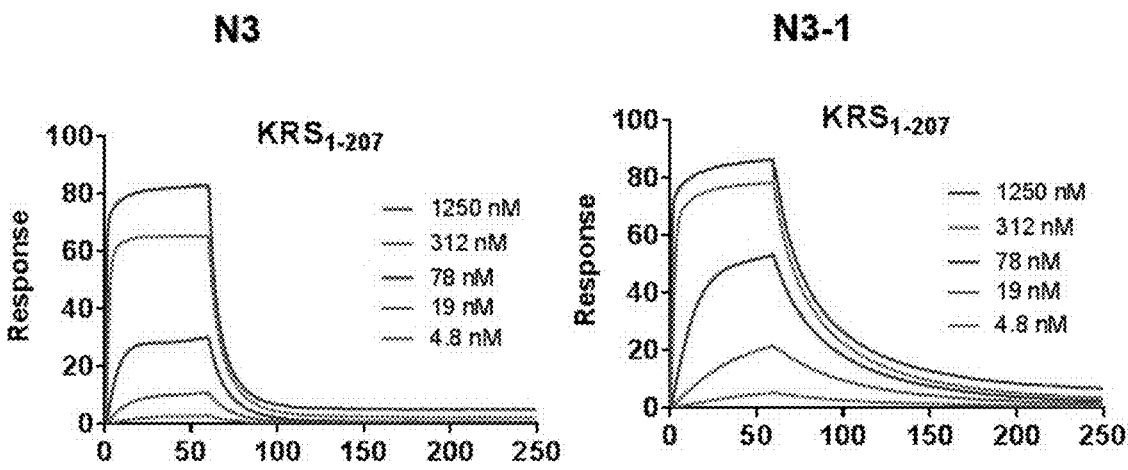
FIG. 5 shows the result of comparing the affinity for KRS of N3 antibody and N3-1 antibody by SPR (surface plasmon resonance) method.

As a result, as shown in FIG. 5, the KD value of the N3-1 antibody was measured to be 31 nM, indicating that the binding ability to the KRS protein was increased compared to the N3 antibody.

Example 4: Construction of Yeast Cell Surface Expression Library for Affinity Enhancement (N 3-1 Antibody)

The N3-1, N3-3, N3-4, and N3-5 antibodies targeting the KRS N-terminus derived in the Example 2 have similar affinity to KRS, and as shown in the result of the N3-1 antibody, it was determined to have an affinity of about 31 nM. This is still low compared to the affinity of the various antibodies in the complete IgG form. In order to increase the affinity and obtain a more effective antibody, it was attempted to intensively improve the heavy chain variable region of the antibody.

The light chain variable region sequence was fixed to N3-3, and the approximate modeling structure of N3-3 was predicted using homology modeling. Through this, a random mutation was introduced into the CDR predicted to play an important role in antigen binding.

Specifically, the residues of the CDR2 and CDR3 of the heavy chain variable region used NNK, a degenerated codon that can contain all 20 amino acid sequences, and a library was constructed in the same manner as in Example 1.

Example 5. Selection of Light Chain Variable Region (VL) and Heavy Chain Variable Region (VH) with Improved Affinity to GST-Conjugated KRS (1-72) Peptide Using the GST-conjugated KRS (residues 1-72) peptide as an antigen, two types of N3-3-based affinity improving libraries constructed in the Example 4 were selected. Since the affinity of N3-3 and N3-1 was expected to be almost the same and the sequences were almost similar, the comparative experiment was performed with N3-1.

Specifically, the yeasts expressing the library bound with the GTP-conjugated KRS (resides 1-72) peptide were reacted with Streptavidin Microbead™ (Miltenyi Biotec) at 4° C. for 20 minutes, and yeasts expressing the heavy chain variable region with high affinity to the KRS (1-72 aa) peptide were suspended using magnetic activated cell sorting (MACS). The yeasts expressing the library selected through the MACS was cultured in SG-CAA (20 g/L Galactose, 6.7 g/L Yeast nitrogen base without amino acids, 5.4 g/L $Na_2HPO_4$, 8.6 g/L $NaH_2PO_4$, 5 g/L casamino acids) medium to induce library expression. Subsequently, in the same manner as in the Example 2, sequential screening was performed using FACS.

The primary FACS screening was performed with 10 nM KRS (1-72) peptide conjugated with GST, the secondary FACS screening with 1 nM KRS (1-72) peptide conjugated with GST, the third FACS screening was performed with 0.5 nM KRS (1-72) peptide conjugated with GST, and the forth FACS screening was performed with 0.1 nM KRS (1-72) peptide conjugated with GST.

Figure 6:
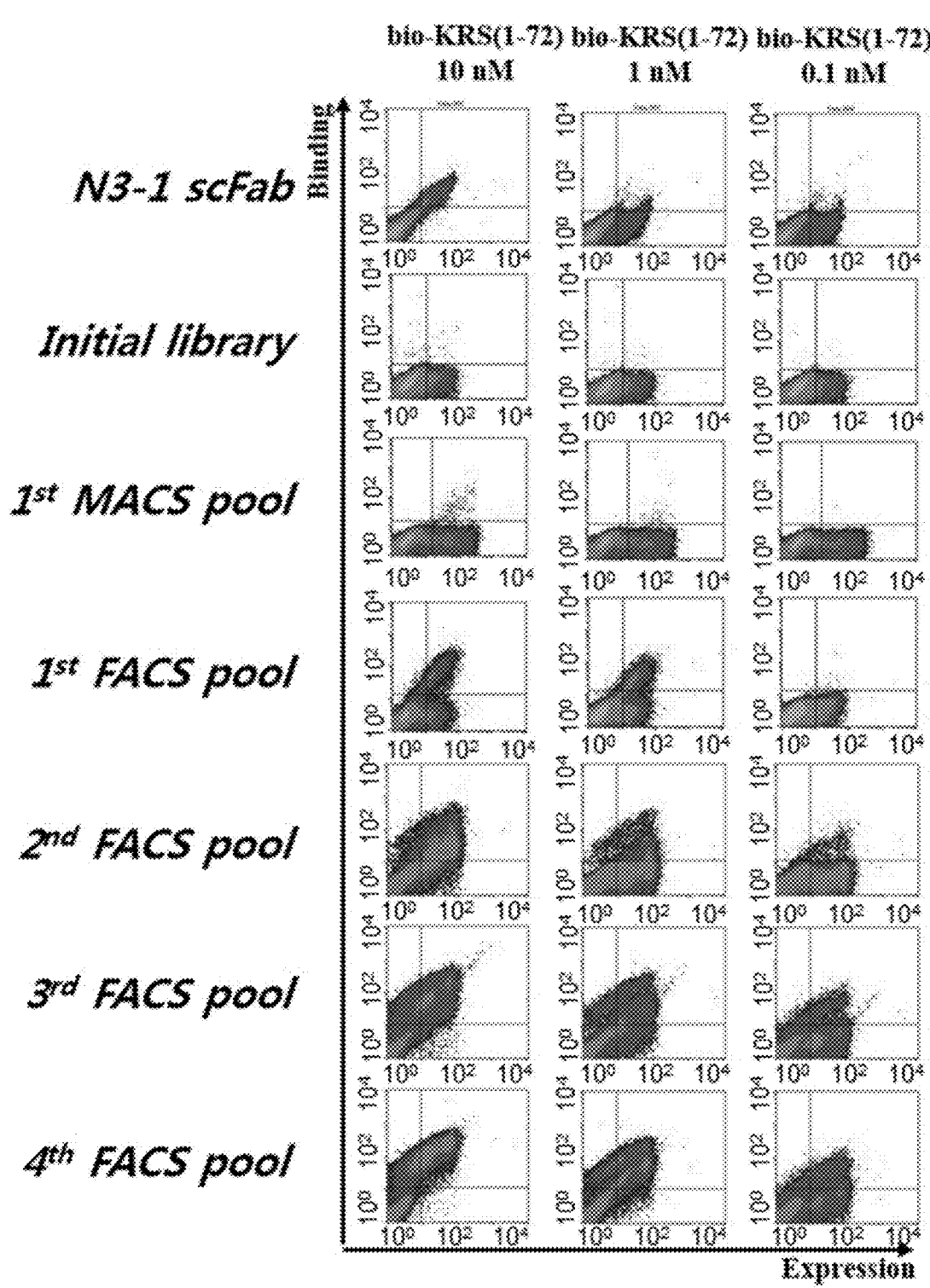
FIG. 6 shows the results of analysis of the KRS (1-72) peptide bound to 10 nM, 1 nM or 0.1 nM GST and binding ability analyzed with by flow cytometer for each step library-expressing yeast selected using MACS and FACS (Fluorescence Activated Cell Sorting)

As a result, as shown in FIG. 6, through the selection process using MACS and FACS (Fluorescence Activated Cell Sorting), it was confirmed that clones having high affinity depending on the heavy chain variable region (VH) for the GST-conjugated KRS (1-72) peptide were selected compared with the N3-1 antibody, and four unique clones (N3-6, N3-7, N3-8, N3-9) having high affinity and specificity for GST-conjugated KRS (1-72) peptide were selected through individual clone binding ability analysis.

The CDR sequences of the light chain variable region and heavy chain variable region of four individual clones, which show high binding ability to the KRS (1-72 aa) peptide, were shown in Table 3, and Table 4 shows the sequences of heavy chain variable region sequence and light chain variable region.

TABLE 3

| | Heavy | | | Light | | |
|---|---|---|---|---|---|---|
| | CDR H1 | CDR H2 | CDR H3 | CDR L1 | CDR L2 | CDR L3 |
| N3-6 | SYDMS (SEQ ID NO: 1) | AISPQMGRV YYADSVKG (SEQ ID NO: 17) | MALDFDY (SEQ ID NO: 5) | TGSSSNIG SNYVT (SEQ ID NO: 7) | DNSNRPS (SEQ ID NO: 9) | SSFSDELGA YV (SEQ ID NO: 15) |
| N3-7 | SYDMS (SEQ ID NO: 1) | AIDPLGGNIY YADSVKG (SEQ ID NO: 19) | MALDFDY (SEQ ID NO: 5) | TGSSSNIG SNYVT (SEQ ID NO: 7) | DNSNRPS (SEQ ID NO: 9) | SSFSDELGA YV (SEQ ID NO: 15) |
| N3-8 | SYDMS (SEQ ID NO: 1) | AISPYSGRIY YADSVKG (SEQ ID NO: 21) | MALDFDY (SEQ ID NO: 5) | TGSSSNIG SNYVT (SEQ ID NO: 7) | DNSNRPS (SEQ ID NO: 9) | SSFSDELGA YV (SEQ ID NO: 15) |
| N3-9 | SYDMS (SEQ ID NO: 1) | AIGADGGPS YYADSVKG (SEQ ID NO: 23) | MALDFDY (SEQ ID NO: 5) | TGSSSNIG SNYVT (SEQ ID NO: 7) | DNSNRPS (SEQ ID NO: 9) | SSFSDELGA YV (SEQ ID NO: 15) |

TABLE 4

| | | Sequence | SEQ ID NO: (Sequence name) |
|---|---|---|---|
| N3-6 | VH | EVQLLESGGGLVQPGGSLRLSCAASGFTF SSYDMSWVRQAPGKGLEWVSAISPQMGR VYYADSVKGRFTISRDNSKNTLYLQMNSLR AEDTAVYYSARMALDFDYWGQGTLVTVSS | SEQ ID NO: 37 (N3 VH mutant 2) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYYC SSFSDELgAYVFGGGTKLTVL | SEQ ID NO: 51 (N3 VL mutant 2) |
| N3-7 | VH | EVQLLESGGGLVQPGGSLRLSCAASGFTF SSYDMSWVRQAPGKGLEWVSAIDPLGGNI YYADSVKGRFTISRDNSKNTLYLQMNSLRA EDTAVYYSARMALDFDYWGQGTLVTVSS | SEQ ID NO: 39 (N3 VH mutant 3) |
| | VL | QSVLTQPPSASGTPGQRVTISCTGSSSNIG SNYVTWYQQLPGTAPKLLIYDNSNRPSGV VPDRFSGSKSGTSASLAISGLQSEDEADYYC SSFSDELgAYVFGGGTKLTVL | SEQ ID NO: 51 (N3 VL mutant 2) |
| N3-8 | VH | EVQLLESGGGLVQPGGSLRLSCAASGFTF SSYDMSWVRQAPGKGLEWVSAISPYSGRI YYADSVKGRFTISRDNSKNTLYLQMNSLRA EDTAVYYCARMALDFDYWGQGTLVTVSS | SEQ ID NO: 45 (N3 VH mutant 6) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYYC SSFSDELgAYVFGGGTKLTVL | SEQ ID NO: 51 (N3 VL mutant 2) |
| N3-9 | VH | EVQLLESGGGLVQPGGSLRLSCAASGFTF SSYDMSWVRQAPGKGLEWVSAIGADGGP SYYADSVKGRFTISRDNSKNTLYLQMNSLR AEDTAVYYSARMALDFDYWGQGTLVTVSS | SEQ ID NO: 43 (N3 VH mutant 5) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYYC SSFSDELgAYVFGGGTKLTVL | SEQ ID NO: 51 (N3 VL mutant 2) |

In addition, ELISA was performed in the same manner as in the Example 2 in order to measure the affinity for the N-terminus of KRS to confirm whether the affinity for the N-terminus of KRS was increased.

Specifically, the N-terminal portion (1-72) of KRS was coated in a 96-well EIA/RIA plate (COSTAR Corning) at 25° C. for 1 hour, and then the plate was washed three times with PBS for 10 minutes. Then, the plate was incubated with 4% BSA PBS for 1 hour, and then washed 3 times with PBS for 10 minutes. Then, the IgG-type KRS N-terminal target antibodies N3-1, N3-6, N3-7, N3-8, and N3-9 were treated and incubated and the plate was washed three times for 10 minutes with 0.1% PBST. An anti-human antibody conjugated with HRP was used, and it was reacted with TMB (3,3',5,5'-Tetramethylbenzidine) and absorbance was measured at 450 nm and the binding was quantified.

Figure 7:
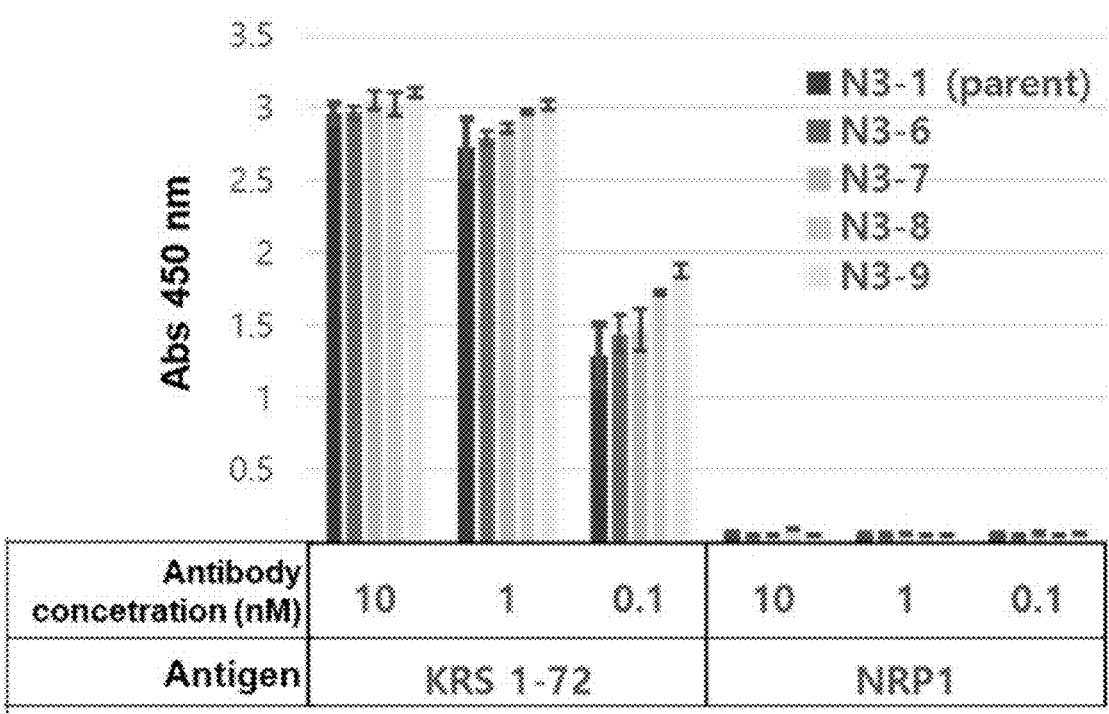
FIG. 7 shows the ELISA results for measuring the affinity of the N3-1 antibody, N3-6 antibody, N3-7 antibody, N3-8 antibody and N3-9 antibody for the N-terminus of KRS.

As a result, as shown in FIG. 7, it was confirmed that the affinity of the mutant antibodies N3-6, N3-7, N3-8, and N3-9 was increased compared to N3-1 antibody. All the antibodies did not interact with NRP1-b1b2, which was used as a negative control.

Example 6: Comparison of Affinity Between the N3-1 Antibody and the N3-6, N3-7, N3-8, N3-9 Antibodies

6-1. Comparison of Antibody Binding to KRS

Using KRS epitope peptide F4 (EPKLSKNELKRRL-KAEKKVAEKEAKQKE: SEQ ID NO: 117) as an antigen epitope, the binding ability of N3 antibody, N3-6 antibody, N3-7 antibody, N3-8 antibody, and N3-9 antibody was analyzed via Surface Plasmon Resonance (SPR). SPR experiment was carried out in the same manner as in the Example 3-2. The epitope was diluted in PBS solution and diluted 2-fold in the range of 15.7 nM-4000 nM, and allowed to flow for 90 seconds. Thereafter, PBS was flowed for 2400 seconds. The obtained data was analyzed with Biacore T200 Evaluation software v2.0 (GE Healthcare).

Figure 8:
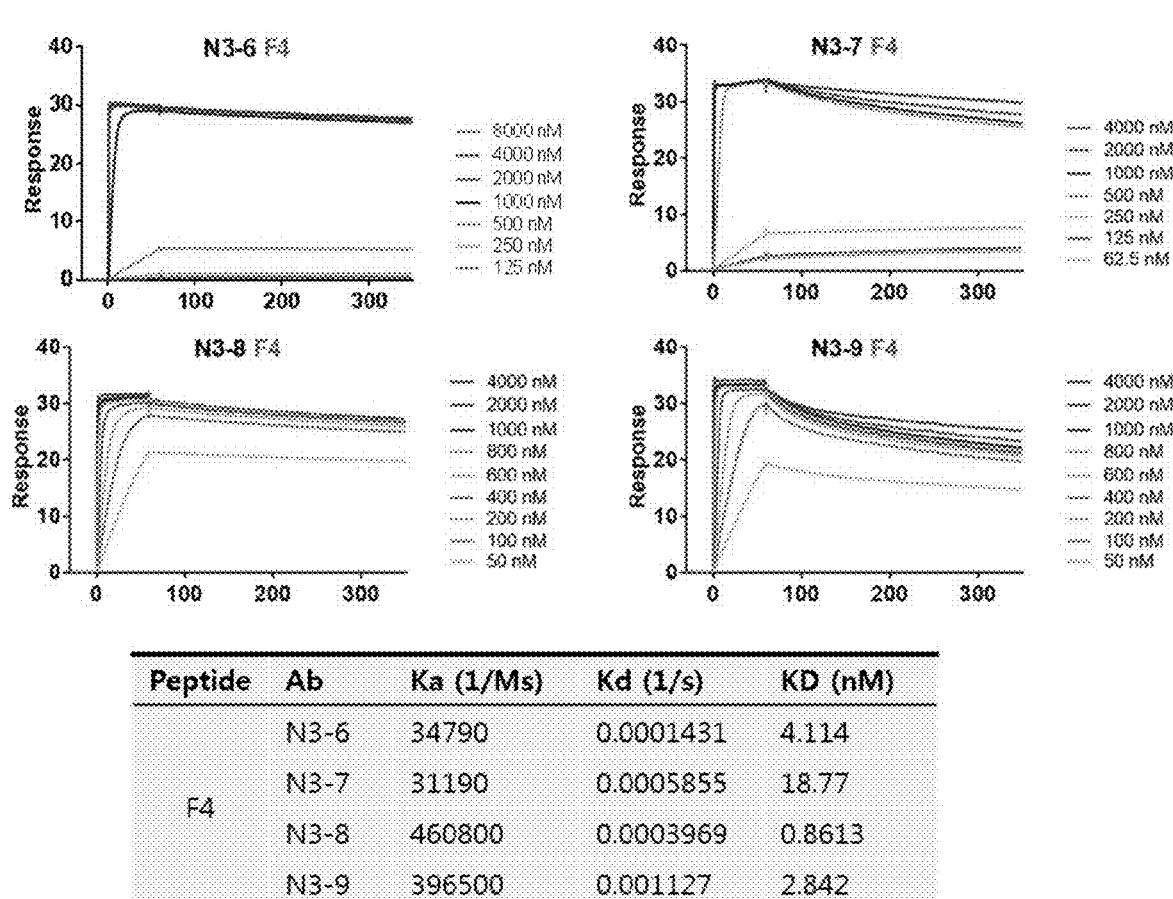
FIG. 8 shows the results of comparing the affinity of N3-6 antibody, N3-7 antibody, N3-8 antibody and N3-9 antibody for KRS by the surface plasmon resonance (SPR) method.

As a result, as shown in FIG. 8, the KD of the N3-8 antibody was exhibited to be excellent, the KD of the N3-9 and N3-6 antibodies were similar, and the KD value of the N3-7 antibody was the largest. The dissociation time of N3-6 antibody was longer than that of N3-7 and N3-9, and showed a sensorgram with longer binding.

Also, ELISA was performed to identify residues that are important for antibody-epitope binding, using peptides in which the single amino acids of KRS epitope peptide F4 (SEQ ID NO: 117) were substituted with alanine (A), respectively. As a result, the residues in KRS epitope peptide F4 that are important in binding to each antibody was able to be identified.

6-2. Cell Migration Inhibitory Effect of Antibody

Experiments were performed in the same manner as in Example 3-1. N3-6, N3-7, N3-8, N3-9 antibodies prepared in the above Example were converted to IgG by a conventional method. The following experiment was performed using the converted IgG antibodies.

Cells were put into the upper chamber at a concentration of $1 \times 10^5$, and then N3 IgG was treated at 100 nM, and N3-1, N3-6, N3-7, N3-8 and N3-9 IgG, and human mock IgG (control) were each treated in the chamber at 10 nM and cultured for 24 hours. The non-migrating cells present above the membrane were removed with a cotton swab.

Then, the membrane was washed twice with PBS and treated with 70% MeOH (in PBS) for 30 minutes. After washing twice with PBS, hematoxylin solution was treated for 30 minutes. Then, after washing the chamber with DW, the membrane in the chamber was mounted on a slide glass and observed.

Figure 9:
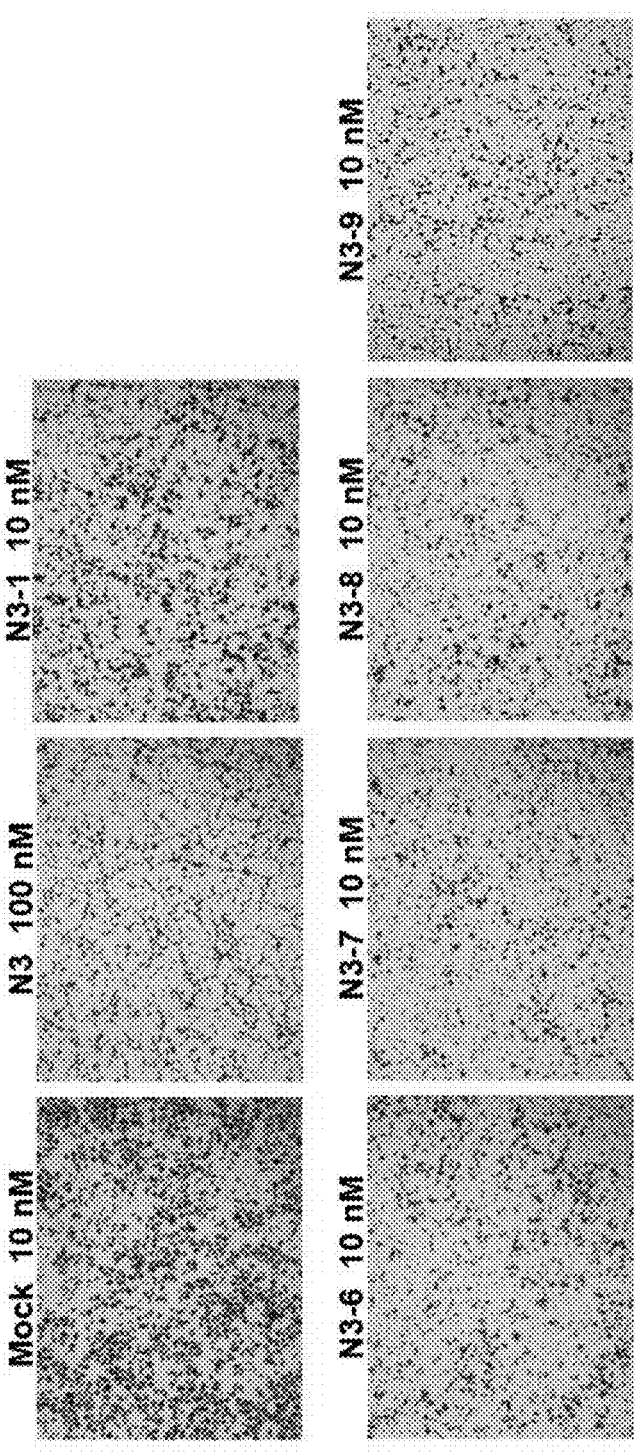
FIG. 9 shows the results of confirming the cell migration inhibitory effect of the N3 antibody, N3-1 antibody, N3-6 antibody, N3-7 antibody, N3-8 antibody, and N3-9 antibody.

As a result, as shown in FIG. 9, it was confirmed that N3-6, N3-7, N3-8, and N3-9 antibodies significantly inhibited cell migration compared to the N3-1 antibody. In addition, there was no significant difference in the effect of inhibiting cell migration among N3-6, N3-7, N3-8, and N3-9 antibodies.

Example 7: Sequence Refinement of N3-8 Antibody 7-1. Mutation Production of N3-8 Antibody Sequence In the above example, it was confirmed that N3-8 antibody has the best affinity. Thus, experiments were conducted as follows to confirm physical properties such as productivity and stability of N3-8 antibody.

A mutation was induced in the sequence expected to affect stability in the N3-8 antibody sequence. As a result, two additional heavy chain sequences in which mutations were introduced into the heavy chain sequence (HC) of N3-8 antibody were obtained. In addition, it was possible to obtain three additional light chain sequences into which the mutation was introduced. Accordingly, 7 kinds of antibody sequences (N3-8 derivatives) in which the sequence of N3-8 was changed are shown in Tables 5 and 6 below.

TABLE 5

|  | Heavy | | | Light | | |
|---|---|---|---|---|---|---|
|  | CDR H1 | CDR H2 | CDR H3 | CDR L1 | CDR L2 | CDR L3 |
| N3-8-1 | SYDMS (SEQ ID NO: 1) | AISPYSGR IYYADSVK G (SEQ ID NO: 21) | MALDFDY (SEQ ID NO: 5) | TGSSSNI GSNYVT (SEQ ID NO: 7) | DNSNRPS (SEQ ID NO: 9) | SSFSDELG AYV (SEQ ID NO: 15) |
| N3-8-2 | SYDMS (SEQ ID NO: 1) | AISPYSGR IYYADSVK G (SEQ ID NO: 21) | MALDFDY (SEQ ID NO: 5) | TGSSSNI GSNYVT (SEQ ID NO: 7) | SNNQRPS (SEQ ID NO: 27) | SSFSDELG AYV (SEQ ID NO: 15) |
| N3-8-3 | SYDMS (SEQ ID NO: 1) | AISPYSGR IYYADSVK G (SEQ ID NO: 21) | MALDFDY (SEQ ID NO: 5) | TGSSSNI GSNYVT (SEQ ID NO: 7) | RNNQRPS (SEQ ID NO: 29) | SSFSDELG AYV (SEQ ID NO: 15) |
| N3-8-4 | SYDMS (SEQ ID NO: 1) | AISPYSGR IYYADSVK G (SEQ ID NO: 21) | LALDFDY (SEQ ID NO: 25) | TGSSSNI GSNYVT (SEQ ID NO: 7) | DNSNRPS (SEQ ID NO: 9) | SSFSDELG AYV (SEQ ID NO: 15) |
| N3-8-5 | SYDMS (SEQ ID NO: 1) | AISPYSGR IYYADSVK G (SEQ ID NO: 21) | LALDFDY GSNYVT (SEQ ID NO: 25) | TGSSSNI (SEQ ID NO: 7) | SNNQRPS (SEQ ID NO: 27) | SSFSDELG AYV (SEQ ID NO: 15) |
| N3-8-6 | SYDMS (SEQ ID NO: 1) | AISPYSGR IYYADSVK G (SEQ ID NO: 21) | LALDFDY (SEQ ID NO: 25) | TGSSSNI GSNYVT (SEQ ID NO: 7) | RNNQRPS (SEQ ID NO: 29) | SSFSDELG AYV (SEQ ID NO: 15) |
| N3-8-7 | SYDMS (SEQ ID NO: 1) | AISPYSGR IYYADSVK G (SEQ ID NO: 21) | MALDFDY (SEQ ID NO: 5) | TGSSSNI GSNYVT (SEQ ID NO: 7) | DNSNRPS (SEQ ID NO: 9) | SSFSDELG AYV (SEQ ID NO: 15) |

TABLE 6

| | | Sequence | SEQ ID NO: (Sequence name) |
|---|---|---|---|
| N3-8-1 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARMALDFDYWGQGTLVTVSS | SEQ ID NO: 45 (N3 VH mutant 6) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYY CSSFSDELGAYVFGGGTKLTVL | SEQ ID NO: 51 (N3 VL mutant 2) |
| N3-8-2 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARMALDFDYWGQGTLVTVSS | SEQ ID NO: 45 (N3 VH mutant 6) |
| | VL | QSVLTQPPSASGTPGQRVTISCTGSSSNIG SNYVTWYQQLPGTAPKLLIYSNNQRPSGV PDRFSGSKSGTSASLAISGLQSEDEADYY CSSFSDELGAYVFGGGTKLTVL | SEQ ID NO: 53 (N3 VL mutant 3) |
| N3-8-3 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARMALDFDYWGQGTLVTVSS | SEQ ID NO: 45 (N3 VH mutant 6) |
| | VL | QSVLTQPPSASGTPGQRVTISCTGSSSNIG SNYVTWYQQLPGTAPKLLIYRNNQRPSGV PDRFSGSKSGTSASLAISGLQSEDEADYY CSSFSDELGAYVFGGGTKLTVL | SEQ ID NO: 55 (N3 VL mutant 4) |
| N3-8-4 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARLALDFDYWGQGTLVTVSS | SEQ ID NO: 47 (N3 VH mutant 7) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYY CSSFSDELGAYVFGGGTKLTVL | SEQ ID NO: 51 (N3 VL mutant 2) |
| N3-8-5 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARLALDFDYWGQGTLVTVSS | SEQ ID NO: 47 (N3 VH mutant 7) |
| | VL | QSVLTQPPSASGTPGQRVTISCTGSSSNIG SNYVTWYQQLPGTAPKLLIYSNNQRPSGV PDRFSGSKSGTSASLAISGLQSEDEADYY CSSFSDELGAYVFGGGTKLTVL | SEQ ID NO: 53 (N3 VL mutant 3) |
| N3-8-6 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYCARLALDFDYWGQGTLVTVSS | SEQ ID NO: 47 (N3 VH mutant 7) |
| | VL | QSVLTQPPSASGTPGQRVTISCTGSSSNIG SNYVTWYQQLPGTAPKLLIYRNNQRPSGV PDRFSGSKSGTSASLAISGLQSEDEADYY CSSFSDELGAYVFGGGTKLTVL | SEQ ID NO: 55 (N3 VL mutant 4) |
| N3-8-7 | VH | EVQLLESGGGLVQPGGSLRLSCAASGFTF SSYDMSWVRQAPGKGLEWVSAISPYSGR IYYADSVKGRFTISRDNSKNTLYLQMNSLR AEDTAVYYSARMALDFDYWGQGTLVTVSS | SEQ ID NO: 41 (N3 VH mutant 4) |
| | VL | QSVLTQPPSASGTPGQRVTISCTGSSSNIG SNYVTWYQQLPGTAPKLLIYDNSNRPSGV PDRFSGSKSGTSASLAISGLQSEDEADYY CSSFSDELGAYVFGGGTKLTVL | SEQ ID NO: 51 (N3 VL mutant 2) |

7-2. Measurement of Productivity and Stability of N3-8 Antibody Derivatives And Tm Measurement The vector expressing the N3-8 antibody derivative obtained in Example 7-1 was expressed and purified using transient transfection.

To HEK293-F cells (Invitrogen) suspended in serum-free FreeStyle 293 expression medium (Invitrogen) in a shake flask, the plasmid and polyethylenimine (Polyethylenimine, Polyscience) were transfected. During transfection into a 200 ml shake flask, HEK293-F cells were seeded in 100 ml of medium at a density of $2\times10^6$ cells/ml and cultured at 150 rpm and 37° C. with 8% $CO_2$.

To produce each monoclonal antibody, suitable heavy and light chain plasmids were transfected into 10 ml FreeStyle 293 expression medium (Invitrogen) at a ratio of 1:1 or 1:2 of heavy chain: light chain DNA. When heavy chain: light chain DNA is used in a 1:1 ratio, 125 µg heavy chain and 125 µg light chain, a total of 250 µg (2.5 µg/ml) DNA is mixed with 10 ml of medium containing PEI 750 µg (7.5 µg/ml) at room temperature. The reaction was carried out for 10 minutes. In the case of the ratio 1:2, the concentration of the light chain DNA was doubled. Thereafter, the mixed medium was treated with cells previously aliquoted with 100 ml, and incubated at 150 rpm and 37° C., with 8% $CO_2$ for 4 hours, and then additional 100 ml of FreeStyle 293 expression medium was added and cultured for 6 days.

Then, the cell culture solution was transferred to 50 ml tubes and centrifuged for 5 minutes at 3000 rpm. Protein was then purified from the collected cell culture supernatant. The antibody was applied to a Protein A Sepharose column, and then washed with PBS (pH 7.4). After eluting the antibody at pH 3.0 with 0.1 M glycine buffer, the sample was immediately neutralized with 1 M Tris buffer. The eluted antibody fraction was concentrated by exchanging buffer with PBS (pH 7.4) through a dialysis method. The purified protein was quantified based on absorbance measurement and absorption coefficient at a wavelength of 280 nm.

In addition, the thermal stability of the antibody was measured using 100 μl of the purified antibodies at a concentration of 1 mg/ml. Thermostability was investigated 4 times using protein thermal shift dye kit (Thermofisher) and Quant Studio 3 Real-time PCR equipment (Thermofisher).

As a result, as shown in Table 7 below, the yield of all the N3-8 antibody derivatives tested was improved or showed a high yield at a similar level of the N3-8 antibody. Further, as shown in Table 7, a Tm value was obtained. The thermal transition was observed to be 1-2 depending on the antibody, but the Tm value was increased in all N3-8 antibody derivatives.

Through this, it was confirmed that the N3-8 antibody derivatives had higher yield and their thermal stability was improved compared to that of N3-8 antibody.

TABLE 7

| Antibody | Yield (mg/L) | | Thermal stability | |
| --- | --- | --- | --- | --- |
| | (1:1) | (1:2) | Tm1 | Tm2 |
| N3-8 | 69.9 | 104.61 | 67.37 | — |
| N3-8-1 | 87.13 | 109.9 | 69.94 | — |
| N3-8-2 | 96.76 | 109.68 | 72.41 | — |
| N3-8-3 | 93.44 | 93.53 | 71.02 | 76.31 |
| N3-8-4 | 86.14 | 89.23 | 70.31 | — |
| N3-8-5 | 84.31 | 107.37 | 72.9 | — |
| N3-8-6 | 105.95 | 92.9 | 71.0 | 76.97 |

Table 8 shows the heavy chain (HC) and light chain (LC) sequences of the entire IgG antibodies used in the above-described examples.

TABLE 8

| | | Amino acid sequence | DNA sequence |
| --- | --- | --- | --- |
| N3 | HC | SEQ ID NO: 89 | SEQ ID NO: 90 |
| | LC | SEQ ID NO: 91 | SEQ ID NO: 92 |
| N3-1 | HC | SEQ ID NO: 89 | SEQ ID NO: 90 |
| | LC | SEQ ID NO: 107 | SEQ ID NO: 108 |
| N3-3 | HC | SEQ ID NO: 89 | SEQ ID NO: 90 |
| | LC | SEQ ID NO: 109 | SEQ ID NO: 110 |
| N3-4 | HC | SEQ ID NO: 93 | SEQ ID NO: 94 |
| | LC | SEQ ID NO: 107 | SEQ ID NO: 108 |
| N3-5 | HC | SEQ ID NO: 93 | SEQ ID NO: 94 |
| | LC | SEQ ID NO: 109 | SEQ ID NO: 110 |
| N3-6 | HC | SEQ ID NO: 95 | SEQ ID NO: 96 |
| | LC | SEQ ID NO: 109 | SEQ ID NO: 110 |
| N3-7 | HC | SEQ ID NO: 97 | SEQ ID NO: 98 |
| | LC | SEQ ID NO: 109 | SEQ ID NO: 110 |
| N3-8 | HC | SEQ ID NO: 103 | SEQ ID NO: 104 |
| | LC | SEQ ID NO: 109 | SEQ ID NO: 110 |

TABLE 8-continued

| | | Amino acid sequence | DNA sequence |
| --- | --- | --- | --- |
| N3-9 | HC | SEQ ID NO: 101 | SEQ ID NO: 102 |
| | LC | SEQ ID NO: 109 | SEQ ID NO: 110 |
| N3-8-1 | HC | SEQ ID NO: 103 | SEQ ID NO: 104 |
| | LC | SEQ ID NO: 111 | SEQ ID NO: 112 |
| N3-8-2 | HC | SEQ ID NO: 103 | SEQ ID NO: 104 |
| | LC | SEQ ID NO: 113 | SEQ ID NO: 114 |
| N3-8-3 | HC | SEQ ID NO: 103 | SEQ ID NO: 104 |
| | LC | SEQ ID NO: 115 | SEQ ID NO: 116 |
| N3-8-4 | HC | SEQ ID NO: 105 | SEQ ID NO: 106 |
| | LC | SEQ ID NO: 111 | SEQ ID NO: 112 |
| N3-8-5 | HC | SEQ ID NO: 105 | SEQ ID NO: 106 |
| | LC | SEQ ID NO: 113 | SEQ ID NO: 114 |
| N3-8-6 | HC | SEQ ID NO: 105 | SEQ ID NO: 106 |
| | LC | SEQ ID NO: 115 | SEQ ID NO: 116 |
| N3-8-7 | HC | SEQ ID NO: 99 | SEQ ID NO: 100 |
| | LC | SEQ ID NO: 111 | SEQ ID NO: 112 |

7-3. Affinity Comparison of N3-8-1 and N3-8-4 Antibodies

As described in Example 6, the KRS epitope peptide F4 (EPKLSKNELKRRLKAEKKVAEKEAKQKE: SEQ ID NO: 117) was used as an antigen epitope, and the binding strength to N3-8-1 and N3-8-4 antibodies was analyzed via Surface Plasmon Resonance (SPR).

The SPR experiment was carried out in the same manner as in the Example 3-2, and epitope was diluted in PBS solution, diluted twice in a range of 15.7 nM-4000 nM, and flowed for 90 seconds. After that, PBS was flowed for 2400 seconds. The obtained data was analyzed with Biacore T200 Evaluation software v2.0 (GE Healthcare).

As a result, as shown in Table 9 below, it was found that the KD of the N3-8-1 antibody was the most excellent.

TABLE 9

| Peptide | Ab | Ka (1/Ms) | Kd (1/s) | KD (nM) |
| --- | --- | --- | --- | --- |
| F4 | N3-8-1 | 267900 | 0.000215 | 0.8025 |
| | N3-8-4 | 89480 | 0.00090 | 10.06 |

Example 8: Confirmation of Mechanism of Antibody

After conjugation of a fluorescent probe with antibody (Ab) and treatment on 4T1 breast cancer cells, it was confirmed that the anti-KRS antibodies (N3, N3-8) were endocytosed.

Anti-KRS antibodies (N3, N3-8) labeled with Alexa fluor 488 (Thermofisher) fluorescent probe and 1 μM of Mock IgG (Thermofisher) as a control were treated to the cells, and the localization of antibodies was monitored after 4 hours. At this time, Lysotracker (Thermofisher) was used as a lysosome marker and DAPI was used for nucleus staining. Unlike Mock IgG, N3 and N3-8 antibodies were present within the cells at 4 hours.

Figure 10:
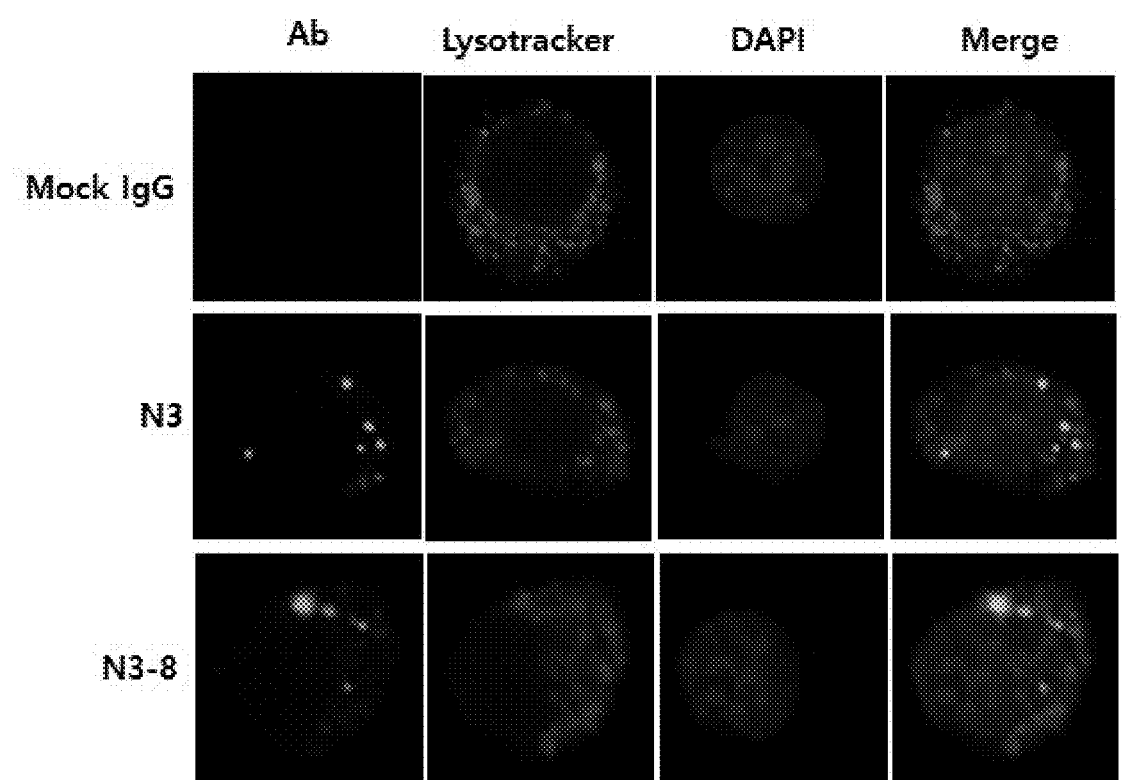
FIG. 10 shows the results of confirming the endocytosis of the N3 antibody and the N3-8 antibody in breast cancer cells by the IHC (immunohistochemistry) method.

As a result, as shown in FIG. 10, it was confirmed that the anti-KRS antibody recognizes the cell membrane KRS and is endocytosed rapidly, thereby lowering the cell membrane KRS level.

Example 9: Sequence and Purification of Antibody from which ADCC/CDC Function has been Removed 9-1. Mutation Introduction into Antibody Sequence to Remove ADCC/CDC Function In order to remove the ADCC/CDC function from the antibody, an experiment was performed as follows. In each of the above antibody sequences, mutations were introduced into the portion expected to function for ADCC/CDC in a constant region of the IgG1 heavy chain. Five additional heavy chain sequences where mutations were introduced were obtained. In addition, IgG4 heavy chain sequence and additional one into which a mutation was introduced were generated. Accordingly, the mutant antibody sequences from which the ADCC/CDC function has been removed from each antibody are shown in Table 10, respectively.

TABLE 10

| | | | Amino acid sequence | DNA sequence |
|---|---|---|---|---|
| N3 | HC | IgG1 | SEQ ID NO: 89 | SEQ ID NO: 90 |
| | | IgG1 mutant TA | SEQ ID NO: 140 | SEQ ID NO: 141 |
| | | IgG1 mutant LALA | SEQ ID NO: 142 | SEQ ID NO: 143 |
| | | IgG1 mutant LALATA | SEQ ID NO: 144 | SEQ ID NO: 145 |
| | | IgG1 mutant LALAPG | SEQ ID NO: 146 | SEQ ID NO: 147 |
| | | IgG1 mutant LALAPGTA | SEQ ID NO: 148 | SEQ ID NO: 149 |
| | | IgG4 | SEQ ID NO: 150 | SEQ ID NO: 151 |
| | | IgG4 mutant TA | SEQ ID NO: 152 | SEQ ID NO: 153 |
| | LC | | SEQ ID NO: 91 | SEQ ID NO: 92 |
| N3-1 | HC | IgG1 | SEQ ID NO: 89 | SEQ ID NO: 90 |
| | | IgG1 mutant TA | SEQ ID NO: 140 | SEQ ID NO: 141 |
| | | IgG1 mutant LALA | SEQ ID NO: 142 | SEQ ID NO: 143 |
| | | IgG1 mutant LALATA | SEQ ID NO: 144 | SEQ ID NO: 145 |
| | | IgG1 mutant LALAPG | SEQ ID NO: 146 | SEQ ID NO: 147 |
| | | IgG1 mutant LALAPGTA | SEQ ID NO: 148 | SEQ ID NO: 149 |
| | | IgG4 | SEQ ID NO: 150 | SEQ ID NO: 151 |
| | | IgG4 mutant TA | SEQ ID NO: 152 | SEQ ID NO: 153 |
| | LC | | SEQ ID NO: 107 | SEQ ID NO: 108 |
| N3-3 | HC | IgG1 | SEQ ID NO: 89 | SEQ ID NO: 90 |
| | | IgG1 mutant TA | SEQ ID NO: 140 | SEQ ID NO: 141 |
| | | IgG1 mutant LALA | SEQ ID NO: 142 | SEQ ID NO: 143 |
| | | IgG1 mutant LALATA | SEQ ID NO: 144 | SEQ ID NO: 145 |
| | | IgG1 mutant LALAPG | SEQ ID NO: 146 | SEQ ID NO: 147 |
| | | IgG1 mutant LALAPGTA | SEQ ID NO: 148 | SEQ ID NO: 149 |
| | | IgG4 | SEQ ID NO: 150 | SEQ ID NO: 151 |
| | | IgG4 mutant TA | SEQ ID NO: 152 | SEQ ID NO: 153 |
| | LC | | SEQ ID NO: 109 | SEQ ID NO: 110 |
| N3-4 | HC | IgG1 | SEQ ID NO: 93 | SEQ ID NO: 94 |
| | | IgG1 mutant TA | SEQ ID NO: 154 | SEQ ID NO: 155 |
| | | IgG1 mutant LALA | SEQ ID NO: 156 | SEQ ID NO: 157 |
| | | IgG1 mutant LALATA | SEQ ID NO: 158 | SEQ ID NO: 159 |
| | | IgG1 mutant LALAPG | SEQ ID NO: 160 | SEQ ID NO: 161 |
| | | IgG1 mutant LALAPGTA | SEQ ID NO: 162 | SEQ ID NO: 163 |
| | | IgG4 | SEQ ID NO: 164 | SEQ ID NO: 165 |
| | | IgG4 mutant TA | SEQ ID NO: 166 | SEQ ID NO: 167 |
| | LC | | SEQ ID NO: 107 | SEQ ID NO: 108 |
| N3-5 | HC | IgG1 | SEQ ID NO: 93 | SEQ ID NO: 94 |
| | | IgG1 mutant TA | SEQ ID NO: 154 | SEQ ID NO: 155 |
| | | IgG1 mutant LALA | SEQ ID NO: 156 | SEQ ID NO: 157 |
| | | IgG1 mutant LALATA | SEQ ID NO: 158 | SEQ ID NO: 159 |
| | | IgG1 mutant LALAPG | SEQ ID NO: 160 | SEQ ID NO: 161 |
| | | IgG1 mutant LALAPGTA | SEQ ID NO: 162 | SEQ ID NO: 163 |
| | | IgG4 | SEQ ID NO: 164 | SEQ ID NO: 165 |
| | | IgG4 mutant TA | SEQ ID NO: 166 | SEQ ID NO: 167 |
| | LC | | SEQ ID NO: 109 | SEQ ID NO: 110 |
| N3-6 | HC | IgG1 | SEQ ID NO: 95 | SEQ ID NO: 96 |
| | | IgG1 mutant TA | SEQ ID NO: 168 | SEQ ID NO: 169 |
| | | IgG1 mutant LALA | SEQ ID NO: 170 | SEQ ID NO: 171 |
| | | IgG1 mutant LALATA | SEQ ID NO: 172 | SEQ ID NO: 173 |
| | | IgG1 mutant LALAPG | SEQ ID NO: 174 | SEQ ID NO: 175 |
| | | IgG1 mutant LALAPGTA | SEQ ID NO: 176 | SEQ ID NO: 177 |
| | | IgG4 | SEQ ID NO: 178 | SEQ ID NO: 179 |
| | | IgG4 mutant TA | SEQ ID NO: 180 | SEQ ID NO: 181 |
| | LC | | SEQ ID NO: 109 | SEQ ID NO: 110 |
| N3-7 | HC | IgG1 | SEQ ID NO: 97 | SEQ ID NO: 98 |
| | | IgG1 mutant TA | SEQ ID NO: 182 | SEQ ID NO: 183 |
| | | IgG1 mutant LALA | SEQ ID NO: 184 | SEQ ID NO: 185 |
| | | IgG1 mutant LALATA | SEQ ID NO: 186 | SEQ ID NO: 187 |
| | | IgG1 mutant LALAPG | SEQ ID NO: 188 | SEQ ID NO: 189 |
| | | IgG1 mutant LALAPGTA | SEQ ID NO: 190 | SEQ ID NO: 191 |
| | | IgG4 | SEQ ID NO: 192 | SEQ ID NO: 193 |
| | | IgG4 mutant TA | SEQ ID NO: 194 | SEQ ID NO: 195 |
| | LC | | SEQ ID NO: 109 | SEQ ID NO: 110 |
| N3-8 | HC | IgG1 | SEQ ID NO: 103 | SEQ ID NO: 104 |
| | | IgG1 mutant TA | SEQ ID NO: 224 | SEQ ID NO: 225 |
| | | IgG1 mutant LALA | SEQ ID NO: 226 | SEQ ID NO: 227 |

TABLE 10-continued

| | | | Amino acid sequence | DNA sequence |
|---|---|---|---|---|
| | | IgG1 mutant LALATA | SEQ ID NO: 228 | SEQ ID NO: 229 |
| | | IgG1 mutant LALAPG | SEQ ID NO: 230 | SEQ ID NO: 231 |
| | | IgG1 mutant LALAPGTA | SEQ ID NO: 232 | SEQ ID NO: 233 |
| | | IgG4 | SEQ ID NO: 234 | SEQ ID NO: 235 |
| | | IgG4 mutant TA | SEQ ID NO: 236 | SEQ ID NO: 237 |
| | LC | | SEQ ID NO: 109 | SEQ ID NO: 110 |
| N3-9 | HC | IgG1 | SEQ ID NO: 101 | SEQ ID NO: 102 |
| | | IgG1 mutant TA | SEQ ID NO: 210 | SEQ ID NO: 211 |
| | | IgG1 mutant LALA | SEQ ID NO: 212 | SEQ ID NO: 213 |
| | | IgG1 mutant LALATA | SEQ ID NO: 214 | SEQ ID NO: 215 |
| | | IgG1 mutant LALAPG | SEQ ID NO: 216 | SEQ ID NO: 217 |
| | | IgG1 mutant LALAPGTA | SEQ ID NO: 218 | SEQ ID NO: 219 |
| | | IgG4 | SEQ ID NO: 220 | SEQ ID NO: 221 |
| | | IgG4 mutant TA | SEQ ID NO: 222 | SEQ ID NO: 223 |
| | LC | | SEQ ID NO: 109 | SEQ ID NO: 110 |
| N3-8-1 | HC | IgG1 | SEQ ID NO: 103 | SEQ ID NO: 104 |
| | | IgG1 mutant TA | SEQ ID NO: 224 | SEQ ID NO: 225 |
| | | IgG1 mutant LALA | SEQ ID NO: 226 | SEQ ID NO: 227 |
| | | IgG1 mutant LALATA | SEQ ID NO: 228 | SEQ ID NO: 229 |
| | | IgG1 mutant LALAPG | SEQ ID NO: 230 | SEQ ID NO: 231 |
| | | IgG1 mutant LALAPGTA | SEQ ID NO: 232 | SEQ ID NO: 233 |
| | | IgG4 | SEQ ID NO: 234 | SEQ ID NO: 235 |
| | | IgG4 mutant TA | SEQ ID NO: 236 | SEQ ID NO: 237 |
| | LC | | SEQ ID NO: 111 | SEQ ID NO: 112 |
| N3-8-2 | HC | IgG1 | SEQ ID NO: 103 | SEQ ID NO: 104 |
| | | IgG1 mutant TA | SEQ ID NO: 224 | SEQ ID NO: 225 |
| | | IgG1 mutant LALA | SEQ ID NO: 226 | SEQ ID NO: 227 |
| | | IgG1 mutant LALATA | SEQ ID NO: 228 | SEQ ID NO: 229 |
| | | IgG1 mutant LALAPG | SEQ ID NO: 230 | SEQ ID NO: 231 |
| | | IgG1 mutant LALAPGTA | SEQ ID NO: 232 | SEQ ID NO: 233 |
| | | IgG4 | SEQ ID NO: 234 | SEQ ID NO: 235 |
| | | IgG4 mutant TA | SEQ ID NO: 236 | SEQ ID NO: 237 |
| | LC | | SEQ ID NO: 113 | SEQ ID NO: 114 |
| N3-8-3 | HC | IgG1 | SEQ ID NO: 103 | SEQ ID NO: 104 |
| | | IgG1 mutant TA | SEQ ID NO: 224 | SEQ ID NO: 225 |
| | | IgG1 mutant LALA | SEQ ID NO: 226 | SEQ ID NO: 227 |
| | | IgG1 mutant LALATA | SEQ ID NO: 228 | SEQ ID NO: 229 |
| | | IgG1 mutant LALAPG | SEQ ID NO: 230 | SEQ ID NO: 231 |
| | | IgG1 mutant LALAPGTA | SEQ ID NO: 232 | SEQ ID NO: 233 |
| | | IgG4 | SEQ ID NO: 234 | SEQ ID NO: 235 |
| | | IgG4 mutant TA | SEQ ID NO: 236 | SEQ ID NO: 237 |
| | LC | | SEQ ID NO: 115 | SEQ ID NO: 116 |
| N3-8-4 | HC | IgG1 | SEQ ID NO: 105 | SEQ ID NO: 106 |
| | | IgG1 mutant TA | SEQ ID NO: 238 | SEQ ID NO: 239 |
| | | IgG1 mutant LALA | SEQ ID NO: 240 | SEQ ID NO: 241 |
| | | IgG1 mutant LALATA | SEQ ID NO: 242 | SEQ ID NO: 243 |
| | | IgG1 mutant LALAPG | SEQ ID NO: 244 | SEQ ID NO: 245 |
| | | IgG1 mutant LALAPGTA | SEQ ID NO: 246 | SEQ ID NO: 247 |
| | | IgG4 | SEQ ID NO: 248 | SEQ ID NO: 249 |
| | | IgG4 mutant TA | SEQ ID NO: 250 | SEQ ID NO: 251 |
| | LC | | SEQ ID NO: 111 | SEQ ID NO: 112 |
| N3-8-5 | HC | IgG1 | SEQ ID NO: 105 | SEQ ID NO: 106 |
| | | IgG1 mutant TA | SEQ ID NO: 238 | SEQ ID NO: 239 |
| | | IgG1 mutant LALA | SEQ ID NO: 240 | SEQ ID NO: 241 |
| | | IgG1 mutant LALATA | SEQ ID NO: 242 | SEQ ID NO: 243 |
| | | IgG1 mutant LALAPG | SEQ ID NO: 244 | SEQ ID NO: 245 |
| | | IgG1 mutant LALAPGTA | SEQ ID NO: 246 | SEQ ID NO: 247 |
| | | IgG4 | SEQ ID NO: 248 | SEQ ID NO: 249 |
| | | IgG4 mutant TA | SEQ ID NO: 250 | SEQ ID NO: 251 |
| | LC | | SEQ ID NO: 113 | SEQ ID NO: 114 |
| N3-8-6 | HC | IgG1 | SEQ ID NO: 105 | SEQ ID NO: 106 |
| | | IgG1 mutant TA | SEQ ID NO: 238 | SEQ ID NO: 239 |
| | | IgG1 mutant LALA | SEQ ID NO: 240 | SEQ ID NO: 241 |
| | | IgG1 mutant LALATA | SEQ ID NO: 242 | SEQ ID NO: 243 |
| | | IgG1 mutant LALAPG | SEQ ID NO: 244 | SEQ ID NO: 245 |
| | | IgG1 mutant LALAPGTA | SEQ ID NO: 246 | SEQ ID NO: 247 |
| | | IgG4 | SEQ ID NO: 248 | SEQ ID NO: 249 |
| | | IgG4 mutant TA | SEQ ID NO: 250 | SEQ ID NO: 251 |
| | LC | | SEQ ID NO: 115 | SEQ ID NO: 116 |
| N3-8-7 | HC | IgG1 | SEQ ID NO: 99 | SEQ ID NO: 100 |
| | | IgG1 mutant TA | SEQ ID NO: 196 | SEQ ID NO: 197 |
| | | IgG1 mutant LALA | SEQ ID NO: 198 | SEQ ID NO: 199 |
| | | IgG1 mutant LALATA | SEQ ID NO: 200 | SEQ ID NO: 201 |
| | | IgG1 mutant LALAPG | SEQ ID NO: 202 | SEQ ID NO: 203 |

TABLE 10-continued

|  | Amino acid sequence | DNA sequence |
|---|---|---|
| IgG1 mutant LALAPGTA | SEQ ID NO: 204 | SEQ ID NO: 205 |
| IgG4 | SEQ ID NO: 206 | SEQ ID NO: 207 |
| IgG4 mutant TA | SEQ ID NO: 208 | SEQ ID NO: 209 |
| LC | SEQ ID NO: 111 | SEQ ID NO: 112 |

9-2. Purification of Mutant Antibodies with ADCC/CDC Function Removed

The vector expressing the mutant N3-8-1 antibody among the antibodies from which the ADCC/CDC function had been removed as described in the Example 9-1 was transiently transfected into cells to express and purify the protein.

HEK293-F cells (Invitrogen) were transfected in a shake flask according to the method described in the Example 7-2 above. Then, HEK293-F cells were seeded in a medium at a density of 2×10 6 cells/ml, and cultured at 150 rpm, 8% $CO_2$, and 37° C.

In order to produce each monoclonal antibody, suitable heavy and light chain plasmids were transfected into 10 ml FreeStyle 293 expression medium (Invitrogen) at a ratio of 1:1 or 1:2 of heavy chain: light chain DNA. In the case of 1:1, the heavy chain 125 μg and the light chain 125 μg, a total of 250 μg (2.5 μg/ml), were mixed with 10 ml medium containing 750 μg of PEI (7.5 μg/ml) and reacted at room temperature for 10 minutes. In the case of 1:2, the concentration of the light chain DNA was doubled. Thereafter, the reacted mixed medium was put into 100 ml of the cells and incubated for 4 hours at 150 rpm, 8% $CO_2$, and 37° C., and the additional 100 ml of FreeStyle 293 expression medium was added and cultured for 6 days.

Then, the cell culture solution was transferred to 50 ml tubes and centrifuged at 3000 rpm for 5 minutes. Subsequently, the protein was purified from the collected cell culture supernatant. The antibody was applied to a Protein A Sepharose column and washed with PBS (pH 7.4). After eluting the antibody at pH 3.0 using 0.1 M glycine buffer, the sample was immediately neutralized using 1 M Tris buffer. The eluted antibody fraction was concentrated by exchanging the buffer with PBS (pH 7.4) through a dialysis method. The purified protein was quantified based on absorbance measurement and extinction coefficient at a wavelength of 280 nm.

The purity of the purified antibody was measured, and thermostability was investigated 4 times using a Quant Studio 3 Real-time PCR equipment (Thermofisher) and a protein thermal shift dye kit (Thermofisher).

As a result, as shown in Table 11 below, the yield of all tested N3-8-1 antibody mutants was similar to or higher than that of the wild type, of which LALAPGTA mutations were found to have the highest yield. In addition, all of the N3-8-1 antibody mutants showed high purity at a level similar to that of wild type antibody.

Through this, it was confirmed that the antibodies from which the ADCC/CDC function of N3-8-1 has been removed have similar or higher yields and have similar purity compared to the N3-8-1 antibody.

TABLE 11

|  | Antibody | Yield (mg/ml) | Purity (%) |
|---|---|---|---|
| N-3-8-1 | wild type | 78.72 | 99.47 |
|  | mutant LALA | 70.7 | 99.87 |

TABLE 11-continued

| Antibody | Yield (mg/ml) | Purity (%) |
|---|---|---|
| mutant LALAPG | 73.78 | 99.86 |
| mutant LALATA | 77.7 | 99.91 |
| mutant LALAPGTA | 146.37 | 99.9 |

Example 10: Efficacy Verification of KRS-N Term Specific Antibodies in Immune Cell Migration-Related In Vivo Disease Models_In Vivo Pulmonary Arterial Hypertension Models When treated with an antibody that specifically binds to the KRS-N terminal end, immune cell migration/invasion is inhibited due to internalization of KRS at the site of the cell membrane (through endocytosis, etc.), and as a result, it can be seen that it has the effect of reducing the cell membrane KRS level. Therefore, it is believed that the KRS N-term specific antibody of the present invention (typically N3 antibody) will have a therapeutic effect against diseases related to immune cell migration, which is further demonstrated through the examples described below.

Experiment Methods

1) Construction of Pulmonary Arterial Hypertension (PAH) Models and Administration of a Test Substance To induce PAH in 7-week-old SD rats (Oriental Bio), 60 mpk of MCT (monocrotaline) were subcutaneously injected. Thereafter, the rats were divided into four groups (tested with five animals in each group), and were administrated with 1mpk of Mock human IgG (Thermo Fisher Scientific, negative control), 1mpk of N3 IgG antibody, 10mpk of N3 IgG antibody, and 25 mpk of sildenafil (positive control) for 3 weeks. All antibodies were i.v. injected twice a week and sildenafil was orally administered every day.

2) Blood Flow and Blood Pressure Measurement

After three weeks, the rats were anesthetized with isoflurane, and blood flow and pressure were measured using an MPVS Cardiovascular Pressure and Volume system (model name: MPVS Ultra, manufacturer: Millar Instruments). The right ventricular end-systolic pressure (RVESP), right ventricular end-diastolic pressure, left ventricular end-systolic pressure, left ventricular end-diastolic pressure were measured using an exclusive catheter (Mikro-Tip rat pressure catheter, manufacturer: Millar Instruments). The cardiac output was measured using a perivascular blood flow probe (Transonic Flow probes, manufacturer: Millar Instruments), and experimental method thereof was performed by the same method as disclosed in the following literature: Pacher P, Nagayama T, Mukhopadhyay P, Batkai S, Kass DA. Measurement of cardiac function using pressure-volume conductance catheter technique in mice and rats. Nat Protoc 2008; 3 (9): 1422-34.

3) Immunohistochemistry (IHC)

The collected lungs were fixed in PFA (paraformaldehyde) according to a conventional procedure, and then embedded in paraffin through washing, dehydration, and clearing. The paraffin blocks of Rat lung tissue were cut into 3 μm thickness and a slide were manufactured. The sample was first treated with xylene for 5 min three times, treated with 100% ethanol, 95% ethanol, 90% ethanol, and 70% ethanol, and DW in that order for 2 min, and washed with PBS for 5 min. After 0.3% $H_2O_2$ treatment, the sample was washed with PBS for 5 min twice. After soaking in 0.01 M citrate buffer and heated, the sample washed with PBS-T (0.03% tween 20), and then blocking was performed at room temperature for 30 minutes (2% BSA & 2% goat serum in PBS). It was stained overnight at 4° C. with anti-CD68 antibody (1:200, ED1 clone, Abcam). After washing three times with PBS-T for 5 minutes, the sample was treated with a polymer-HRP anti-mouse envision kit (DAKO) for 1 hour at 4° C. After washing three times with PBS-T, the sample was developed by treatment with DAB substrate buffer and DAB chromogen 20. The stained tissue was treated with Mayer's hematoxylin (Sigma) for 1 minute, and then treated twice for 2 minutes in order of 70% ethanol, 90% ethanol, 95% ethanol, and 100% ethanol. Finally, the tissue was treated with xylene three times for 5 min, and then observed under an optical microscope.

Results 10-1. Verification of Blood Pressure and Cardiac Output Changes.

Figure 11:
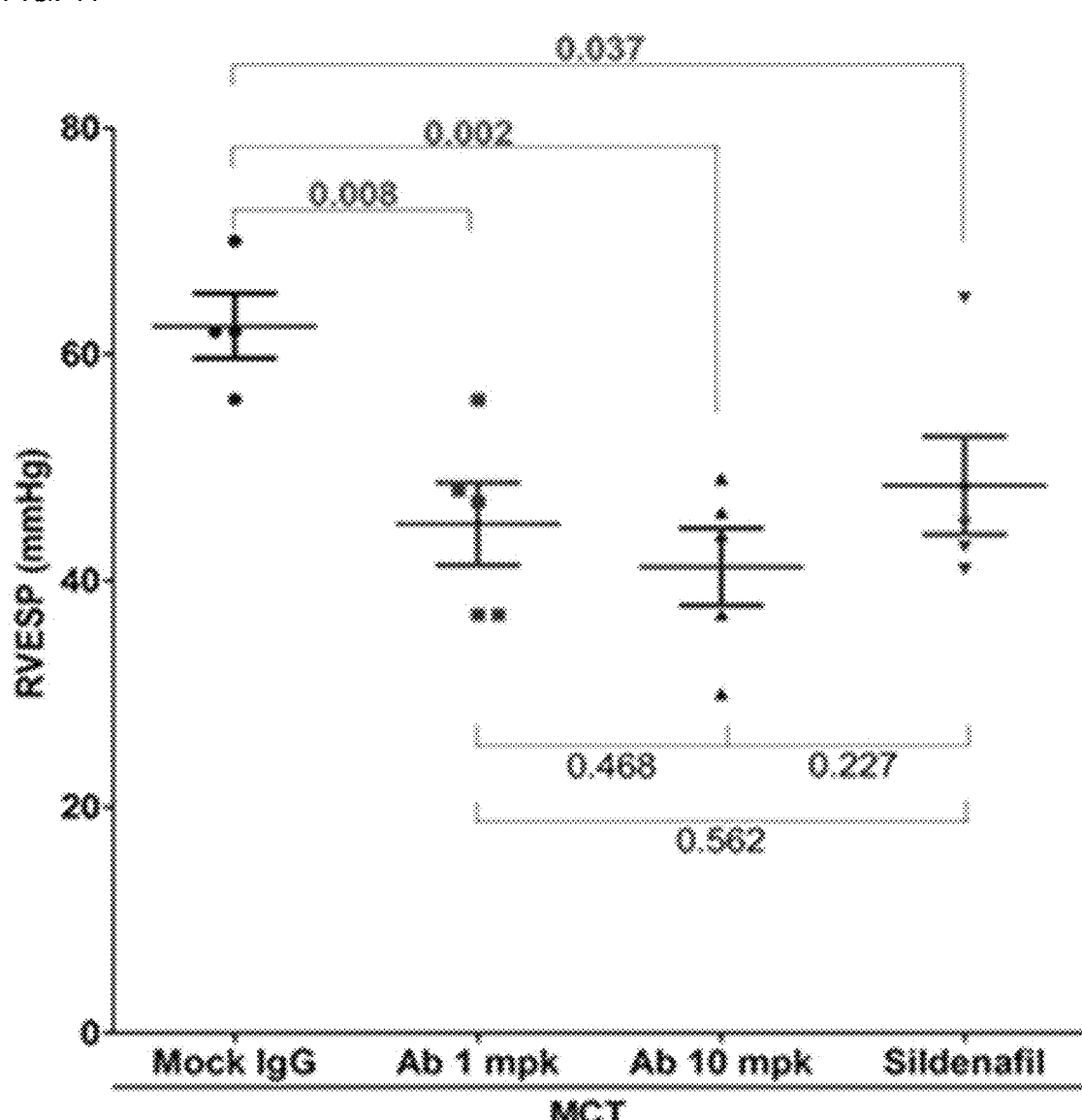
FIG. 11 shows the change of right ventricular end-systolic pressure (RVESP) in the pulmonary arterial hypertension (PAH) models by administration of the N3 antibody of the present invention (Mock IgG: negative control, Ab 1mpk: N3 antibody 1mpk, Ab 10 mpk: N3 antibody 10 mpk, sildenafil: positive control).

The animals with PAH, which is a disease having a close relation between immune cell invasion and pathological phenomena, were treated with N3 IgG antibody (1 mpk or 10 mpk) for 3 weeks (i.v., twice a week), and then measured for right ventricular end-systolic pressure (RVESP), right ventricular end-diastolic pressure (RVEDP), left ventricular end-systolic pressure (LVESP), left ventricular end-diastolic pressure (LVEDP), and cardiac output (CO). The results thereof are shown in Table 12.

ment. In contrast, as shown in FIG. 11, N3 antibody (an antibody specifically binding to KRS N-term) significantly reduced RVESP at both concentrations, and especially decreased RVESP better than Sildenafil, a positive control drug.

Figure 13:
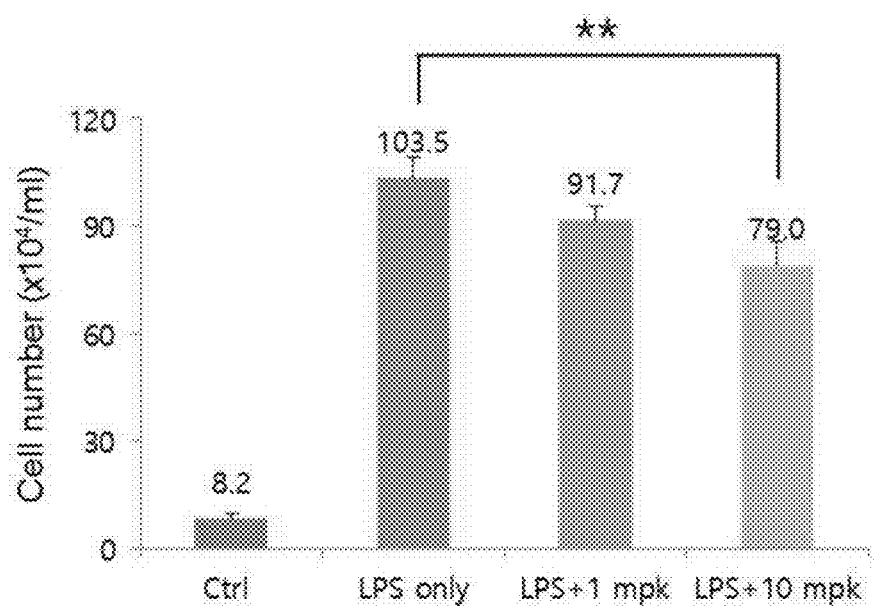
FIG. 13 shows the result of confirming that the total number of immune cells increased in the BALF (Broncho-alveolar lavage fluid) in the mouse models of acute lung injury were reduced depending on the treatment concentration of N3 antibody (antibody binding to the N-terminus of KRS).

In addition, there was no decrease in the left ventricular end systolic pressure (LVESP) following administration of the N3 antibody (an antibody specifically binding to KRS N-term). Instead, LVESP was significantly increased in the group administered with the antibody of the present invention as shown in FIG. 13. This is in contrast to the risk of lowering the systemic blood pressure by causing the expansion of the pulmonary artery, as well as the expansion of the systemic artery in the case of Sildenafil, which is used as a conventional treatment for pulmonary hypertension. That is, it was confirmed that the antibody of the present invention showed a tendency of having a low effect on systemic artery pressure compared with sildenafil, and this effect is thought to be a favorable characteristic of a therapeutic agent considering that sildenafil administration may be a risk of developing hypotension in clinical sites. Moreover, severe pulmonary arterial hypertension causes systolic RV failure, which may be accompanied by low cardiac output and systemic hypotension. Whereas, a treatment to alleviate pulmonary arterial hypertension by the N3 antibody of the present invention is expected to increase the cardiac output and systemic blood pressure, thereby normalizing the blood pressure.

In summary, it was confirmed that administration of the KRS N-term binding antibody (particularly, N3 antibody) of the present invention reduced the risk of side effects of existing therapeutic drugs and showed PAH symptom alleviation and treatment effects.

TABLE 12

|  | MCT + Mock IgG (n = 4) | MCT + N3 Ab 1 mpk (n = 5) | MCT + N3 Ab 10 mpk (n = 5) | MCT + Sildenafil (n = 5) |
|---|---|---|---|---|
| RVESP (mmHg) | 62.5 ± 5.7 | 45.0 ± 8.1 | 41.2 ± 7.7 | 48.4 ± 9.6 |
| RVEDP (mmHg) | 2.8 ± 1.5 | 1.4 ± 2.2 | 3.8 ± 1.3 | 2.6 ± 1.3 |
| LVESP (mmHg) | 81.5 ± 11.4 | 95.8 ± 4.8 | 93.4 ± 11.3 | 83.2 ± 4.7 |
| LVEDP (mmHg) | 1.0 ± 0.8 | 2.6 ± 1.9 | 4.6 ± 3.9 | 3.6 ± 2.3 |
| CO (ml/min) | 58 ± 4.7 (n = 4) | 74.0 ± 10.9 (n = 5) | 59.8 ± 12.9 (n = 5) | 49.6 ± 17.7 (n = 4) |

(CO was not measured in one animal of MCT + mock IgG group and one animal of sildenafil treatment group, since they died from anesthesia, and during surgery, respectively)

Pulmonary arterial hypertension causes the right ventricular pressure to rise due to narrowing of the pulmonary artery, resulting in right ventricular failure. In addition, if the reward mechanism is destroyed by persistent hypertension, right ventricular enlargement is followed by right ventricular hypertrophy. This causes the left ventricle compression due to the movement of the interventricular septum and a decrease in the left ventricular end diastolic volume and cardiac output (Lee Woo Seok et al., Clinical characteristics and prognostic factors of patients with severe pulmonary hypertension, Korean Circulation J. 2007; 37:265-270). As a result, pulmonary hypertension is primarily associated with the right ventricle, but also with the function of the left ventricle.

PAH patients showed a RVESP increase, which has also been confirmed in the PAH animal models of this experi- 10-2. Echocardiography The D-shaped left ventricle indicating pressure overload in the right ventricle was observed in three animals in the MCT alone administration group (i.e., animals without antibody treatment) and three animals in the MCT+sildenafil administration group, but was not observed in the therapeutic antibody administration groups.

In addition, as shown in Table 13 below, the weight of each group was increased to a similar degree, with no significant difference. That is, no abnormal signs including abnormal weight reduction were observed in the animals treated with the therapeutic antibody.

4) Masson's Trichrome Staining for Lung Tissue

TABLE 13

| | MCT + Mock IgG (n = 4) | MCT + Ab 1 mpk (n = 5) | MCT + Ab 10 mpk (n = 5) | MCT + Sildenafil (n = 5) |
|---|---|---|---|---|
| Absolute change (g) | 101.4 ± 14.2 | 113.5 ± 14.6 | 104.1 ± 12.3 | 104.1 ± 26.4 |
| Relative change (%) | 48.8 ± 7.8 | 43.6 ± 5.2 | 40.7 ± 5.0 | 49.8 ± 10.5 |

10-3. Verification of Monocyte/Macrophage Migration and Infiltration

Figure 12:
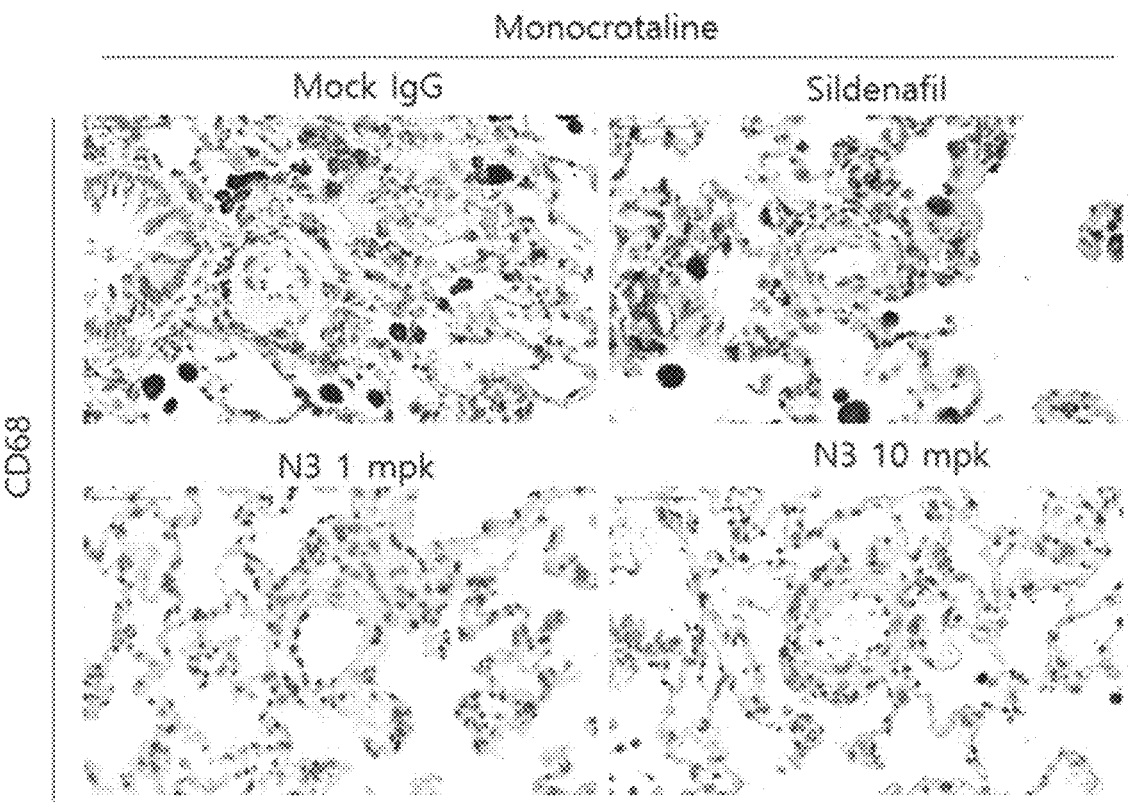
FIG. 12 is a result of confirming by IHC staining that immune cell migration and invasion are reduced by administration of the N3 antibody of the present invention in the pulmonary arterial hypertension (PAH) models.

IHC staining was performed with the lung tissues of each experimental group to detect CD68, which is a monocyte/macrophage marker. As shown in FIG. 12, it was confirmed that the N3 antibody (KRS N-term binding antibody) treatment group of the present invention explicitly reduced the monocyte/macrophage infiltration into lung tissues, and such effect was significantly excellent than that of sildenafil.

Example 11: Efficacy Verification of KRS-N Term Specific Antibodies in Immune Cell Migration-Related In Vivo Disease Models_Acute Lung Injury Models Methods 1) Construction of LPS-Induced Acute Lung Injury Models and Administration of Test Substance Acute lung injury was introduced into mice by intratracheal injection of 2.5 mg/kg LPS (Sigma) into 7-week-old male C57BL/6 mice (duothermal bio). To investigate the effects of KRS inhibitors on acute lung injury, first, the intravenous injection of N3 IgG antibody to C57BL/6 mice was performed at 1 mg/kg or 10 mg/kg, respectively, followed by endotracheal injection of 2.5 mg/kg of LPS after 24 hours. Twenty-four hours after the LPS injection, each mouse was sacrificed to collect and analyze lung tissue and BALF (Bronchoalveolar lavage fluid).

2) Immune Cell Count in Bronchoalveolar Lavage Fluid (BALF)

BALF obtained by washing the lungs with PBS was harvested and cell pellets were collected by centrifugation at 800×g for 10 minutes at 4° C. After the cells were suspended, red blood cells were removed using RBC lysis buffer (eBioscience cat.no.00-4333-57). After stopping the reaction with PBS, cells were washed twice, and suspended in 400 μl PBS to measure the number of cells by hemocytometer and neutrophil number through Hema3 staining.

3) FACS to Analyze Immune Cells in Lung Tissue

Lung tissues were collected and rotated for 45 min at 37° C. using gentleMACS Octo Dissociator (MACS Miltenyi Biotec, Order no. 130-095-937) to crush tissue. After filtering using a cell strainer (40 μm), cells were centrifuged at room temperature for 5 minutes at 1500 rpm. The pellet was collected and red blood cells were removed using RBC lysis buffer (eBioscience cat.no.00-4333-57). The cells were collected and suspended in FACS buffer (PBS containing 1% NaNs and 3% FBS). Cells (50 μl) were placed in a tube, mixed well with the same amount of antibody mixture, and stained by blocking light at 4° C. for 1 hour. FITC Rat Anti-CD11b (BD Pharmingen) and PE Rat Anti-Mouse F4/80 (BD Pharmingen) antibodies were used for analysis of interstitial macrophage (IM) infiltrated to the lungs. After washing twice at 400×g for 5 minutes using FACS buffer, cells were analyzed by Navios Flow Cytometer (Beckman).

4) Masson's Trichrome Staining for Lung Tissue

Lung tissue was embedded in paraffin in the original manner and then cut out. Thereafter, the tissue slide from which paraffin was removed using xylene was washed with DW, and then treated with Bouin Fluid at 56-60° C. for 1 hour. After stained with Weigert's iron hematoxylin solution for 10 minutes, the tissue slide was washed. After stained again with Biebrich scarlet-acid fuchsin solution for 10-15 minutes, the silde was washed. Phosphomolybdic-phosphotungstic acid solution was treated to the slide for 10-15 minutes, and then the slide was transferred to aniline blue solution and stained for 5-10 minutes. After washing, the slide was treated with 1% acetic acid solution for 2-5 minutes. After washing and dehydration, the slide was treated with xylene and mounted.

Results 11-1. Verification of the Inhibitory Effect on Immune Cell Migration in Bronchoalveolar Lavage Fluid (BALF)

As shown in FIG. 13, it was confirmed that the total number of immune cells in BALF was increased in mice where acute lung injury was induced by LPS treatment. The number of infiltrated immune cells was reduced by N3 antibody (KRS N-term binding antibody) treatment in a concentration dependent manner.

Figure 14:
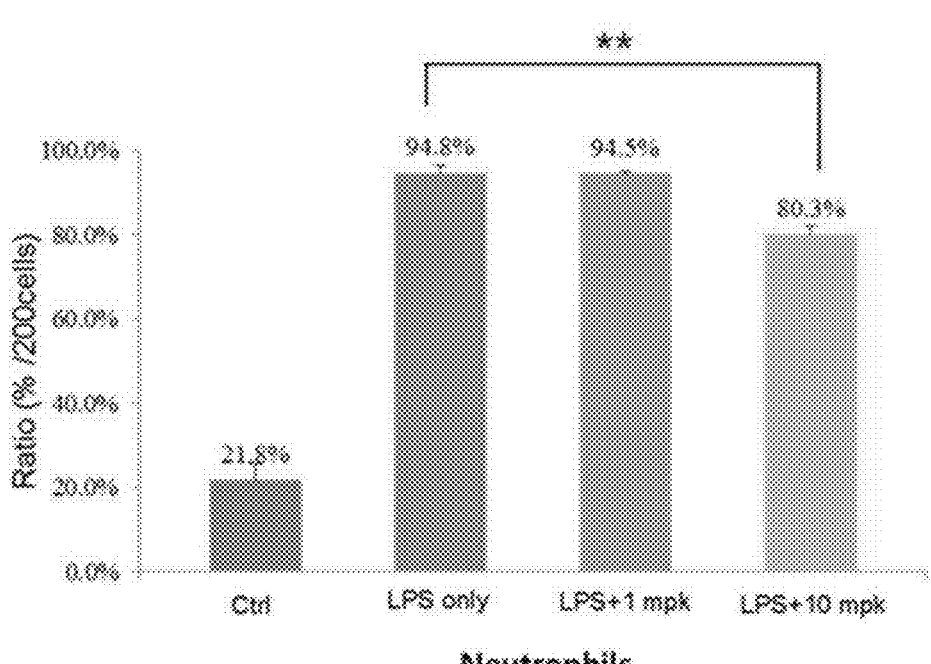
FIG. 14 shows the result of confirming that neutrophils which are particularly increased in bronchoalveolar lavage fluid (BALF) of the mouse models of acute lung injury were reduced depending on the treatment concentration of N3 antibody (antibody binding to the N-terminus of KRS).

In particular, as shown in FIG. 14, it was confirmed that neutrophils were increased in mice with acute lung injury by LPS treatment, and N3 antibody (KRS N-term binding antibody) treatment reduced these neutrophil levels. As a result, it was confirmed that infiltration of immune cells, particularly neutrophils, into lungs of BALF was significantly inhibited by treating the antibody specifically binding to KRS N-term.

Figure 15:
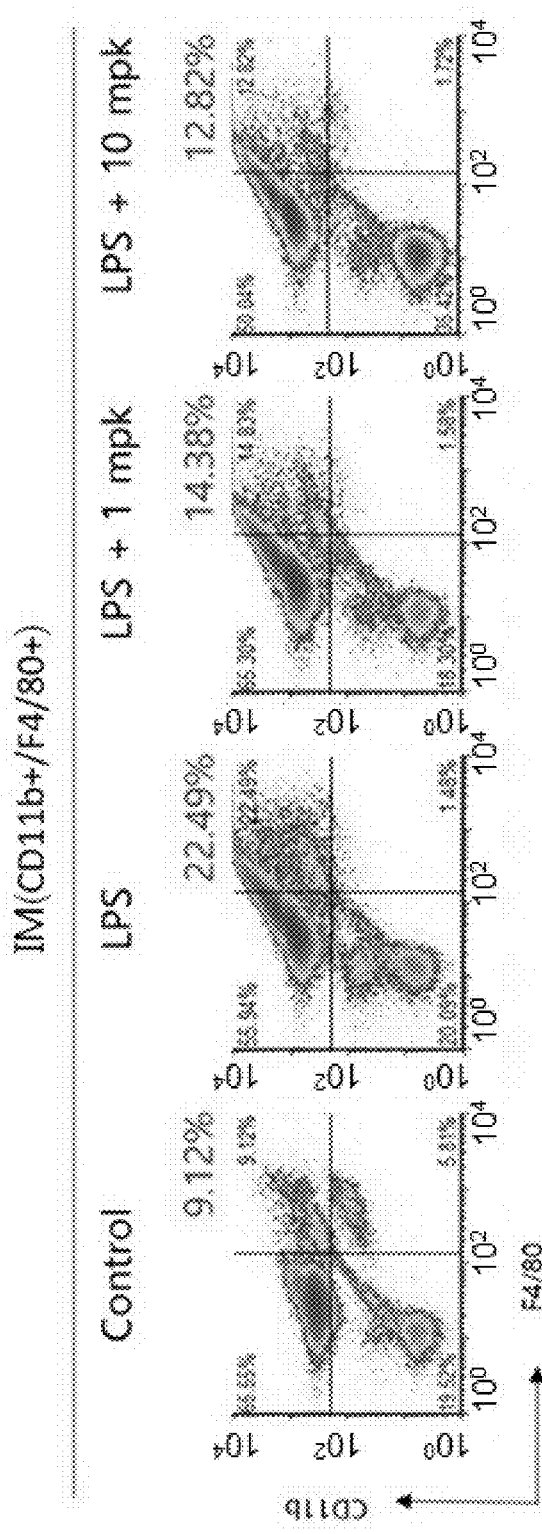
FIG. 15 shows the results of confirming by FACS that increased macrophage (IM, CD11b+/F4/80+) migration and invasion in the lung tissue of the mouse models of acute lung injury was reduced depending on the treatment concentration of N3 antibody (antibody binding to the N-terminus of KRS).
Figure 16:
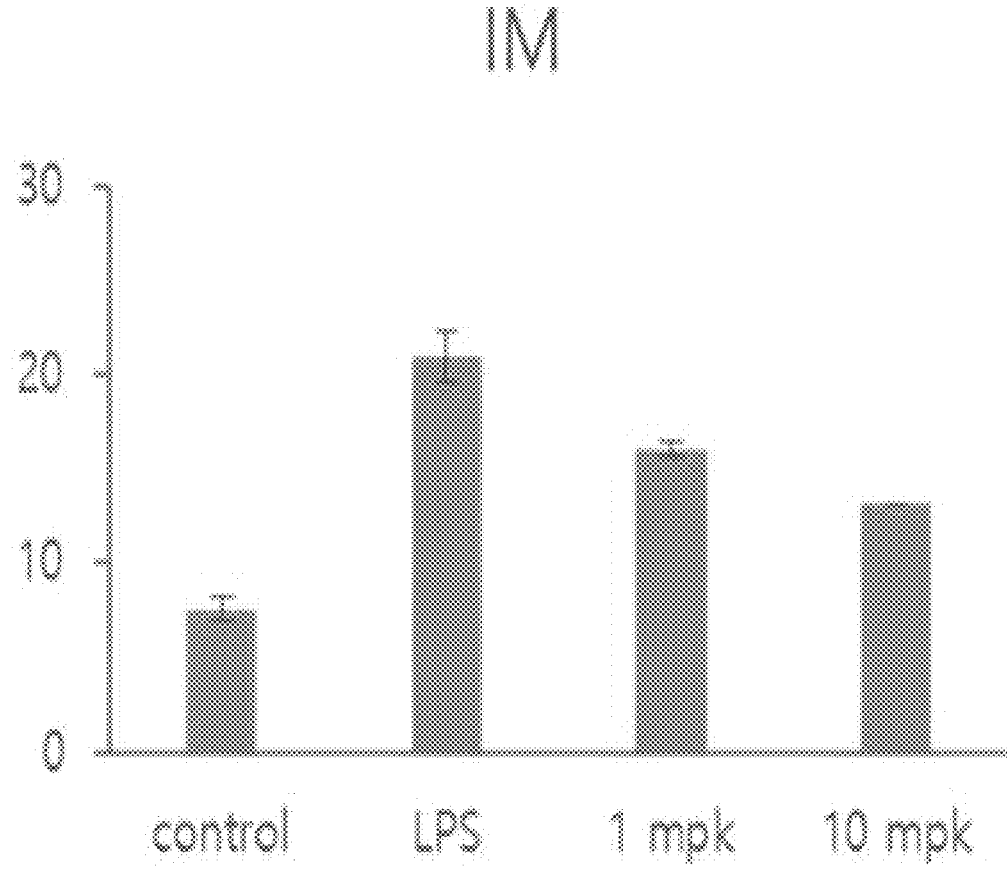
FIG. 16 is a graph quantifying the results of FIG. 15.

11-2. Verification of the Antibody Inhibitory Effect on Immune Cell Migration In Lung Tissue FIGS. 15 and 16 show the results of FACS analysis of macrophages migrated to lung tissue with acute lung injury. Interstitial macrophage (IM) is CD11b+/F4/80+ cells, which are migrating macrophages that do not reside in the lung but migrate to the lung in certain situations. LPS treatment increased the infiltration of IM into the lung, but N3 antibody treatment reduced the migration of IM to the lung in a concentration dependent manner. Through this, it was confirmed that the migration and invasion of immune cells such as macrophages/monocytes into lung tissues were inhibited by the treatment of antibodies (typically, N3 antibody) that specifically bind to KRS N-term.

Figure 17:
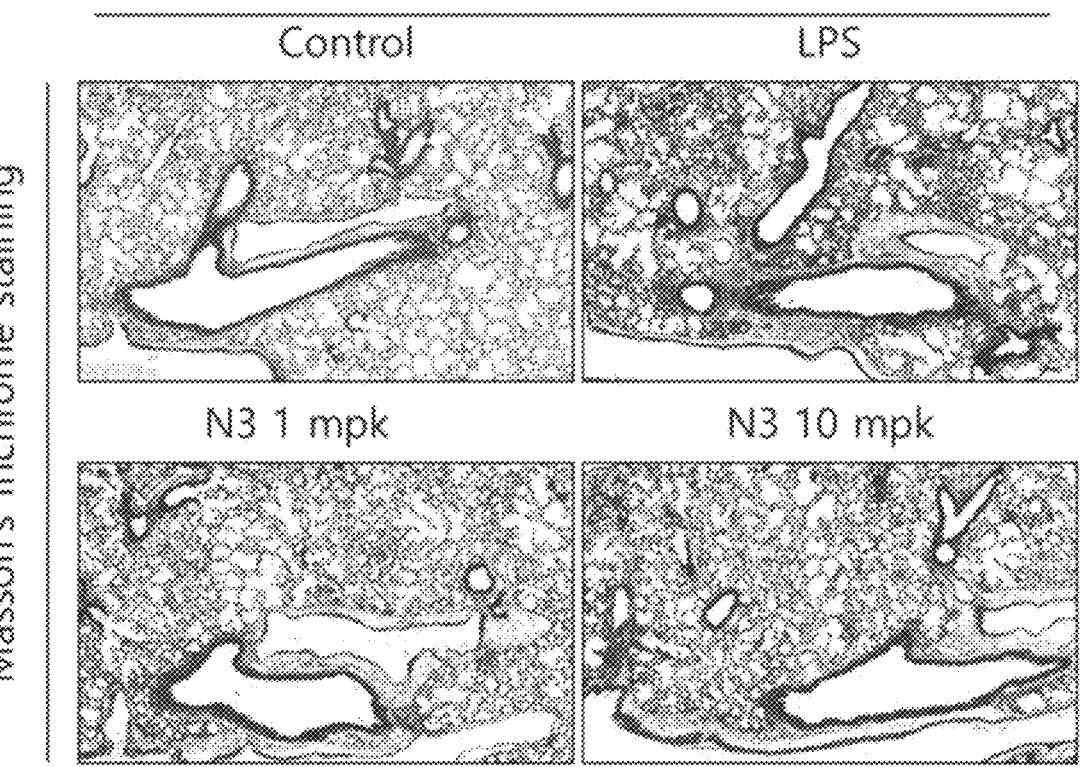
FIG. 17 is a tissue image showing that the tissue fibrosis advanced in lung tissue of the mouse models of acute lung injury mouse models is inhibited by treatment with an N3 antibody (KRS N-terminal binding antibody). Tissues of each experimental group and control group were observed under a microscope after Masson's trichrome staining.

The excessive migration and invasion of immune cells, such as macrophages/monocytes, are important pathological phenomena in tissues of fibrotic disease. As a result of observation of Masson's trichrome staining of lung tissue with respect to the acute lung injury model (FIG. 17), it was confirmed that fibrosis in the lung tissue proceeded considerably. In contrast, it was confirmed that the treatment of the N3 antibody (an antibody that specifically binds to KRS N-term) inhibited such fibrosis.

Example 12: Immune Cell Migration Analysis of Mutant Antibodies with ADCC/CDC Function Removed In order to confirm the effect of the mutant antibody from which the ADCC/CDC function had been removed on immune cell migration, a cell migration assay was performed according to the method described in the prior literature (Park, S. G. et al. Human lysyl-tRNA synthetase is secreted to trigger pro-inflammatory response, Proc. Natl. Acad. Sci. USA 102, 6356-6361 (2005)).

Measurements were made in a trans well chamber with a polycarbonate membrane (5.0 μm pore size, Costar). LN421 was put into the lower chamber at a concentration of 2.5 μg/ml in the trans well chamber. Then, RAW264.7 cells were placed in the upper chamber at a concentration of $5\times10^4$ cells per well. Then, each antibody was put into the chamber at a concentration of 10 nM, and then incubated for 24 hours. Then, it was washed twice with PBS and treated with 70% MeOH (in PBS). After washing twice with PBS again, the transferred cells were stained with crystal violet (Sigma) and dried. Then, the upper chamber was put in 33% acetic acid (Merck) and stirred for 10 minutes. Crystal violet-dissolved acetic acid solution was transferred to a 96-well plate, and absorbance was measured at 590 nm in a microplate reader (Tecan).

Figure 18:
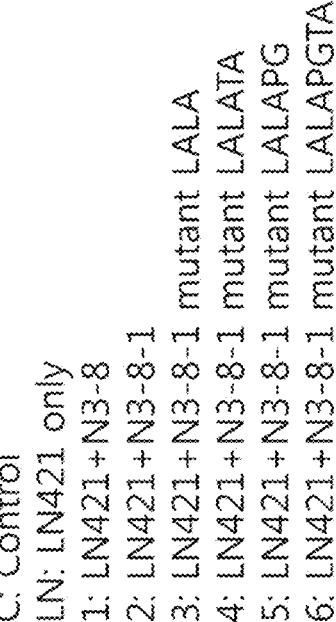
FIG. 18 shows the results confirming that cell migration was inhibited by treatment with N3-8, N3-8-1 antibodies, and N3-8-1 derivative antibodies from which ADCC/CDC functions were removed.
Figure 18:
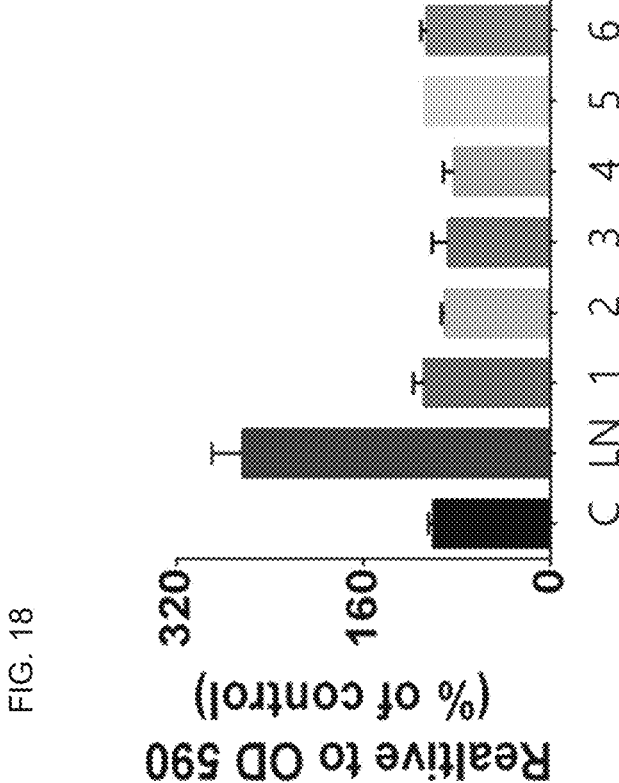

As a result, as shown in FIG. 18, it was found that all of the N3-8, N3-8-1, N3-8-1 mutant LALA, N3-8-1 mutant LALATA, N3-8-1 mutant LALAPG, N3-8-1 mutant LALAPGTA antibodies inhibited LN421-dependent cell migration at a level similar to that of the control group (Control, C) that was not treated with anything.

Example 13: Analysis for the Effect of Mutant Antibodies with ADCC/CDC Function Removed on Cancer Cell Migration In order to confirm the effect of the mutant antibody from which the ADCC/CDC function had been removed on immune cell migration, a cell migration assay was performed according to the method described in Example 12.

Measurements were made in a 24-well trans well chamber with a polycarbonate membrane (8.0 μm pore size, Costar). Laminin was added to the lower chamber at a concentration of 1 mg/ml, and a migration assay was performed using stable MDA-MB-231 cells overexpressing T52D KRS, which mimics a phosphorylated KRS. To induce T52D KRS expression, T52D KRS-MDA-MB-231 stable cells were treated with doxycycline (0.1 μg/ml) for one day, and then seeded in the upper chamber at a concentration of $4\times10^4$ cells after suspended in serum-free RPMI medium. Then, each 10 nM of N3-8, N3-8-1, N3-8-1 mutant LALA, N3-8-1 mutant LALATA, N3-8-1 mutant LALAPG, N3-8-1 mutant LALAPGTA antibody was added in the chamber and incubated for 7 hours. The non-migrating cells existing above the membrane were removed with a cotton swab. The membrane was washed twice with PBS and treated with 70% MeOH (in PBS) for 30 minutes. Again washed twice with PBS, the membrane was stained using crystal violet (Slgma), and dried. Then, the upper chamber was put in 33% acetic acid (Merck) and stirred. Crystal violet-dissolved acetic acid solution was transferred to a 96-well plate, and absorbance was measured at 590 nm in a microplate reader (Tecan).

Figure 19:
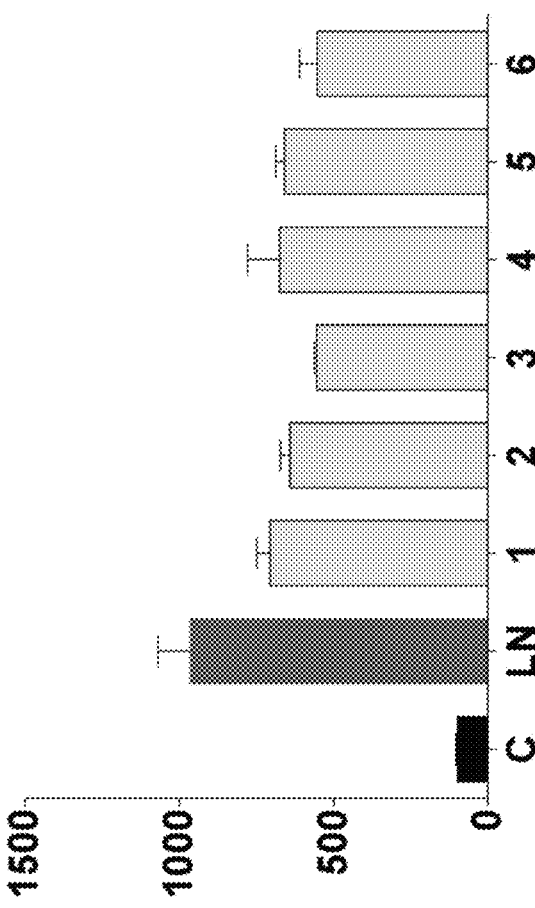
FIG. 19 shows the results confirming that cell migration of cancer cells was inhibited by treatment with N3-8, N3-8-1 antibodies, and N3-8-1 derivative antibodies from which ADCC/CDC functions have been removed.

As shown in FIG. 19, all of the N3-8, N3-8-1, N3-8-1 mutant LALA, N3-8-1 mutant LALATA, N3-8-1 mutant LALAPG, N3-8-1 mutant LALAPGTA antibodies inhibited the laminin-dependent migration of cancer cells.

INDUSTRIAL APPLICABILITY

As described above, the antibodies or fragments thereof of the present invention have a specific CDR (complementarity determining region) sequence described herein, and have very excellent specific binding capacity and affinity to the KRS N-terminal region exposed to the extracellular membrane. Therefore, it can be used for the diagnosis of diseases accompanying the specific behavior of KRS, such as cancer or immune cell migration-related diseases. And they have excellent productivity and stability, and excellent cancer metastasis inhibitory effect. Therefore, it can be usefully used as cancer therapeutics as well as preventor or inhibitor of cancer metastasis, and can be very useful in the prevention, improvement and treatment of diseases related to immune cell migration.

---

What is claimed is:

1. An antibody or fragment thereof that specifically binds to an extracellularly exposed lysyl-tRNA synthetase (KRS) N-terminal region, the antibody or fragment thereof comprises:

(a) a heavy chain variable region (VH) comprising (i) heavy chain complementarity determining region 1 (CDR1) containing the amino acid sequence SYDMS (SEQ ID NO: 1);

(ii) heavy chain complementarity determining region 2 (CDR2) containing the amino acid sequence $X_1IX_2X_3X_4X_5GX_6X_7YYADSVKG$ (SEQ ID NO: 252), wherein $X_1$ is A or V, $X_2$ is S, D or G, $X_3$ is Y, P, S or A, $X_4$ is D, Q, L or Y, $X_5$ is N, M, S, or G, $X_6$ is N, R or P, $X_7$ is T, V, I or S; and (iii) heavy chain complementarity determining region 3 (CDR3) containing the amino acid sequence $X_8ALDFDY$ (SEQ ID NO: 253), wherein $X_8$ is M or L, and (b) a light chain variable region (VL) comprising (i) light chain complementarity determining region 1 (CDR1) containing the amino acid sequence TGSSSNIGSNYVT (SEQ ID NO: 7);

(ii) light chain complementarity determining region 2 (CDR2) containing the amino acid sequence $X_9NX_{10}X_{11}RPS$ (SEQ ID NO: 254), wherein $X_9$ is D, S or R, $X_{10}$ is S or N, and $X_{11}$ is N or Q; and (iii) light chain complementarity determining region 3 (CDR3) containing the amino acid sequence $X_{12}SFSDELGAYV$ (SEQ ID NO: 255), wherein $X_{12}$ is A or S.

2. The antibody or fragment thereof of claim 1, wherein (a) the heavy chain variable region (VH) comprises a heavy chain complementarity determining region 1 (CDR1) containing the amino acid sequence of SEQ ID NO: 1; heavy chain complementarity determining region 2 (CDR2) containing one of the amino acid sequences selected from the group consisting of SEQ ID NO: 3, SEQ ID NO: 17, SEQ ID NO: 19, SEQ ID NO: 21, SEQ ID NO: 23, and SEQ ID NO: 118; and heavy chain complementarity determining region 3 (CDR3) containing one of the amino acid sequences selected from the group consisting of SEQ ID NO: 5 and SEQ ID NO: 25.

3. The antibody or fragment thereof of claim 1, wherein (b) the light chain variable region (VL) comprises a light chain complementarity determining region 1 (CDR1) containing the amino acid sequence of SEQ ID NO: 7; a light chain complementarity determining regions 2 (CDR2) containing one of the amino acid sequences selected from the group consisting of SEQ ID NO: 9, SEQ ID NO: 27 and SEQ ID NO: 29; a light chain complementarity determining region 3 (CDR3) containing one of the amino acid sequences selected from the group consisting of SEQ ID NO: 13 and SEQ ID NO: 15.

4. The antibody or fragment thereof of claim 1, wherein the antibody or fragment thereof comprises:

i) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 3, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 13;

ii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 3, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

iii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 118, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 13;

iv) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 118, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

v) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 17, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

vi) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 19, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

vii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

viii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 23, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

ix) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 27, and light chain complementary determining region 3 (CDR3) containing the amino acid sequence of SEQ ID NO: 15;

x) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 5, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 29, and light chain complementary determining region 3 (CDR3) containing the amino acid sequence of SEQ ID NO: 15;

xi) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 25, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 9, and light chain complementary determining region 3 (CDR3) containing the amino acid sequence of SEQ ID NO: 15;

xii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 25, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 27, and light chain complementary determining region 3 (CDR3) containing the amino acid sequence of SEQ ID NO: 15; or xiii) an antibody comprising an antibody heavy variable region (VH) comprising heavy chain complementary determining region 1 (CDR1) containing the amino acid sequence of SEQ ID NO: 1, heavy chain complementary determining region 2 (CDR2) containing the amino acid sequence of SEQ ID NO: 21, heavy chain complementary determining region 3 (CDR3) containing the amino acid sequence of SEQ ID NO: 25, and an antibody light chain variable region (VL) comprising light chain complementary determining region 1 (CDR1) containing the amino acid sequence of SEQ ID NO: 7, light chain complementary determining region 2 (CDR2) containing the amino acid sequence of SEQ ID NO: 29, and light chain complementary determining region 3 (CDR3) containing the amino acid sequence of SEQ ID NO: 15.

5. The antibody or fragment thereof of claim 1, wherein the antibody or fragment thereof contains a heavy chain (HC) comprising one of the amino acid sequences selected from the group consisting of SEQ ID NO: 89, SEQ ID NO: 93, SEQ ID NO: 95, SEQ ID NO: 97, SEQ ID NO: 99, SEQ ID NO: 101, SEQ ID NO: 103, and SEQ ID NO: 105; and a light chain (LC) comprising one of the amino acid sequences selected from the group consisting of SEQ ID NO: 107, SEQ ID NO: 109, SEQ ID NO: 111, SEQ ID NO: 113, and SEQ ID NO: 115.

6. The antibody or fragment thereof of claim 1, wherein the antibody or fragment thereof comprises:

a heavy chain containing the amino acid sequence of SEQ ID NO: 89, and a light chain containing the amino acid sequence of SEQ ID NO: 107;

a heavy chain containing the amino acid sequence of SEQ ID NO: 89, and a light chain containing the amino acid sequence of SEQ ID NO: 109;

a heavy chain containing the amino acid sequence of SEQ ID NO: 93, and a light chain containing the amino acid sequence of SEQ ID NO: 107;

a heavy chain containing the amino acid sequence of SEQ ID NO: 93, and a light chain containing the amino acid sequence of SEQ ID NO: 109;

a heavy chain containing the amino acid sequence of SEQ ID NO: 95, and a light chain containing the amino acid sequence of SEQ ID NO: 109;

a heavy chain containing the amino acid sequence of SEQ ID NO: 97, and a light chain containing the amino acid sequence of SEQ ID NO: 109;

a heavy chain containing the amino acid sequence of SEQ ID NO: 99, and a light chain containing the amino acid sequence of SEQ ID NO: 109;

a heavy chain containing the amino acid sequence of SEQ ID NO: 101, and a light chain containing the amino acid sequence of SEQ ID NO: 109;

a heavy chain containing the amino acid sequence of SEQ ID NO: 103, and a light chain containing the amino acid sequence of SEQ ID NO: 111;

a heavy chain containing the amino acid sequence of SEQ ID NO: 103, and a light chain containing the amino acid sequence of SEQ ID NO: 113;

a heavy chain containing the amino acid sequence of SEQ ID NO: 103, and a light chain containing the amino acid sequence of SEQ ID NO: 115;

a heavy chain containing the amino acid sequence of SEQ ID NO: 105, and a light chain containing the amino acid sequence of SEQ ID NO: 111;

a heavy chain containing the amino acid sequence of SEQ ID NO: 105, and a light chain containing the amino acid sequence of SEQ ID NO: 113;

a heavy chain containing the amino acid sequence of SEQ ID NO: 105, and a light chain containing the amino acid sequence of SEQ ID NO: 115;

a heavy chain containing the amino acid sequence of SEQ ID NO: 99, and a light chain containing the amino acid sequence of SEQ ID NO: 111;

a heavy chain containing the amino acid sequence of SEQ ID NO: 103, and a light chain containing the amino acid sequence of SEQ ID NO: 109.

7. The antibody or fragment thereof of claim 1, wherein the antibody is selected from the group consisting of IgG, IgA, IgM, IgE, and IgD, and the fragment is selected from the group consisting of diabody, Fab, Fab', F(ab)2, F(ab')2, Fv, and scFv.

8. The antibody or fragment thereof of claim 1, wherein the fragment contains one of the amino acid sequences selected from the group consisting of SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, and SEQ ID NO: 87.

9. The antibody or fragment thereof of claim 1, wherein the antibody is a polypeptide containing an Fc variant of a wild-type human IgG Fc region, and wherein the Fc variant comprises L117A, L118A, T182A, P212G of a wild-type human IgG1 Fc region of SEQ ID NO: 126 or at least one additional amino acid substitution which is T179A of the human IgG4 Fc region of SEQ ID NO: 138, and wherein the polypeptide has a reduced ADCC/CDC function compared to a polypeptide comprising the wild-type IgG Fc region.

10. A polynucleotide encoding the antibody or fragment thereof of claim 1.

11. A method for producing an antibody or fragment thereof that specifically binds to an extracellularly exposed lysyl-tRNA synthetase (KRS)N-terminal region, the method comprising:

(a) transforming host cells with a recombinant expression vector comprising the polynucleotide of claim 10;

(b) incubating the transformed host cells to produce an antibody or fragment thereof; and (c) collecting the antibody or fragment thereof produced in the host cells.

12. A method for inhibiting cancer and/or cancer metastasis, the method comprising:

administering an effective amount of a composition comprising the antibody or fragment thereof of claim 1 to a subject in need thereof, wherein the cancer is a cancer that overexpresses KRS N-terminal region on the cell membrane.

13. A method for diagnosing cancer or cancer metastasis, the method comprising:

a) obtaining a biological sample from an individual (subject) suspected of cancer metastasis;

b) administering a composition comprising the antibody or a fragment thereof of claim 1 to the sample or subject;

c) detecting the expression level of the KRS protein in the sample or subject of step b); and d) comparing the expression level of the KRS protein with a normal control group, and diagnosing that cancer and cancer metastasis have occurred when the expression level of KRS is increased, wherein the cancer is a cancer that overexpresses KRS N-terminal region on the cell membrane.

14. A method for treating an immune cell migration-related disease, the method comprising:

administering an effective amount of a composition comprising the antibody or fragment thereof of claim 1 to a subject in need thereof, wherein the immune cell migration-related disease is a disease that overexpresses KRS N-terminal region on the cell membrane, and is selected from the group consisting of a cardiovascular disease, a fibrotic disease, an inflammatory disease, and Alport syndrome.

15. A method for diagnosing an immune cell migration-related disease, the method comprising:

a) obtaining a biological sample from a subject suspected of an immune cell migration-related disease;

b) administering a composition comprising the antibody or a fragment thereof of claim 1 to the sample;

c) detecting the expression level of the KRS protein in the sample of step b); and d) comparing the expression level of the KRS protein with a normal control group, and diagnosing as an immune cell migration-related disease when the expression level of KRS is increased, wherein the immune cell migration-related disease is a disease that overexpresses KRS N-terminal region on the cell membrane, and is selected from the group consisting of a cardiovascular disease, a fibrotic disease, an inflammatory disease, and Alport syndrome.

\* \* \* \* \*